United States Patent
Christ et al.

(10) Patent No.: US 9,527,908 B2
(45) Date of Patent: Dec. 27, 2016

(54) MODIFIED VARIABLE DOMAIN MOLECULES AND METHODS FOR PRODUCING THEM

(71) Applicant: GARVAN INSTITUTE OF MEDICAL RESEARCH, Darlinghurst, New South Wales (AU)

(72) Inventors: Daniel Christ, Darlinghurst (AU); Kip Dudgeon, Darlinghurst (AU); Romain Rouet, Darlinghurst (AU)

(73) Assignee: GARVAN INSTITUTE OF MEDICAL RESEARCH, Darlinghurst (AU)

( * ) Notice: Subject to any disclaimer, the term of this patent is extended or adjusted under 35 U.S.C. 154(b) by 0 days.

(21) Appl. No.: 14/054,214

(22) Filed: Oct. 15, 2013

(65) Prior Publication Data

US 2014/0234218 A1 Aug. 21, 2014

Related U.S. Application Data

(63) Continuation-in-part of application No. PCT/AU2012/000403, filed on Apr. 19, 2012.

(30) Foreign Application Priority Data

Apr. 21, 2011 (AU) ................................ 2011901522
Nov. 21, 2011 (AU) ................................ 2011904856

(51) Int. Cl.
| | | |
|---|---|---|
| *C07K 16/18* | (2006.01) | |
| *C07K 16/22* | (2006.01) | |
| *C07K 16/32* | (2006.01) | |
| *C07K 16/24* | (2006.01) | |
| *A61K 49/00* | (2006.01) | |
| *C07K 1/22* | (2006.01) | |
| *G01N 33/53* | (2006.01) | |

(52) U.S. Cl.
CPC ........... *C07K 16/18* (2013.01); *A61K 49/0004* (2013.01); *C07K 1/22* (2013.01); *C07K 16/241* (2013.01); *C07K 16/32* (2013.01); *G01N 33/5308* (2013.01); *C07K 2317/56* (2013.01); *C07K 2317/565* (2013.01); *C07K 2317/622* (2013.01); *C07K 2317/90* (2013.01); *C07K 2317/92* (2013.01); *C07K 2317/94* (2013.01); *G01N 2800/00* (2013.01)

(58) Field of Classification Search
CPC ... C07K 16/241; C07K 16/32; C07K 2317/56; C07K 2317/565; C07K 2317/622; C07K 2317/92; C07K 2317/94; C07K 1/22; C07K 16/18; C07K 2317/90; A61K 49/0004; G01N 33/5308; G01N 2800/00
See application file for complete search history.

(56) References Cited

FOREIGN PATENT DOCUMENTS

WO WO2004101790 * 11/2004
WO WO 2009/041643 2/2009

OTHER PUBLICATIONS

Wu et al., J Mol Biol 294: 151-162, 1999.*
Dufner et al., Trends Biotechnol 24(11): 523-529, 2006.*
International Preliminary Report on Patentability issued in corresponding application PCT/AU2012/000403.
Bork, et al. "The Immunoglobulin Fold, Structural Classification, Sequence Patterns and Common Core" J. Mol. Biol., 1994, 242:309-320.
Carter, et al. "High level *Escherichia coli* expression and production of a bivalent humanized antibody fragment" Bio/Technology, Feb. 1992, 10(2):163-167.
Cornish-Bowden. "Nomenclature for incompletely specified bases in nucleic acid sequences: recommendations 1984" Nucleic Acids Research, 1985, 13(9):3021-3030.
Holbrook, et al. "Predicting surface exposure of amino acids from protein sequence" Protein Engineering, 1990, 3(8):659-665.
Saha, et al. "BcePred: Prediction of Continuous B-Cell Epitopes in Antigenic Sequences Using Physico-chemical Properties" Conference Paper, Sep. 2004.
Virnekas, et al. "Trinucleotide phosphoramidites: ideal reagents for the synthesis of mixed oligonucleotides for random mutagenesis" Nucleic Acids Research, 1994, 22(25):5600-5607.
Wang, et al. "TGF-β-dependent suppressive function of Tregs requires wild-type levels of CD18 in a mouse model of psoriasis" Journal of Clinical Investigation, Jul. 2008, 118(7):2629-2639.

* cited by examiner

*Primary Examiner* — Phuong Huynh
(74) *Attorney, Agent, or Firm* — Vedder Price P.C.; Thomas J. Kowalski; Deborah L. Lu

(57) ABSTRACT

The present disclosure provides an isolated, engineered or non-naturally occurring protein comprising an antibody light chain variable domain ($V_L$) which may comprise at least one negatively charged amino acid positioned between residues 49 to 56 according to the numbering system of Kabat, the protein capable of binding specifically to an antigen.

8 Claims, 20 Drawing Sheets

MODIFIED VARIABLE DOMAIN MOLECULES AND METHODS FOR PRODUCING THEM

RELATED APPLICATIONS AND INCORPORATION BY REFERENCE

This application is a continuation-in-part application of international patent application Serial No. PCT/AU2012/000403 filed 19 Apr. 2012, which published as PCT Publication No. WO 2012/142662 on 26 Oct. 2012, which claims benefit of and priority from Australian Patent Application No: 2011901522 entitled "Modified variable domain molecules and methods for producing same 3" filed on 21 Apr. 2011 and Australian Patent Application No: 2011904856 entitled "Modified variable domain molecules and methods for producing same 4" filed on 21 Nov. 2011. The entire contents of these applications are hereby incorporated by reference.

SEQUENCE LISTING

The application is filed with a Sequence Listing in electronic form. The entire contents of the Sequence Listing are hereby incorporated by reference.

FIELD OF THE INVENTION

The present disclosure relates to proteins which may comprise an aggregation-resistant antibody variable domain and uses thereof.

BACKGROUND OF THE INVENTION

Antibodies and proteins which may comprise antigen binding domains are now widely used as research reagents, diagnostic/prognostic reagents, industrial reagents and therapeutic agents. This broad ranging applicability arises from the ability of antibodies and proteins which may comprise antigen binding domains thereof to bind to an antigen with a high degree of specificity and affinity. Accordingly, antibodies and proteins which may comprise antigen binding domains thereof are able to bind specifically to an antigen in a sample and permit detection, quantification or to kill the cell expressing the antigen or to deliver a therapeutic payload. However, despite their versatility, only a subset of antibodies has the biophysical properties suited for diagnostic/prognostic/industrial/therapeutic application. For example, therapeutic or in vivo diagnostic antibodies/proteins require a long serum half-life in a subject to accumulate at the desired target, and they must therefore be resistant to aggregation (Willuda et al., 1999). Industrial applications often require antibodies/proteins that have a long half-life or can function following exposure to harsh conditions, e.g., high temperatures without aggregation (Harris, 1999). Aggregation of proteins which may comprise antibody variable domains can lead to difficulties in expression and/or purification, immunogenicity, toxicity, degradation, impaired avidity, or loss of activity following storage.

Protein aggregation is a process that competes with the folding pathway or can arise from intermediates in the folding pathway, and usually involves association of unfolded protein or partially unfolded protein. Resistance to aggregation can be achieved by stabilizing the native state (i.e., resisting unfolding) or by reducing the propensity of the unfolded or partially folded states of the protein to aggregate. A disadvantage of stabilizing the native state is that proteins will likely be exposed to an environment in which they will unfold. Generally, when a protein is denatured or unfolds, amino acid residues that normally mediate intramolecular contacts in the interior of the protein are exposed. Such exposure often makes proteins prone to form intermolecular contacts and aggregate. In contrast to proteins that resist unfolding, a protein having a reduced propensity to aggregate when unfolded will simply refold into a bioactive non-aggregated state after exposure to such an environment.

The aggregation-resistance or aggregation-propensity of antibodies and proteins which may comprise antigen binding domains thereof is usually limited by the most aggregation prone domain(s) contained therein and by the strength of its interaction with surrounding domains (if present). This is because once that domain unfolds, if it is incapable of refolding it may interact with other domains in the same protein or in other proteins and form aggregates. Constant domains of antibodies generally do not aggregate and do not vary considerably in sequence (as suggested by their name). Accordingly, the weakest domains of an antibody are generally considered to be those regions that vary from one antibody to the next, i.e., variable domains (e.g., heavy chain variable domain ($V_H$) and/or light chain variable domain ($V_L$)) (Ewert et al., 2003). In this regard, incorporation of aggregation prone scFv molecules into otherwise stable recombinant antibody products often imparts these generally undesirable traits to the new recombinant design. As stated in Ewert et al., 2008, "to improve any sub-optimal antibody construct by rational engineering, the "weakest link" has to be identified and improved". Ewert et al., also highlights that the variable domain is generally the "weakest link" in an antibody or antibody-related molecule. Thus, engineering a variable domain to be aggregation-resistant is most likely to render the entire protein which may comprise that variable domain aggregation-resistant.

Various strategies have been proposed for reducing aggregation of variable domains, e.g., rational design of aggregation-resistant proteins, complementarity determining region (CDR) grafting, or introducing disulfide bonds into a variable domain.

Rational design of aggregation-resistant proteins generally involves using in silico analysis to predict the effect of a point mutation on the aggregation propensity of a protein. However, there are several difficulties with this approach. For example, it is not sufficient to merely identify a mutation that is likely to reduce aggregation of an unfolded protein. Rather, the mutation must also not increase aggregation of a folded protein or affect the function of the folded protein. Furthermore, rational design requires detailed structural analysis of the specific protein being improved and thus, is difficult to use with a protein that has not been thoroughly characterized and is not readily applicable to a variety of different proteins.

CDR grafting involves transplanting CDRs from one variable domain onto framework regions (FRs) of another variable domain. This strategy was shown to be useful in stabilizing an anti-EGP-2 scFv (Willuda et al., 1999). However, this strategy is generally used to produce variable domains that resist unfolding, which as discussed above is not the most desirable form of protein. Disadvantages of this approach include the reduction in affinity that can occur following CDR grafting. This loss of affinity can be overcome by introducing mutations to the FRs, however such mutations can produce immunogenic epitopes in the protein, thereby making the protein undesirable from a therapeutic point of view. Furthermore, CDR grafting generally requires analysis of crystal structure or homology modeling of the donor and acceptor variable domains to assess suitability for grafting. Clearly, such an approach is laborious and requires specialized knowledge. Moreover, since each variable domain has a different structure, the method is not readily applied across a variety of molecules.

As for methods involving introducing disulfide bonds into a variable domain, while the bond may assist in the protein correctly refolding, it also introduces rigidity into the variable domain. Such rigidity can reduce the affinity of an antibody for an antigen. Moreover, not all variable domains can support the introduction of the requisite cysteine residues for disulfide bond formation without loss of affinity or without introducing an immunogenic epitope. Furthermore, formation of disulfide bonds under high protein concentrations can lead to protein aggregation, thus negating any potential positive effect of the bond.

As will be apparent from the foregoing, there is a need in the art for aggregation-resistant variable domain containing proteins and processes for their production. Preferably, the processes are readily applicable to a variety of distinct variable domains.

Citation or identification of any document in this application is not an admission that such document is available as prior art to the present invention.

SUMMARY OF THE INVENTION

In work leading up to the present invention, the inventors sought to identify amino acid residues in a variable domain of an antibody that conferred resistance to aggregation, e.g., following exposure to heat or concentration. Such aggregation-resistant proteins are useful for a variety of applications, e.g., therapy and/or diagnosis/prognosis. The ability to reduce aggregation during or following concentration (e.g., by lyophilization) also provides a benefit for production and/or storage of, e.g., therapeutic proteins, which can be manufactured as lyophilized proteins. The inventors introduced negatively charged amino acids into $V_L$ and identified numerous residues that confer aggregation resistance. The residues identified by the inventors occur within or adjacent to complementarity determining region 2 (CDR2) of a $V_L$. The inventors determined that single negatively charged amino acid residues in CDR2 of $V_L$ conferred aggregation-resistance upon the variable domain. The inventors additionally found that by including two or more negatively charged amino acids in CDR2 of a $V_L$ they could further increase the level of aggregation resistance. The inventors also found that they could modify a pre-existing $V_L$ to increase aggregation resistance and maintain the ability to bind to antigen. The inventors also found that they could modify a pre-existing $V_L$ (either alone or in a scFv) to increase aggregation resistance without significant reduction in the affinity of the VL or scFv for antigen.

The inventors also produced proteins which may comprise a $V_L$ with one or more negatively charged amino acids in or adjacent to CDR2 and an aggregation-resistant $V_H$ which may comprise one or more negatively charged amino acids in the region spanning amino acids 28-35 according to the numbering system of Kabat. The inventors found that these proteins demonstrate increased aggregation resistance and retain the ability to bind to antigen.

Because many of the residues identified by the inventors are in CDRs of an antibody, they are readily transferrable between different antibodies, e.g., antibodies of different classes or subclasses that may comprise different framework regions. This is because antibody variable domains have been selected to accommodate sequence variation in the CDRs, whereas the framework regions generally do not significantly vary since they provide a scaffold for presenting the CDR loops.

The findings by the inventors provide the basis for modified $V_L$ containing proteins (or $V_L$ and $V_H$ containing proteins) that are aggregation-resistant and various uses thereof.

Accordingly, the present disclosure provides an isolated, engineered or non-naturally occurring protein which may comprise a $V_L$ which may comprise a negatively charged amino acid at one or more positions between residues 49 and 56 according to the numbering system of Kabat, the protein capable of specifically binding to an antigen.

In one example, the protein additionally may comprise a $V_H$ which may comprise a charged residue in CDR1.

The present disclosure additionally or alternatively provides an isolated, engineered or non-naturally occurring protein which may comprise a $V_L$ which may comprise a negatively charged amino acid at two or more positions between residues 49 and 56 according to the numbering system of Kabat, the protein capable of specifically binding to an antigen.

In one example, the protein additionally may comprise a $V_H$ which may comprise a charged residue in CDR1.

The present disclosure additionally provides an isolated, engineered or non-naturally occurring protein which may comprise:
(i) a $V_L$ which may comprise a negatively charged amino acid at one or more positions between residues 49 and 56 according to the numbering system of Kabat; and
(ii) a $V_H$ which may comprise a negatively charged amino acid at one or more positions selected from the group consisting of residues 28, 30, 31, 32, 33 and 35 according to the numbering system of Kabat,
wherein the protein is capable of specifically binding to an antigen.

In one example, the protein may comprise a negatively charged amino acid at two or more positions between residues 49 and 56 of the $V_L$ or which may comprise a negatively charged amino acid at two or more positions selected from the group consisting of residues 28, 30, 31, 32, 33 and 35 of the $V_H$ according to the numbering system of Kabat.

The present disclosure additionally provides an isolated, engineered or non-naturally occurring protein which may comprise:
(i) a $V_L$ which may comprise a negatively charged amino acid at two or more positions between residues 49 and 56 according to the numbering system of Kabat; and
(ii) a $V_H$ which may comprise a negatively charged amino acid at two or more positions selected from the group consisting of residues 28, 30, 31, 32, 33 and 35 according to the numbering system of Kabat,
wherein the protein is capable of specifically binding to an antigen.

In one example, the $V_L$ may comprise a negatively charged amino acid at one or more (or two or more) positions selected from the group consisting of residues 49, 50, 51, 52, 53 and 56 according to the numbering system of Kabat.

In one example, the $V_L$ may comprise a negatively charged amino acid at one or more (or two or more) positions selected from the group consisting of residues 49, 50, 51, 52 and 53 according to the numbering system of Kabat.

In one example, the $V_L$ may comprise negatively charged amino acid at one or more (or two or more) positions within CDR2 according to the numbering system of Kabat.

Exemplary positions within a $V_L$ at which negatively charged amino acids confer aggregation resistance are selected from the group consisting of residues 50, 51, 52 and 53 and combinations thereof according to the numbering system of Kabat.

Exemplary combinations of positions within a $V_L$ at which negatively charged amino acids confer aggregation resistance are selected from the group consisting of:
(i) 50 and 51 according to the numbering system of Kabat;
(ii) 50 and 52 according to the numbering system of Kabat;
(iii) 50 and 53 according to the numbering system of Kabat;
(iv) 51 and 52 according to the numbering system of Kabat;
(v) 52 and 53 according to the numbering system of Kabat;
(vi) 50, 51 and 53 according to the numbering system of Kabat;
(vii) 51, 52 and 53 according to the numbering system of Kabat;
(viii) 50, 52 and 53 according to the numbering system of Kabat; and
(ix) 50, 51, 52 and 53 according to the numbering system of Kabat.

In one example, the VL may comprise negatively charged amino acids at positions 50, 52 and 53 according to the numbering system of Kabat.

In one example, the $V_L$ additionally may comprise a charged residue in CDR1 or CDR2.

In one example, the $V_L$ additionally may comprise a negatively charged amino acid at one or more positions in CDR1 according to the numbering system of Kabat. Exemplary positions are selected from the group consisting of:
(i) position 24 according to the numbering system of Kabat;
(ii) position 29 according to the numbering system of Kabat;
(iii) positions 30 and 31 according to the numbering system of Kabat; and
(iv) positions 31 and 32 according to the numbering system of Kabat.

In another example, the protein additionally may comprise a negatively charged amino acid at one or more residues selected from the group consisting of residues 26, 39, 40, 50, 52, 52a and 53 of $V_H$ according to the numbering system of Kabat.

In an additional or alternative example, the protein may comprise an aggregation-resistant $V_L$ and, optionally, an aggregation-resistant $V_H$.

In one example, the negatively charged amino acid residue(s) is/are surface exposed residues within the regions described herein. In accordance with this example, a protein does not comprise a negatively charged amino acid at position 54 of $V_L$ according to the numbering system of Kabat.

In one example, the negatively charged amino acid residue(s) is/are positioned at residues that do not directly interact with an antigen or do not form a bond with an antigen or are predicted not to directly interact with antigen or not to form a bond with an antigen. Methods for determining interaction or bond formation will be apparent to the skilled artisan and include, for example molecular modelling or x-ray crystallographic studies.

In one example, the protein has reduced tendency to aggregate compared to the protein without the negatively charged amino acid(s) discussed above. For example, the protein has reduced tendency to aggregate after heating to at least about 60° C. or 70° C. or, preferably, 80° C. compared to the protein without the negatively charged amino acid(s).

In one example, the protein retains the ability to specifically bind to the antigen after heating to at least about 60° C. or 70° C. or, preferably 80° C.

In another example, the protein has a reduced tendency to aggregate after concentration, e.g., lyophilization or concentration by diafiltration. In one example, the concentration may comprise dessication. In another example, the concentration may comprise reducing the volume of the composition in which the protein is contained by at least 50% or 60% or 70% or 80% or 85%.

For example, a protein of the disclosure has a reduced tendency to aggregate following lyophilization and reconstitution. For example, a protein of the disclosure aggregates 10% or 20% or 30% or 40% or 50% or 60% or 70% or 80% or 90% less than a protein lacking the negatively charged amino acids following lyophilization and reconstitution, wherein aggregation is measured by measuring turbidity, e.g., absorbance at 320 nm.

In another example, a protein of the disclosure has a reduced tendency to aggregate following diafiltration. For example, a protein of the disclosure aggregates 10% or 20% or 30% or 40% or 50% or 60% or 70% or 80% or 90% less than a protein lacking the negatively charged amino acids following diafiltration, wherein aggregation is measured by measuring turbidity, e.g., absorbance at 320 nm.

In one example, the protein is capable of binding to (preferably, specifically binding to) a human protein.

In another example, the protein is capable of binding to (preferably, specifically binding to) a protein associated with or causative of a human condition. Such a protein can be a human protein, or a protein from, e.g., an infectious organism. In one example, the protein is a human protein. Exemplary proteins are soluble and/or secreted proteins or receptors (e.g., extracellular domains of receptors) or membrane-bound proteins (e.g., extracellular domains of membrane-bound proteins).

In one example, the negatively charged amino acid is glutamic acid. In another example, the negatively charged amino acid is aspartic acid.

In one example, the negatively charged amino acid in a $V_L$ is aspartic acid.

In one example, the negatively charged amino acid at position 28 and/or 30 and/or 31 and/or 33 and/or 35 of a $V_H$ is aspartic acid.

In one example, the negatively charged amino acid at position 32 of a $V_H$ is aspartic acid or glutamic acid.

In an exemplary form, the protein may comprise a negatively charged amino acid at positions 32 and 33 of $V_H$ according to the numbering system of Kabat. In another exemplary form, the protein may comprise a negatively charged amino acid at positions 31 and 32 and 33 of $V_H$ according to the numbering system of Kabat.

In one exemplary form, a protein of the disclosure may comprise a negatively charged amino acid at position 52 and/or 53 of $V_L$ and a negatively charged amino acid at position 30 of $V_H$. In one example, the negatively charged amino acid is aspartic acid.

Additional exemplary positions for negatively charged amino acids in a $V_H$ are described in co-owned and copending International Application No. PCT/AU2010/001416, the entire contents of which are hereby incorporated by reference.

The present disclosure is also useful for producing modified forms of existing proteins that have improved aggregation-resistance. Accordingly, the present disclosure additionally provides a protein which may comprise a modified $V_L$ capable of specifically binding to an antigen, wherein the $V_L$ may comprise a negatively charged amino acid at one or more positions selected from the group consisting of residues 49, 50, 51, 52, 53 and 56 according to the numbering system of Kabat, and wherein the unmodified form of the $V_L$ does not comprise the negatively charged amino acid(s).

The present disclosure additionally provides a protein which may comprise a modified $V_L$ capable of specifically binding to an antigen, wherein the $V_L$ may comprise a negatively charged amino acid at two or more positions between residues 49 and 56 according to the numbering system of Kabat, and wherein the unmodified form of the $V_L$ does not comprise two or more negatively charged amino acid(s) at the positions.

The present disclosure additionally provides a protein which may comprise:
(i) a modified $V_L$ which may comprise a negatively charged amino acid at one or more positions between residues 49 and 56 according to the numbering system of Kabat, wherein the unmodified form of the $V_L$ does not comprise a negatively charged amino acid at the position; and
(ii) a modified $V_H$ which may comprise a negatively charged amino acid at one or more positions selected from the group consisting of residues 28, 30, 31, 32, 33 and 35 according to the numbering system of Kabat, wherein the unmodified form of the Vii does not comprise a negatively charged amino acid at the position,
wherein the modified protein is capable of specifically binding to an antigen.

The present disclosure additionally provides a protein modified to comprise:
(i) a $V_L$ which may comprise at least one negatively charged amino acid at one or more positions between residues 49 and 56 according to the numbering system of Kabat; and
(ii) a $V_H$ which may comprise at least one negatively charged amino acid at one or more positions selected from the group consisting of residues 28, 30, 31, 32, 33 and 35 according to the numbering system of Kabat,
wherein the unmodified protein does not comprise the negatively charged amino acid in $V_L$ and the negatively charged amino acid in $V_H$ and wherein the modified protein is capable of specifically binding to an antigen.

In one example, the unmodified protein binds to the same antigen (e.g., same epitope) as the modified protein.

In one example, the affinity constant ($K_D$) of the modified protein binds to the antigen is within about 50% or 40% or 30% or 20% or 10% of the unmodified protein. In one example, the affinity constant (KD) of the modified protein binds to the antigen is within about 5% of the unmodified protein.

In one example, the association-rate ($K_a$) of the modified protein binds to the antigen is within about 50% or 40% or 30% or 20% or 10% of the unmodified protein. In one example, the association-rate ($K_a$) of the modified protein binds to the antigen is within about 5% of the unmodified protein.

In one example, the dissociation-rate ($K_d$) of the modified protein binds to the antigen is within about 50% or 40% or 30% or 20% or 10% of the unmodified protein. In one example, the dissociation-rate ($K_d$) of the modified protein binds to the antigen is within about 5% of the unmodified protein.

In one example, the protein may comprise a modified aggregation-resistant $V_L$ and, optionally, a modified aggregation-resistant $V_H$.

Exemplary features of such a protein (e.g., additional sites for negatively charged amino acids and/or specific negatively charged amino acids) are described herein and shall be taken to apply mutatis mutandis to the present form of the disclosure.

In one example, the protein is an antibody.

In one example, a protein as described herein according to any example does not comprise a disulfide bond within a CDR, e.g., an intra-CDR disulphide bond, e.g., within CDR3.

In another example, a variable domain within the protein as described herein according to any example does not have an overall acidic isoelectric point.

Exemplary proteins of the present disclosure are human, humanized or deimmunized, or are fused to a human protein or region thereof (e.g., are chimeric antibodies).

In one example, the protein of the present disclosure is in the form of a single domain antibody (dAb) or a dAb fused to another protein (e.g., a Fc region or a protein capable of binding to an immune effector cell).

In an alternative example, a protein of the present disclosure may comprise a $V_L$ and a $V_H$, wherein the $V_H$ and the $V_L$ associate to form a Fv (e.g., which may comprise an antigen binding site). In one example, the Fv is capable of specifically binding to an antigen.

In one example, the $V_H$ and the $V_L$ are in different polypeptide chains. For example, the protein is in the form of an antibody, a diabody, a triabody, a tetrabody or a Fv.

In another example, the $V_H$ and the $V_L$ are in the same polypeptide chain. For example, the protein is in the form of a (scFv)n or a fusion protein which may comprise a (scFv)n, wherein n is a number, e.g., between 1 and 10.

In one example, a protein specifically binds to a target antigen or epitope with an affinity constant ($K_D$) of less than about 10 μM or 5 μM, for example less than 1 μM, for example, less than 500 nM, for example, less than 200 nM, such as less than 100 nM, and for example less than 10 nM, such as less than 1 nM.

In an alternative or additional example, any proteins discussed herein specifically binds to a target antigen or epitope with an affinity constant ($K_D$) of less than 100 pM, such as less than 10 pM, for example less than 1 pM.

In an additional or alternative example, any protein of the present disclosure dissociates from its target antigen(s) with a $K_d$ of 300 nM or less, 300 nM to 5 pM, preferably 50 nM to 20 pM, or 5 nM to 200 pM or 1 nM to 100 pM.

In one example, a protein as described herein according to any example, may comprise a $V_L$ which may comprise a sequence set forth in any one of SEQ ID NOs: 1, 3, 7 or 11 (such as, 7 or 11) modified to include at least one or two negatively charged amino acids between residues 49 and 56 or a sequence at least about 80% identical thereto.

In one example, a protein as described herein according to any example, may comprise a $V_L$ and a $V_H$ which may comprise sequences set forth in SEQ ID NO: 9, wherein the $V_L$ is modified to include at least one or two negatively charged amino acids between residues 49 and 56 or a sequence at least about 80% identical thereto and, optionally the $V_H$ is modified to include a negatively charged amino acid at one or more or two or more positions selected from the group consisting of residues 28, 30, 31, 32, 33 and 35 of the $V_H$ according to the numbering system of Kabat.

In one example, a protein as described herein according to any example, may comprise a $V_L$ and a $V_H$ which may comprise sequences set forth in SEQ ID NO: 13, wherein the $V_L$ is modified to include at least one or two negatively charged amino acids between residues 49 and 56 or a sequence at least about 80% identical thereto and, optionally the $V_H$ is modified to include a negatively charged amino acid at one or more or two or more positions selected from the group consisting of residues 28, 30, 31, 32, 33 and 35 of the $V_H$ according to the numbering system of Kabat.

Optionally a protein described in the foregoing three paragraphs may comprise an aspartic acid substituted for the N terminal glutamine in the $V_L$.

In one example, a protein as described herein according to any example may comprise a $V_L$ which may comprise a sequence set forth in SEQ ID NO: 11 modified to comprise at least one or two negatively charged amino acids between residues 49 and 56 according to the numbering system of Kabat, wherein the protein specifically binds to human epidermal growth factor receptor 2 (HER2).

In one example, the protein may comprise negatively charged amino acids at position 52 or 53 or at both positions 52 and 53 according to the numbering system of Kabat.

In one example, the protein additionally may comprise a $V_H$ which may comprise a sequence set forth in SEQ ID NO: 13 modified to include negatively charged amino acid(s) at one or more or two or more positions selected from the group consisting of residues 28, 30, 31, 32, 33 and 35 according to the numbering system of Kabat.

In one example, the $V_H$ may comprise a negatively charged amino acid at position 30.

The present disclosure also provides a protein of the present disclosure conjugated to a compound. For example, the compound is selected from the group consisting of a radioisotope, a detectable label, a therapeutic compound, a colloid, a toxin, a nucleic acid, a peptide, a protein, a compound that increases the half life of the protein in a subject and mixtures thereof.

The present disclosure also provides a composition which may comprise a protein of the present disclosure and a pharmaceutically acceptable carrier.

The present disclosure additionally provides a nucleic acid encoding a protein of the present disclosure. In one example, the nucleic acid is in an expression construct and is operably linked to a promoter. For example, the expression construct is an expression vector.

The present disclosure also provides a cell expressing a protein of the present disclosure. For example, the cell may comprise a nucleic acid or expression construct of the disclosure. Exemplary cells include mammalian cells, plant cells, fungal cells and prokaryotic cells.

The present disclosure also provides a method for producing a protein of the present disclosure, the method which may comprise maintaining an expression construct of the disclosure for a time and under conditions sufficient for (or such that) the encoded protein is produced. For example, the method may comprise culturing a cell of the disclosure for a time and under conditions sufficient for (or such that) a protein of the present disclosure is produced.

In one example, the method additionally may comprise isolating the protein of the present disclosure. In one example, the method additionally may comprise heating the protein, e.g., to at least about 50° C. or 60° C. or 70° C. or 80° C. (prior to, during or after isolating the protein. For example, the protein is heated to thereby reduce the amount of dimers and/or trimers that naturally occur during expression and purification processes. Such a method can facilitate recovery of increased levels of protein of the present disclosure.

Optionally, the method additionally may comprise conjugating the protein to a compound or formulating the compound into a pharmaceutical composition.

The present disclosure additionally provides a library which may comprise a plurality of proteins of the present disclosure.

The present disclosure also provides a library including proteins which may comprise $V_L$s, the $V_L$s which may comprise negatively charged amino acids at two or more positions between residues 49 and 56 according to the numbering system of Kabat.

The present disclosure additionally provides a library which may comprise proteins which may comprise antibody light chain variable domains ($V_L$s) and antibody heavy chain variable domains ($V_H$s), wherein the proteins comprise:

(a) a $V_L$ which may comprise a negatively charged amino acid at one or more positions between residues 49 and 56 according to the numbering system of Kabat; and (b) a $V_H$ which may comprise a negatively charged amino acid at one or more positions selected from the group consisting of residues 28, 30, 31, 32, 33 and 35 according to the numbering system of Kabat.

In one example, at least 30% (or 40% or 50% or 60% or 70% or 80% or 90% or 95% or 98% or 99%) of the proteins in the library comprise the negatively charged amino acids.

The present disclosure also provides a library which may comprise proteins which may comprise $V_L$s, wherein at least 30% (or 40% or 50% or 60% or 70% or 80% or 90% or 95% or 98% or 99%) of the $V_L$s comprise negatively charged amino acids at positions as described herein. The proteins can additionally comprise $V_H$s which may comprise negatively charged amino acids at positions described herein.

In one example, the proteins are displayed on the surface of a particle (e.g., a phage or a ribosome) or a cell.

In one example, the amino acids in the CDRs (e.g., in CDR3 or in CDR1 and 3 or in CDR 1, 2 and 3) of the $V_L$ and $V_H$ (if present) other than the negatively charged amino acids positioned as described above are random or semi-random or are derived from a human antibody.

Clearly, the present disclosure also provides a library of nucleic acids encoding the library.

The present disclosure additionally provides a method for isolating a protein of the present disclosure, the method which may comprise contacting a library of the disclosure with an antigen for a time and under conditions sufficient for (or such that) a protein binds to the antigen and isolating the protein.

The present disclosure additionally provides a method for producing a library which may comprise a plurality of proteins of the present disclosure, the method which may comprise:

(i) obtaining or producing nucleic acids encoding a plurality of proteins which may comprise $V_L$s, wherein the $V_L$s comprise a negatively charged amino acid at positions discussed above;

(ii) producing a library of expression constructs which may comprise the following operably linked nucleic acids:

a) a promoter.
b) a nucleic acid obtained or produced at (i); and
c) a nucleic acid encoding a polypeptide that facilitates display of the $V_L$ containing protein in/on the cells or particles; and
(iii) expressing proteins encoded by the expression constructs such that they are displayed in/on the cells or particles.

In one example, the amino acids in the CDRs of the $V_L$ (e.g., in CDR3 or in CDR1 and 3 or in CDR 1, 2 and 3) other than the negatively charged amino acids are random or semi-random or are derived from a human antibody.

In one example, the method additionally may comprise isolating nucleic acid encoding the protein. Such a nucleic acid can be introduced into an expression construct. Optionally, the protein can be expressed.

In one example, the method additionally may comprise exposing one or a plurality of the proteins which may comprise $V_L$s to heat and/or concentrating the proteins and selecting a protein having a reduced propensity to aggregate compared to a control protein lacking the negatively charged amino acids.

The present disclosure also contemplates modifications to the isolated, engineered or non-naturally occurring proteins, such as affinity maturation and/or humanization and/or deimmunization.

Such an isolated, engineered or non-naturally occurring protein can be used to produce, e.g., an antibody.

The present disclosure is also useful for reducing the aggregation propensity or increasing the aggregation-resistance of an existing antibody or protein which may comprise a $V_L$ and, optionally a $V_H$. For example, the present disclosure provides a method for increasing the aggregation-resistance of a protein which may comprise a $V_L$, the method which may comprise modifying the $V_L$ by substituting an amino acid at one or more positions selected from the group consisting of residues 49, 50, 51, 52, 53 and 56 according to the numbering system of Kabat with a negatively charged amino acid.

The present disclosure additionally provides a method for increasing the aggregation-resistance of a protein which may comprise a $V_L$, the method which may comprise modifying the $V_L$ such that it may comprise negatively charged amino acids at two or more positions between residues 49 and 56 according to the numbering system of Kabat, wherein the unmodified protein does not comprise the two or more negatively charged amino acids within CDR2 according to the numbering system of Kabat.

The present disclosure additionally provides a method for increasing the aggregation-resistance of a protein which may comprise a $V_L$ and a $V_H$, the method which may comprise modifying the protein such that it may comprise:
(i) a negatively charged amino acid at one or more positions between residues 49 and 56 of the $V_L$ according to the numbering system of Kabat; and
(ii) a negatively charged amino acid at one or more positions selected from the group consisting of residues 28, 30, 31, 32, 33 and 35 of the $V_H$ according to the numbering system of Kabat,
wherein the protein prior to modification does not comprise a negatively charged amino acid at the positions in the $V_L$ and the $V_H$.
In one example, the method may comprise:
(i) modifying the $V_L$ by substituting an amino acid at one or more positions between residues 49 and 56 of the $V_L$ according to the numbering system of Kabat with a negatively charged amino acid; and
(ii) modifying the $V_H$ by substituting an amino acid at one or more positions selected from the group consisting of residues 28, 30, 31, 32, 33 and 35 according to the numbering system of Kabat with a negatively charged amino acid.

The present disclosure additionally provides a method for increasing the aggregation-resistance of a protein which may comprise a $V_L$ and a $V_H$, the method which may comprise modifying the protein such that it may comprise:
(i) a negatively charged amino acid at two or more positions between residues 49 and 56 of the $V_L$ according to the numbering system of Kabat; and
(ii) a negatively charged amino acid at two or more positions selected from the group consisting of residues 28, 30, 31, 32, 33 and 35 of the $V_H$ according to the numbering system of Kabat,
wherein the protein prior to modification does not comprise a negatively charged amino acid at the positions in the $V_L$ and the $V_H$.
For example, the method may comprise:
(i) modifying the $V_L$ by substituting an amino acid at two or more positions between residues 49 and 56 of the $V_L$ according to the numbering system of Kabat with a negatively charged amino acid; and
(ii) modifying the $V_H$ by substituting an amino acid at two or more positions selected from the group consisting of residues 28, 30, 31, 32, 33 and 35 according to the numbering system of Kabat with a negatively charged amino acid.

In one example, the method additionally may comprise modifying the protein such that the $V_L$ additionally may comprise one or more negatively charged amino acids in CDR1 and/or the $V_H$ additionally may comprise a negatively charged amino acid at one or more residues selected from the group consisting of residues 26, 39, 40, 50, 52, 52a and 53 according to the numbering system of Kabat.

Additional sites of modification and/or specific amino acid residues that can be substituted are described herein and are to be taken to apply mutatis mutandis to the present example.

In one example, the method may comprise isolating a $V_L$ (and, optionally, a $V_H$) from the protein, modifying the $V_L$ (and, optionally, the $V_H$) according to a method of the disclosure and producing a protein which may comprise the $V_L$ (and, optionally, the $V_H$). For example, the method may comprise isolating a $V_L$ (and, optionally, the $V_H$) from an antibody, modifying the $V_L$ (and, optionally, the $V_H$) according to a method of the disclosure and producing an antibody which may comprise the modified $V_L$ (and, optionally, the $V_H$).

In one example, the method additionally may comprise determining the ability of the modified protein to bind to an antigen. In one example, the method additionally may comprise selecting a modified protein that binds to the antigen, e.g., with a similar (e.g., within about 10%) affinity (e.g., $K_D$, $K_a$ and/or $K_d$) to the unmodified protein.

In one example, a method of the disclosure additionally may comprise affinity maturing the $V_L$ (and, optionally, the $V_H$) or protein which may comprise same following modification according to the disclosure and/or deimmunizing the protein and/or humanizing the protein and/or chimerizing the protein.

In one example, the method additionally may comprise exposing the modified protein to heat and/or concentrating the protein and selecting a protein having a reduced propensity to aggregate compared to the unmodified protein.

In one example, a method of the disclosure does not involve inserting (as opposed to substituting) any additional amino acid residues into the $V_L$ (and, optionally, the $V_H$).

The methods described above are to be taken to apply mutatis mutandis to methods for increasing expression of a protein and/or for producing a protein capable of storage at high concentration with insignificant aggregation and/or for increasing recovery of a protein from a chromatography resin or for reducing the volume of solution required to recover a protein from a chromatography resin.

For example, the present disclosure provides a method for increasing the level of production of a soluble protein which may comprise an antibody $V_L$, the method which may comprise modifying the $V_L$ by substituting an amino acid at one or more positions selected from the group consisting of residues 51, 52 and 53 according to the numbering system of Kabat with a negatively charged amino acid, wherein the level of soluble protein produced is increased compared to the level of production of protein lacking the negatively charged amino acids.

The present disclosure additionally provides a method for increasing the level of production of a soluble protein which may comprise an antibody $V_L$, the method which may comprise modifying the $V_L$ such that it may comprise negatively charged amino acids at two or more positions between residues 49 and 56 according to the numbering system of Kabat, wherein the unmodified protein does not comprise the two or more negatively charged amino acids within CDR2 according to the numbering system of Kabat, and wherein the level of soluble protein produced is increased compared to the level of production of protein lacking the negatively charged amino acids.

The present disclosure additionally provides a method for increasing the level of production of a soluble protein which may comprise an antibody $V_L$ and $V_H$, the method which may comprise modifying the protein such that it may comprise:
  (i) a negatively charged amino acids at one or more positions between residues 49 and 56 of the $V_L$ according to the numbering system of Kabat; and
  (ii) a negatively charged amino acid at one or more positions selected from the group consisting of residues 28, 30, 31, 32, 33 and 35 of the $V_H$ according to the numbering system of Kabat,
  wherein the protein prior to modification does not comprise a negatively charged amino acid at the positions in the $V_L$ and the $V_H$, and wherein the level of soluble protein produced is increased compared to the level of production of protein lacking the negatively charged amino acids.

In one example, the method may comprise:
  (i) modifying the $V_L$ by substituting an amino acid at one or more positions between residues 49 and 56 of the $V_L$ according to the numbering system of Kabat with a negatively charged amino acid; and
  (ii) modifying the $V_H$ by substituting an amino acid at one or more positions selected from the group consisting of residues 28, 30, 31, 32, 33 and 35 according to the numbering system of Kabat with a negatively charged amino acid.

The present disclosure also provides a method for reducing the volume of solution required to recover a protein from a chromatography resin, the method which may comprise performing chromatography with a protein or a modified protein as described herein according to any example.

The present disclosure also provides a method for reducing the volume of solution required to recover a protein which may comprise an antibody $V_L$, from a chromatography resin, the method which may comprise modifying the $V_L$ of the protein by substituting an amino acid at one or more positions selected from the group consisting of residues 51, 52 and 53 according to the numbering system of Kabat with a negatively charged amino acid, and performing chromatography, the level of volume of solution required to recover a protein from a chromatography resin is reduced compared to the volume of protein lacking the negatively charged amino acids.

The present disclosure additionally provides a method for reducing the volume of solution required to recover a protein which may comprise an antibody $V_L$ from a chromatography resin, the method which may comprise modifying the $V_L$ such that it may comprise negatively charged amino acids at two or more positions between residues 49 and 56 according to the numbering system of Kabat, wherein the unmodified protein does not comprise the two or more negatively charged amino acids within CDR2 according to the numbering system of Kabat, and performing chromatography wherein the volume of solution required to recover the protein is reduced compared to the volume the protein lacking the negatively charged amino acids.

The present disclosure additionally provides a method for reducing the volume of solution required to recover a protein which may comprise an antibody $V_L$ and $V_H$ from a chromatography resin, the method which may comprise modifying the protein such that it may comprise:
  (i) a negatively charged amino acids at one or more positions between residues 49 and 56 of the $V_L$ according to the numbering system of Kabat; and
  (ii) a negatively charged amino acid at one or more positions selected from the group consisting of residues 28, 30, 31, 32, 33 and 35 of the $V_H$ according to the numbering system of Kabat,
  and performing chromatography, wherein the protein prior to modification does not comprise a negatively charged amino acid at the positions in the $V_L$ and the $V_H$, and the volume of solution required to recover the protein is reduced compared to the volume the protein lacking the negatively charged amino acids.

In one example, the method may comprise:
  (i) modifying the $V_L$ by substituting an amino acid at one or more positions between residues 49 and 56 of the $V_L$ according to the numbering system of Kabat with a negatively charged amino acid; and
  (ii) modifying the $V_H$ by substituting an amino acid at one or more positions selected from the group consisting of residues 28, 30, 31, 32, 33 and 35 according to the numbering system of Kabat with a negatively charged amino acid.

In one example, the chromatography is size-exclusion chromatography or bind-elute chromatography.

The present disclosure also provides for use of a protein of the present disclosure or a composition of the disclosure in medicine.

The present disclosure also provides a method of treating or preventing a condition in a subject, the method which may comprise administering a protein or composition of the disclosure to a subject in need thereof. In one example, the subject suffers from a cancer and/or an inflammatory disease and/or an autoimmune disease and/or a neurological condition.

The present disclosure also provides for use of a protein of the present disclosure in the manufacture of a medicament for the treatment or prevention of a condition.

The present disclosure also provides a method for delivering a compound to a cell, the method which may comprise contacting the cell with a protein or composition of the disclosure.

The present disclosure also provides a method for diagnosing or prognosing a condition in a subject, the method which may comprise contacting a sample from the subject with a protein or composition of the disclosure such that the protein binds to an antigen and forms a complex and detecting the complex, wherein detection of the complex is diagnostic or prognostic of the condition in the subject. In one example, the method may comprise determining the level of the complex, wherein an enhanced or reduced level of said complex is diagnostic or prognostic of the condition in the subject.

The present disclosure additionally provides a method for localising or detecting an antigen in a subject, said method which may comprise:
  (i) administering to a subject a protein or composition of the disclosure such that the protein to binds to an antigen, wherein the protein is conjugated to a detectable label; and
  (ii) detecting or localising the detectable label in vivo.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

KEY TO THE SEQUENCE LISTING

Figure 1:
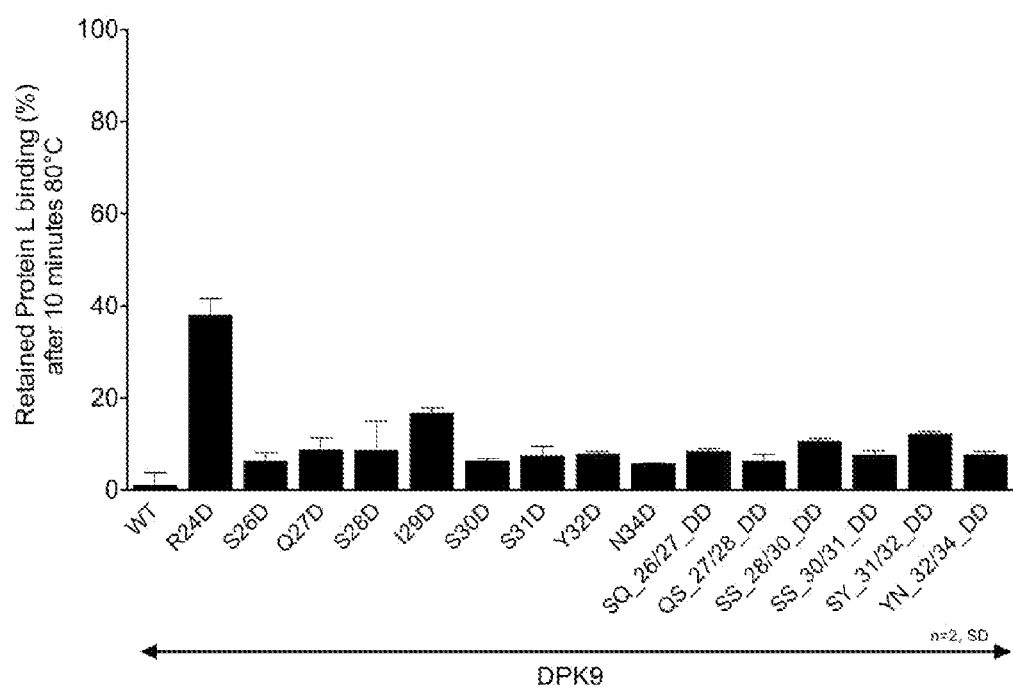
FIG. 1 is a graphical representation showing aggregation-resistance of $V_L$ from DPK9 which may comprise single negative charged amino acid changes, and combinations thereof in CDR1. Positioning of any substitutions is indicated on the X axis. Y-axis depicts percentage retained protein L binding when subjected to the "heat/cool" assay on phage exemplified herein. DPK9 is an example of a $V_L$ that has a low level of aggregation resistance.

SEQ ID NO: 1 is an amino acid sequence of DPK9 $V_L$.
SEQ ID NO: 2 is a nucleotide sequence encoding DPK9 $V_L$.
SEQ ID NO: 3 is an amino acid sequence of $V_Lk$ $V_L$.
SEQ ID NO: 4 is a nucleotide sequence encoding $V_Lk$ $V_L$.
SEQ ID NO: 5 is an amino acid sequence of a control scFv.
SEQ ID NO: 6 is a nucleotide sequence encoding a control scFv.
SEQ ID NO: 7 is an amino acid sequence of a $V_L$ from adalimumab.
SEQ ID NO: 8 is a nucleotide sequence encoding a $V_L$ from adalimumab.
SEQ ID NO: 9 is an amino acid sequence of a scFv derived from adalimumab.
SEQ ID NO: 10 is a nucleotide sequence encoding a scFv derived from adalimumab.
SEQ ID NO: 11 is an amino acid sequence of a $V_L$ from 4D5.
SEQ ID NO: 12 is a nucleotide sequence encoding a $V_L$ from 4D5.
SEQ ID NO: 13 is an amino acid sequence of a $V_H$ from 4D5.
SEQ ID NO: 14 is a nucleotide sequence encoding a $V_H$ from 4D5.
SEQ ID NO: 15 is an amino acid sequence of a scFv derived from 4D5.
SEQ ID NO: 16 is a nucleotide sequence encoding a scFv derived from 4D5.

DETAILED DESCRIPTION OF THE INVENTION

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

Those skilled in the art will appreciate that the present disclosure is susceptible to variations and modifications other than those specifically described. It is to be understood that the disclosure includes all such variations and modifications. The disclosure also includes all of the steps, features, compositions and compounds referred to or indicated in this specification, individually or collectively, and any and all combinations or any two or more of said steps or features.

The present disclosure is not to be limited in scope by the specific examples described herein, which are intended for the purpose of exemplification only. Functionally-equivalent products, compositions and methods are clearly within the scope of the disclosure, as described herein.

Any example of the disclosure herein shall be taken to apply mutatis mutandis to any other example of the disclosure unless specifically stated otherwise.

Any example herein directed to a protein which may comprise a $V_L$ of an antibody or use thereof shall be taken to apply mutatis mutandis to a protein which may comprise a variable domain an immunoglobulin or use thereof.

Unless specifically defined otherwise, all technical and scientific terms used herein shall be taken to have the same meaning as commonly understood by one of ordinary skill in the art (for example, in cell culture, molecular genetics, immunology, immunohistochemistry, protein chemistry, and biochemistry).

Unless otherwise indicated, the recombinant protein, cell culture, and immunological techniques utilized in the present disclosure are standard procedures, well known to those skilled in the art. Such techniques are described and explained throughout the literature in sources such as, J. Perbal, A Practical Guide to Molecular Cloning, John Wiley and Sons (1984), J. Sambrook et al. Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

The description and definitions of variable domains and parts thereof, immunoglobulins, antibodies and fragments thereof herein may be further clarified by the discussion in Kabat (1987 and/or 1991), Bork et al (1994) and/or Chothia and Lesk (1987 and 1989) or Al-Lazikani et al (1997).

The term "and/or", e.g., "X and/or Y" shall be understood to mean either "X and Y" or "X or Y" and shall be taken to provide explicit support for both meanings or for either meaning.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

As used herein the term "derived from" shall be taken to indicate that a specified integer may be obtained from a particular source albeit not necessarily directly from that source.

The term "between" when referring to amino acid residues or positions includes the terminal residues listed. For example, "between residues 49 and 56" includes residues 49, 50, 51, 52, 53, 54, 55 and 56.

In the context of the present disclosure, reference to a Markush group (i.e., "selected from the group consisting of") will be understood to encompass and provide explicit support for "selected individually or collectively from the group consisting of".

By "individually" is meant that the disclosure encompasses the recited residues or groups of residues separately, and that, notwithstanding that individual residue(s) or groups of residues may not be separately listed herein the accompanying claims may define such residue(s) or groups of residues separately and divisibly from each other.

By "collectively" is meant that the disclosure encompasses any number or combination of the recited residues or groups of residues, and that, notwithstanding that such numbers or combinations of residue(s) or groups of residues may not be specifically listed herein the accompanying claims may define such combinations or sub-combinations separately and divisibly from any other combination of residue(s) or groups of residues.

As used herein, the term "aggregation" means an association between or binding of proteins which is not reversible without treating the proteins with an agent that refolds the proteins into a native or unaggregated state. Such aggregation can lead to loss of function, loss of native fold, and/or gain of cytotoxicity or immunogenicity. This definition includes both detrimental and non-functional protein assemblies formed in vivo, and non-functional protein assemblies formed in vitro in biomedical research and biotechnology. It does not, however, include isoelectric or "salting out" precipitates, where the constituting proteins immediately return to their soluble native form upon transfer to native-like buffer conditions.

By "aggregation-resistant" is meant that following exposure to a condition that denatures a protein or induces or promotes aggregation of a protein or a domain thereof (e.g., heat or storage for a period of time, such as prolonged storage (e.g., for at least about 1 week or 1 month or two months or three months or 12 months) or concentration), a protein of the present disclosure does not aggregate or aggregates at a reduced level (e.g., 10% less or 20% less or 30% less or 40% less or 50% less or 60% less or 70% less or 80% less or 90% less) compared to a protein not comprising the negatively charged amino acids described herein and/or is capable of refolding and binding to a binding partner in a conformation specific manner. For example, after exposure to the condition, the protein is capable of specifically binding to an antigen and/or a superantigen, for example, Protein A or Protein L. In one example, following partial or complete denaturation (or unfolding) the protein is capable of refolding into a conformation that permits specific binding to the antigen or superantigen. Exemplary proteins do not significantly aggregate following exposure to a condition that generally denatures a protein or a domain thereof (e.g. heat). For example, more than about 10% or 20% or 30% or 40% or 50% or 60% or 70% or 80% or 90% or 95% of the protein of the present disclosure in a composition which may comprise a plurality of said proteins do not aggregate following exposure to heat, e.g., 60° C. or 70° C. or 80° C. Accordingly, a protein of the disclosure may also be considered heat refoldable. In another example, a protein does not aggregate when concentrated, e.g., by lyophilization and/or concentration at room temperature. For example, the protein aggregates about 10% or 20% or 30% or 40% or 50% or 60% or 70% or 80% or 90% less than a protein lacking the negatively charged amino acids following lyophilization and/or concentration at room temperature (e.g., by diafiltration).

As used herein, the term "antibody" shall be taken to mean a protein that may comprise a variable domain made up of a plurality of polypeptide chains, e.g., a light chain variable domain ($V_L$) and a heavy chain variable domain ($V_H$). An antibody also generally may comprise constant domains, which can be arranged into a constant region or constant fragment or fragment crystallisable (Fc). Antibodies can bind specifically to one or a few closely related antigens. Generally, antibodies comprise a four-chain structure as their basic unit. Full-length antibodies comprise two heavy chains (approximately 50-70 kD) covalently linked and two light chains (approximately 23 kD each). A light chain generally may comprise a variable domain and a constant domain and in mammals is either a κ light chain or a λ light chain. A heavy chain generally may comprise a variable domain and one or two constant domain(s) linked by a hinge region to additional constant domain(s). Heavy chains of mammals are of one of the following types α, δ, ε, γ, or μ. Each light chain is also covalently linked to one of the heavy chains. For example, the two heavy chains and the heavy and light chains are held together by inter-chain disulfide bonds and by non-covalent interactions. The number of inter-chain disulfide bonds can vary among different types of antibodies. Each chain has an N-terminal variable domain ($V_H$ or $V_L$ wherein each are approximately 110 amino acids in length) and one or more constant domains at the C-terminus. The constant domain of the light chain ($C_L$ which is approximately 110 amino acids in length) is aligned with and disulfide bonded to the first constant domain of the heavy chain ($C_H$ which is approximately 330-440 amino acids in length). The light chain variable domain is aligned with the variable domain of the heavy chain. The antibody heavy chain can comprise 2 or more additional $C_H$ domains (such as, $C_H2$, $C_H3$ and the like) and can comprise a hinge region can be identified between the $C_H1$ and $C_H2$ constant domains. Antibodies can be of any type (e.g., IgG, IgE, IgM, IgD, IgA, and IgY), class (e.g., $IgG_1$, $IgG_2$, $IgG_3$, $IgG_4$, $IgA_1$ and $IgA_2$) or subclass. In one example, the antibody is IgG, such as $IgG_3$. In on example, the antibody is a murine (mouse or rat) antibody or a primate (such as, human) antibody. The term "antibody" also encompasses humanized antibodies, primatized antibodies, deimmunized antibodies, human antibodies and chimeric antibodies. This term does not encompass antibody-like molecules such as T cell receptors, such molecules are encompassed by the term "immunoglobulin".

As used herein, "variable domain" refers to the portions of the light and heavy chains of an antibody or immunoglobulin as defined herein that includes amino acid sequences of CDRs; i.e., CDR1, CDR2, and CDR3, and FRs. $V_H$ refers to the variable domain of the heavy chain. $V_1$, refers to the variable domain of the light chain. According to the methods used in this disclosure, the amino acid positions assigned to CDRs and FRs are defined according to Kabat (1987 and 1991) and numbered according to the numbering system of Kabat. The skilled artisan will be readily able to use other numbering systems in the performance of this disclosure, e.g., the hypervariable loop numbering system of Clothia and Lesk (1987) and/or Chothia (1989) and/or Al-Lazikani et al (1997). For example, CDR2 of a $V_L$ is defined at the same position using the numbering system of Kabat or Clothia and Lesk (1987) and/or Chothia (1989).

As used herein, the term "heavy chain variable domain" or "$V_H$" shall be taken to mean a protein capable of binding to one or more antigens, preferably specifically binding to one or more antigens and at least a CDR1. Preferably, the heavy chain may comprise three or four FRs (e.g., FR1, FR2, FR3 and optionally FR4) together with three CDRs. In one example, a heavy chain may comprise FRs and CDRs positioned as follows residues 1-30 (FR1), 26-35 or 31-35 (or 35b) (CDR1), 36-49 (FR2), 50-65 (CDR2), 66-94 (FR3), 95-102 (CDR3) and 103-113 (FR4), numbered according to the numbering system of Kabat. In one example, the heavy chain is derived from an antibody which may comprise said heavy chain and a plurality of (preferably 3 or 4) constant domains or linked to a constant fragment (Fc).

As used herein, the term "light chain variable domain" or "$V_L$" shall be taken to mean a protein capable of binding to one or more antigens, preferably specifically binding to one or more antigens and at least which may comprise a CDR1. Preferably, the light chain may comprise three or four FRs (e.g., FR1, FR2, FR3 and optionally FR4) together with three CDRs. Preferably, a light chain may comprise FRs and CDRs positioned as follows residues 1-23 (FR1), 24-34 (CDR1), 35-49 (FR2), 50-56 (CDR2), 57-88 (FR3), 89-97 (CDR3) and 98-107 (FR4), numbered according to the numbering system of Kabat. In one example, the light chain is derived from an antibody which may comprise said light chain linked to one constant domain and/or not linked to a constant fragment (Fc).

In some examples of the disclosure the term "framework regions" will be understood to mean those variable domain residues other than the CDR residues. Each variable domain of a naturally-occurring antibody typically has four FRs identified as FR1, FR2, FR3 and FR4. If the CDRs are defined according to Kabat, exemplary light chain FR (LCFR) residues are positioned at about residues 1-23 (LCFR1), 35-49 (LCFR2), 57-88 (LCFR3), and 98-107 (LCFR4). Note that λLCFR1 does not comprise residue 10, which is included in κLCFR1. Exemplary heavy chain FR (HCFR) residues are positioned at about residues 1-30 (HCFR1), 36-49 (HCFR2), 66-94 (HCFR3), and 103-113 (HCFR4).

As used herein, the term "complementarity determining regions" (syn. CDRs; i.e., CDR1, CDR2, and CDR3 or hypervariable domain) refers to the amino acid residues of an antibody variable domain the presence of which are necessary for antigen binding. Each variable domain typically has three CDR regions identified as CDR1, CDR2 and CDR3. Each complementarity determining region may comprise amino acid residues from a "complementarity determining region" as defined by Kabat (1987 or 1991 or 1992). In one example of the present disclosure, in a heavy chain variable domain CDRH1 is between residues 26-35 (or 35b), CDRH2 is between residues 50-65 and CDRH3 is between residues 95-102 numbered according to the Kabat numbering system. In a light chain CDRL1 is between residues 24-34, CDRL2 is between residues 50-56 and CDRL3 is between residues 89-97 numbered according to the Kabat numbering system. These CDRs can also comprise numerous insertions, e.g., as described in Kabat (1987 and/or 1991 and/or 1992).

As used herein, the term "Fv" shall be taken to mean any protein, whether comprised of multiple polypeptides or a single polypeptide, in which a $V_L$ and a $V_H$ associate and form a complex having an antigen binding site, i.e., capable of specifically binding to an antigen. The $V_H$ and the $V_L$ which form the antigen binding site can be in a single polypeptide chain or in different polypeptide chains. Furthermore an Fv of the disclosure (as well as any protein of the present disclosure) may have multiple antigen binding sites which may or may not bind the same antigen. This term shall be understood to encompass fragments directly derived from an antibody as well as proteins corresponding to such a fragment produced using recombinant means. In some examples, the $V_H$ is not linked to a heavy chain constant domain ($C_H$) 1 and/or the $V_L$ is not linked to a light chain constant domain ($C_L$). Exemplary Fv containing polypeptides or proteins include a Fab fragment, a Fab' fragment, a F(ab') fragment, a scFv, a diabody, a triabody, a tetrabody or higher order complex, a domain antibody (e.g., a $V_H$) or any of the foregoing linked to a constant region or domain thereof, e.g., $C_H2$ or $C_H3$ domain. A "Fab fragment" consists of a monovalent antigen-binding fragment of an antibody, and can be produced by digestion of a whole immunoglobulin with the enzyme papain, to yield a fragment consisting of an intact light chain and a portion of a heavy chain or can be produced using recombinant means. A "Fab' fragment" of an antibody can be obtained by treating a whole antibody with pepsin, followed by reduction, to yield a molecule consisting of an intact light chain and a portion of a heavy chain. Two Fab' fragments are obtained per antibody treated in this manner. A Fab' fragment can also be produced by recombinant means. An "F(ab')2 fragment" of an antibody consists of a dimer of two Fab' fragments held together by two disulfide bonds, and is obtained by treating a whole antibody with the enzyme pepsin, without subsequent reduction. An "Fab$_2$" fragment is a recombinant fragment which may comprise two Fab fragments linked using, for example a leucine zipper or a $C_H3$ domain. A "single chain Fv" or "scFv" is a recombinant molecule containing the variable domain fragment (Fv) of an antibody in which the $V_L$ and $V_H$ are covalently linked by a suitable, flexible polypeptide linker. A detailed discussion of exemplary Fv containing proteins falling within the scope of this term is provided herein below.

As used herein, the term "antigen binding site" shall be taken to mean a structure formed by a protein that is capable of specifically binding to an antigen. The antigen binding site need not be a series of contiguous amino acids, or even amino acids in a single polypeptide chain. For example, in a Fv produced from two different polypeptide chains the antigen binding site is made up of a series of regions of a $V_L$ and a $V_H$ that interact with the antigen and that are generally, however not always in the one or more of the CDRs in each variable domain. In one example, reference herein to an antigen binding site is reference to the CDRs of an antibody or a variable region thereof.

A "constant domain" is a domain in an antibody, the sequence of which is highly similar in antibodies of the same type, e.g., IgG or IgM or IgE. A constant region of an antibody generally may comprise a plurality of constant domains, e.g., the constant region of γ, α and δ heavy chains comprise three constant domains and the Fc of γ, α and δ heavy chains comprise two constant domains. A constant region of μ and ε heavy chains may comprise four constant domains and the Fc region may comprise two constant domains.

The term "fragment crystalizable" or "Fc" as used herein, refers to a portion of an antibody which may comprise at least one constant domain and which is generally (though not necessarily) glycosylated and which binds to one or more Fc receptors and/or components of the complement cascade (e.g., confers effector functions). The heavy chain constant region can be selected from any of the five isotypes: α, δ, ε, γ, or μ. Furthermore, heavy chains of various subclasses (such as the IgG subclasses of heavy chains) are responsible for different effector functions and thus, by choosing the desired heavy chain constant region, proteins with desired effector function can be produced. Preferred heavy chain constant regions are gamma 1 (IgG1), gamma 2 (IgG2) and gamma 3 (IgG3).

By "numbering system of Kabat" is meant the system for numbering residues in a variable domain of an immunoglobulin in a consistent manner with the system set out in Kabat (1987 and/or 1991 and/or 1992).

The term "surface exposed" shall be understood to mean that the side chains of an amino acid are on the surface of a protein when folded such that they are capable of being in contact with a solvent in which the protein is present or suspended. In the case of a $V_L$, a surface exposed residue is for example, selected from the group consisting of residues 49, 50, 51, 52, 53 and 55 according to the numbering system of Kabat. Position 54 of $V_L$ according to the numbering system of Kabat is generally not surface exposed. Methods for predicting if an amino acid is surface exposed are known in the art and described, for example, in Holbrook et al., 1990.

The term "protein" shall be taken to include a single polypeptide, i.e., a series of contiguous amino acids linked by peptide bonds or a series of polypeptides covalently or non-covalently linked to one another (i.e., a polypeptide complex). For example, the series of polypeptides can be covalently linked using a suitable chemical or a disulphide bond. Examples of non-covalent bonds include hydrogen bonds, ionic bonds, Van der Waals forces, and hydrophobic interactions. A non-covalent bond contemplated by the present disclosure is the interaction between a $V_H$ and a $V_L$, e.g., in some forms of diabody or a triabody or a tetrabody or an antibody.

The term "polypeptide" will be understood to mean from the foregoing paragraph to mean a series of contiguous amino acids linked by peptide bonds.

As used herein, the term "antigen" shall be understood to mean any composition of matter against which an immunoglobulin response (e.g., an antibody response) can be raised. Exemplary antigens include proteins, peptides, polypeptides, carbohydrates, phosphate groups, phosphor-peptides or polypeptides, glyscosylated peptides or peptides, etc.

As used herein, the term "specifically binds" or "binds specifically" shall be taken to mean a protein of the present disclosure reacts or associates more frequently, more rapidly, with greater duration and/or with greater affinity with a particular antigen or antigens or cell expressing same than it does with alternative antigens or cells. For example, a protein that specifically binds to an antigen binds that antigen with greater affinity, avidity, more readily, and/or with greater duration than it binds to other antigens. It is also understood by reading this definition that, for example, a protein that specifically binds to a first antigen may or may not specifically bind to a second antigen. As such, "specific binding" does not necessarily require exclusive binding or non-detectable binding of another antigen. Generally, but not necessarily, reference to binding means specific binding, and each term shall be understood to provide explicit support for the other term.

As used herein, the term "modified" in the context of a $V_L$ (and, optionally, a $V_H$) means that the sequence of the $V_L$ is changed compared to a parent (or unmodified) $V_L$. For example, a $V_L$ which may comprise amino acids other than negatively charged amino acids between residues 49 and 56 is modified to substitute one or more of those amino acids with a negatively charged amino acid. For example, a $V_L$ is modified between residues 49 and 56 to increase the number of negatively charged amino acids at these positions, e.g., to a total of 1 or 2 or 3 or 4 or 5 or more. In one exemplary form, the number of negatively charged amino acids at the recited positions is increased to at least two.

The present disclosure contemplates any protein that may comprise an immunoglobulin light chain variable domain that specifically or selectively binds to one or more antigens and that is modified as described herein according to any example. The term "immunoglobulin" will be understood by the skilled artisan to include any protein of the immunoglobulin superfamily that comforms to the Kabat numbering system. Examples of immunoglobulin superfamily members include T cell receptors.

In one example, the present disclosure contemplates any protein that may comprise an antibody $V_L$ that specifically or selectively binds to one or more antigens, e.g., by virtue of an antigen binding site and that is modified as described herein according to any example.

As will be apparent to the skilled artisan based on the description herein, the proteins of the present disclosure can comprise one or more $V_L$s from an antibody modified to comprise a negatively charged amino acid at a position described herein (and, in some cases, a $V_H$ which can be modified, however is not necessarily modified as described herein). Such proteins include antibodies (e.g., an entire or full-length antibody). Such antibodies may be produced by first producing an antibody against an antigen of interest and modifying that antibody (e.g., using recombinant means) or by modifying a previously produced antibody. Alternatively, a protein which may comprise a $V_L$ of the disclosure is produced, and that protein is then modified or used to produce an antibody.

Methods for producing antibodies are known in the art. For example, methods for producing monoclonal antibodies, such as the hybridoma technique, are described by Kohler and Milstein, (1975). In a hybridoma method, a mouse, hamster, or other appropriate host animal, is typically immunized with an immunogen or antigen or cell expressing same to elicit lymphocytes that produce or are capable of producing antibodies that will specifically bind to the immunogen or antigen. Lymphocytes or spleen cells from the immunized animals are then fused with an immortalized cell line using a suitable fusing agent, such as polyethylene glycol, to form a hybridoma cell (Goding, 1986). The resulting hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells. Other methods for producing antibodies are also contemplated by the present disclosure, e.g., using ABL-MYC technology described generically in detail in Largaespada (1990) or Weissinger et al. (1991).

Alternatively, the antibody, or sequence encoding same is generated from a previously produced cell expressing an antibody of interest, e.g., a hybridoma or transfectoma. Various sources of such hybridomas and/or transfectomas will be apparent to the skilled artisan and include, for example, American Type Culture Collection (ATCC) and/or European Collection of Cell Cultures (ECACC). Methods for isolating and/or modifying sequences encoding $V_L$s from antibodies will be apparent to the skilled artisan and/or described herein. Exemplary antibodies that can be modified according to the present disclosure include, but are not limited to, SYNAGIS® (Palivizumab; MedImmune) which is a humanized anti-respiratory syncytial virus (RSV) monoclonal antibody; HERCEPTIN® (Trastuzumab; Genentech) which is a humanized anti-HER2 monoclonal antibody; REMICADE® (infliximab; Centocor) which is a chimeric anti-TNFα monoclonal antibody; REOPRO® (abciximab; Centocor) which is an anti-glycoprotein IIb/IIIa receptor antibody; ZENAPAX® (daclizumab; Roche Pharmaceuticals) which is a humanized anti-CD25 monoclonal antibody; RITUXAN™/MABTHERA™ (Rituximab) which is a chimeric anti-CD20 IgG1 antibody (IDEC Pharm/Genentech, Roche); STIMULECT™ (basilimimab; Novartis), which is a chimeric anti-IL-2Rα antibody; ERBITUX (cetuximab; ImClone), which is a chimeric anti-EGFR antibody; MYLOTARG™ (gemtuzumab; Celltech/Wyeth), which is a humanized anti-CD33 antibody); Campath 1H/LDP-03 (Alemtuzumab; ILEX/Schering/Millenium) which is a humanized anti CD52 IgG1 antibody; XOLAIR™ (omalizumab; Tanox/Genentech/Novartis) a humanized anti-IgE Fc antibody; AVASTIN® (Bevacizumab; Genentech) humanized anti-VEGF antibody; RAPTIVA™ (Efalizumab; Genentech/Merck Serono) which is a humanized anti-CD11a antibody; LUCENTIS (Ranibizumab; Genentech/Novartis) which is a humanized anti-VEGF-A antibody; TYSABRI™ (Natalizumab; Biogen Idec/Élan Pharmaceuticals) which is a humanized anti-integrin-α4 antibody; SOLIRIS™ (eculizumab; Alexion Pharmaceuticals) which is a humanized anti-complement protein C5 antibody; VECTIBIX® (Panitumumab; Amgen), fully human anti-EGFR monoclonal antibody; HUMIRA® (adalimumab; Abbott/MedImmune Cambridge) fully human anti-TNFα; SIMPONI® (golimumab anti-TNF alpha; Centocor Ortho Biotech, Inc); ARZERRA® (ofatumumab anti-CD20; Glaxo Group and GenMab AS); OMNITARG® (pertuzumab anti-Her2; Genentech, Inc). Other antibodies and proteins which may comprise a $V_L$ of an antibody are known in the art and are not excluded.

Sequence of $V_L$s of known antibodies will be readily obtainable by a person skilled in the art. Exemplary sequences include, the $V_L$ of adalimumab (SEQ ID NO: 7) or the $V_L$ of 4D5 (SEQ ID NO: 11). These sequences are readily modified according to the present disclosure.

Following antibody production and/or isolation of a sequence encoding same, the antibody or $V_L$ thereof is modified to include negatively charged amino acids (e.g., aspartic acid or glutamic acid) in the requisite positions to confer aggregation-resistance, e.g., as described herein according to any example. Generally, this may comprise isolating the nucleic acid encoding the $V_L$ or antibody and modifying the sequence thereof to include one or more codons encoding aspartic acid (i.e., GAA or GAG) or glutamic acid (i.e., GAT or GAC) at the requisite sites.

The proteins of the present disclosure may be a humanized antibody or a human antibody or $V_L$ therefrom. The term "humanized antibody" shall be understood to refer to a chimeric protein, generally prepared using recombinant techniques, having an antigen binding site derived from an antibody from a non-human species and the remaining antibody structure of the molecule based upon the structure and/or sequence of a human antibody. The antigen-binding site may comprise CDRs from the non-human antibody grafted onto appropriate FRs (i.e., the regions in a $V_L$ other than CDRs) in the variable domains of a human antibody and the remaining regions from a human antibody. Antigen binding sites may be wild type or modified by one or more amino acid substitutions. In some instances, framework residues of the human antibody are replaced by corresponding non-human residues. Humanized antibodies may also comprise residues which are found neither in the recipient antibody nor in the imported CDR or framework sequences. In general, the humanized antibody will comprise the CDRs of a non-human antibody and all or substantially all of the FR regions of a human antibody or consensus sequence thereof. Methods for humanizing non-human antibodies are known in the art. Humanization can be essentially performed following the method of U.S. Pat. No. 5,225,539, U.S. Pat. No. 6,054,297 or U.S. Pat. No. 5,585,089. Other methods for humanizing an antibody are not excluded.

The term "human antibody" as used herein in connection with antibodies and binding proteins refers to antibodies having variable and, optionally, constant antibody regions derived from or corresponding to sequences found in humans, e.g. in the human germline or somatic cells. The "human" antibodies can include amino acid residues not encoded by human sequences, e.g. mutations introduced by random or site directed mutations in vitro (in particular mutations which involve conservative substitutions or mutations in a small number of residues of the antibody, e.g. in 1, 2, 3, 4 or 5 of the residues of the antibody, preferably e.g.

in 1, 2, 3, 4 or 5 of the residues making up one or more of the CDRs of the antibody) and/or a negatively charged amino acid at a position described herein. Exemplary human antibodies or proteins comprise human framework regions (e.g., from the human germline) and random amino acids in the CDRs other than at the position(s) at which negatively charged amino acids are included. These "human antibodies" do not actually need to be produced by a human, rather, they can be produced using recombinant means and/or isolated from a transgenic animal (e.g., a mouse) which may comprise nucleic acid encoding human antibody constant and/or variable domains. Human antibodies or fragments thereof can be produced using various techniques known in the art, including phage display libraries (e.g., as described in Hoogenboom and Winter 1991; U.S. Pat. No. 5,885,793 and/or described below), or using transgenic animals expressing human immunoglobulin genes (e.g., as described in WO2002/066630; Lonberg et al. (1994) or Jakobovits et al. (2007)).

In one example, the protein of the present disclosure may comprise a human $V_L$. For example, the protein may comprise completely human framework regions.

In one example, the protein does not comprise a humanized V_or does not comprise a $V_L$ derived from a humanized antibody. In one example, the protein does not comprise a $V_L$ derived from humanized Fab4D5, e.g., as described in U.S. Pat. No. 6,407,213, such as humAb4D5, such as humAb4D5-1.

In one example, a protein as described herein does not bind to hen egg lysozyme.

In one example, a protein as described herein not bind to human vascular endothelial growth factor A (VEGF-A) and/or human her2/neu.

In one example a protein of the present disclosure is a chimeric antibody. The term "chimeric antibody" refers to antibodies in which a portion of the heavy and/or light chain is identical with or homologous to corresponding sequences in antibodies derived from a particular species (e.g., murine, such as mouse) or belonging to a particular antibody class or subclass, while the remainder of the chain(s) is identical with or homologous to corresponding sequences in antibodies derived from another species (e.g., primate, such as human) or belonging to another antibody class or subclass, as well as fragments of such antibodies, so long as they exhibit the desired biological activity (U.S. Pat. No. 4,816, 567). Typically chimeric antibodies utilize rodent or rabbit variable domains and human constant regions, in order to produce an antibody with predominantly human domains. For example, a chimeric antibody may comprise a variable domain from a mouse antibody modified according to the present disclosure fused to a human constant region. The production of such chimeric antibodies is known in the art, and may be achieved by standard means (as described, e.g., in U.S. Pat. No. 5,807,715; U.S. Pat. No. 4,816,567 and U.S. Pat. No. 4,816,397).

In some examples, a protein of the present disclosure is a single-domain antibody (which is used interchangeably with the term "domain antibody" or "dAb"). A single-domain antibody is a single polypeptide chain which may comprise all or a portion of the light chain variable domain of an antibody. In certain examples, a single-domain antibody is a human single-domain antibody (Domantis, Inc., Waltham, Mass.; see, e.g., U.S. Pat. No. 6,248,516; WO90/05144; WO2003/002609 and/or WO2004/058820). In one example, a single-domain antibody consists of all or a portion of the light chain variable domain of an antibody that is capable of specifically binding to an antigen and that is capable of modification according to the present disclosure. The present disclosure also encompasses a domain antibody fused to another molecule, e.g., another domain antibody or a Fc region.

Exemplary proteins which may comprise a $V_L$ are diabodies, triabodies, tetrabodies and higher order protein complexes such as those described in WO98/044001 and WO94/007921.

As used herein, the term "diabody" shall be taken to mean a protein which may comprise two associated polypeptide chains, each polypeptide chain which may comprise the structure $V_L$—X—$V_H$ or $V_H$—X—$V_L$, wherein $V_L$ is an antibody light chain variable domain, $V_H$ is an antibody heavy chain variable domain, X is a linker which may comprise insufficient residues to permit the $V_H$ and $V_L$ in a single polypeptide chain to associate (or form an Fv) or is absent, and wherein the $V_H$ of one polypeptide chain binds to a $V_L$ of the other polypeptide chain to form an antigen binding site, i.e., to form a Fv molecule capable of specifically binding to one or more antigens. The $V_L$ and $V_H$ can be the same in each polypeptide chain or the $V_L$ and $V_H$ can be different in each polypeptide chain so as to form a bispecific diabody (i.e., which may comprise two Fvs having different specificity).

As used herein, the term "triabody" shall be taken to mean a protein which may comprise three associated polypeptide chains, each polypeptide chain which may comprise the structure as set out above in respect of a diabody wherein the $V_H$ of one polypeptide chain is associated with the $V_L$ of another polypeptide chain to thereby form a trimeric protein (a triabody).

As used herein, the term "tetrabody" shall be taken to mean a protein which may comprise four associated polypeptide chains, each polypeptide chain which may comprise the structure set out above in respect of a diabody and wherein the $V_H$ of one polypeptide chain is associated with the $V_L$ of another polypeptide chain to thereby form a tetrameric protein (a tetrabody).

The skilled artisan will be aware of diabodies, triabodies and/or tetrabodies and methods for their production. The $V_H$ and $V_L$ can be positioned in any order, i.e., $V_L$-$V_H$ or $V_H$-$V_L$. Generally, these proteins comprise a polypeptide chain in which a $V_H$ and a $V_L$ are linked directly or using a linker that is of insufficient length to permit the $V_H$ and $V_L$ to associate. Proteins which may comprise $V_H$ and $V_L$ associate to form diabodies, triabodies and/or tetrabodies depending on the length of the linker (if present) and/or the order of the $V_H$ and $V_L$ domains. Preferably, the linker may comprise 12 or fewer amino acids. For example, in the case of polypeptide chains having the following structure arranged in N to C order $V_H$—X—$V_L$, wherein X is a linker, a linker having 3-12 residues generally results in formation of diabodies, a linker having 1 or 2 residues or where a linker is absent generally results in formation of triabodies. In the case of polypeptide chains having the following structure arranged in N to C order $V_L$—X—$V_H$, wherein X is a linker, a linker having 3-12 residues generally results in formation of diabodies, a linker having 1 or 2 residues generally results in formation of diabodies, triabodies and tetrabodies and a polypeptide lacking a linker generally forms triabodies or tetrabodies.

The skilled artisan will be aware that scFvs comprise $V_H$ and $V_L$ regions in a single polypeptide chain. Preferably, the polypeptide chain further may comprise a polypeptide linker between the $V_H$ and $V_L$ which enables the scFv to form the desired structure for antigen binding (i.e., for the $V_H$ and $V_L$ of the single polypeptide chain to associate with one another to form a Fv). This is distinct from a diabody or higher order multimer in which variable domains from different polypeptide chains associate or bind to one another. For example, the linker may comprise in excess of 12 amino acid residues with $(Gly_4Ser)_3$ being one of the more favoured linkers for a scFv.

The present disclosure also contemplates a disulfide stabilized Fv (or diFv or dsFv), in which a single cysteine residue is introduced into a FR of $V_H$ and a FR of $V_L$ and the cysteine residues linked by a disulfide bond to yield a stable Fv (see, for example, Brinkmann et al., 1993).

Alternatively, or in addition, the present disclosure provides a dimeric scFv, i.e., a protein which may comprise two scFv molecules linked by a non-covalent or covalent linkage. Examples of such dimeric scFv include, for example, two scFvs linked to a leucine zipper domain (e.g., derived from Fos or Jun) whereby the leucine zipper domains associate to form the dimeric compound (see, for example, Kostelny 1992 or Kruif and Logtenberg, 1996). Alternatively, two scFvs are linked by a peptide linker of sufficient length to permit both scFvs to form and to bind to an antigen, e.g., as described in US20060263367.

Modified forms of scFv are also contemplated by the present disclosure, e.g., scFv which may comprise a linker modified to permit glycosylation, e.g., as described in U.S. Pat. No. 6,323,322.

The skilled artisan will be readily able to produce a scFv or modified form thereof which may comprise a suitable modified $V_L$ according to the present disclosure based on the disclosure herein. For a review of scFv, see Plückthun (1994). Additional description of scFv is to be found in, for example, Bird et al., 1988.

The skilled artisan will be aware that a minibody may comprise the $V_H$ and $V_L$ domains of an antibody fused to the $C_H2$ and/or $C_H3$ domain of an antibody. Optionally, the minibody may comprise a hinge region between the $V_H$ and a $V_L$ and the $C_H2$ and/or $C_H3$ domains, sometimes this conformation is referred to as a Flex Minibody (Hu et al., 1996). A minibody does not comprise a $C_H1$ or a $C_L$. Preferably, the $V_H$ and $V_L$ domains are fused to the hinge region and the $C_H3$ domain of an antibody. Each of the regions may be derived from the same antibody. Alternatively, the $V_H$ and $V_L$ domains can be derived from one antibody and the hinge and $C_H2/C_H3$ from another, or the hinge and $C_H2/C_H3$ can also be derived from different antibodies. The present disclosure also contemplates a multispecific minibody which may comprise a $V_H$ and $V_L$ from one antibody and a $V_H$ and a $V_L$ from another antibody.

Exemplary minibodies and methods for their production are described, for example, in WO94/09817.

U.S. Pat. No. 5,731,168 describes molecules in which the interface between a pair of Fv is engineered to maximize the percentage of heterodimers which are recovered from recombinant cell culture to thereby produce bi-specific proteins. The preferred interface comprises at least a part of a $C_H3$ domain. In this method, one or more small amino acid side chains from the interface of the first protein are replaced with larger side chains {e.g., tyrosine or tryptophan). Compensatory "cavities" of identical or similar size to the large side chain(s) are created on the interface of the second protein by replacing large amino acid side chains with smaller ones (e.g., alanine or threonine).

Bispecific proteins which may comprise variable domains include cross-linked or "heteroconjugate" proteins. For example, one of the proteins in the heteroconjugate can be coupled to avidin and the other to biotin. Such proteins have, for example, been proposed to target immune system cells to unwanted cells (U.S. Pat. No. 4,676,980). Heteroconjugate proteins which may comprise variable domains may be made using any convenient cross-linking methods. Suitable cross-linking agents are known in the art, and are disclosed in U.S. Pat. No. 4,676,980, along with a number of cross-linking techniques.

Bispecific proteins which may comprise variable domains can also be prepared using chemical linkage. Brennan (1985) describe a procedure wherein intact antibodies are proteolytically cleaved to generate F(ab')2 fragments. These fragments are reduced in the presence of the dithiol complexing agent, sodium arsenite, to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific protein.

Additional variable domain containing proteins include, for example, single chain Fab (e.g., Hust et al., 2007) or a $Fab_3$ (e.g., as described in EP19930302894).

The present disclosure encompasses a protein which may comprise a modified $V_L$ of the disclosure and a constant region (e.g., Fc) or a domain thereof, e.g., $C_H2$ and/or $C_H3$ domain. For example, the present disclosure provides a minibody (as discussed above) or a domain antibody-Fc fusion or a scFv-Fc fusion or a diabody-Fc fusion or a triabody-Fc fusion or a tetrabody-Fc fusion or a domain antibody-$C_H2$ fusion, scFc-$C_H2$ fusion or a diabody-$C_H2$ fusion or a triabody-$C_H2$ fusion or a tetrabody-$C_H2$ fusion or a domain antibody-$C_H3$ fusion or a scFv-$C_H3$ fusion or a diabody-$C_H3$ fusion or a triabody-$C_H3$ fusion or a tetrabody-$C_H3$ fusion. Any of these proteins may comprise a linker, preferably an antibody hinge region, between the variable domain and the constant region or constant domain. Preferably, such a Fc fusion protein has effector function.

As used herein, the term "$C_H2$ domain" includes the portion of a heavy chain antibody molecule that extends, e.g., from between about positions 231-340 according to the Kabat EU numbering system (as disclosed in Kabat 1991 or 1992). Two N-linked branched carbohydrate chains are generally interposed between the two $CH_2$ domains of an intact native IgG molecule. In one example, a protein of the present disclosure may comprise a $C_H2$ domain derived from an IgG1 molecule (e.g. a human IgG1 molecule). In one example, a protein of the present disclosure may comprise a $C_H2$ domain derived from an IgG4 molecule (e.g., a human IgG4 molecule).

As used herein, the term "$C_H3$ domain" includes the portion of a heavy chain antibody molecule that extends approximately 110 residues from N-terminus of the $C_H2$ domain, e.g., from about position 341-446b (Kabat EU numbering system). The $C_H3$ domain typically forms the C-terminal portion of an IgG antibody. In some antibodies, however, additional domains may extend from $C_H3$ domain to form the C-terminal portion of the molecule (e.g. the $C_H4$ domain in the μ chain of IgM and the e chain of IgE). In one example, a protein of the present disclosure may comprise a $C_H3$ domain derived from an IgG1 molecule (e.g., a human IgG1 molecule). In another example, a protein of the present disclosure may comprise a $C_H3$ domain derived from an IgG4 molecule (e.g., a human IgG4 molecule).

Constant region sequences useful for producing the proteins of the present disclosure may be obtained from a number of different sources. In preferred examples, the constant region or portion thereof of the protein is derived from a human antibody. It is understood, however, that the constant region or portion thereof may be derived from an immunoglobulin or antibody of another mammalian species, including for example, a rodent (e.g. a mouse, rat, rabbit, guinea pig) or non-human primate (e.g. chimpanzee, macaque) species. Moreover, the constant region domain or portion thereof may be derived from any antibody class.

As used herein, the term "effector function" refers to the functional ability of the Fc region or portion thereof (e.g., $C_H2$ domain) to bind proteins and/or cells of the immune system and mediate various biological effects. Effector functions may be antigen-dependent or antigen-independent. "Antigen-dependent effector function" refers to an effector function which is normally induced following the binding of an antibody to an antigen. Typical antigen-dependent effector functions include the ability to bind a complement protein (e.g. C1q). For example, binding of the C1 component of complement to the Fc region can activate the classical complement system leading to the opsonisation and lysis of cell pathogens, a process referred to as complement-dependent cytotoxicity (CDC). The activation of complement also stimulates the inflammatory response and may also be involved in autoimmune hypersensitivity. Other antigen-dependent effector functions are mediated by the binding of antibodies, via their Fc region, to certain Fc receptors ("FcRs") on cells. There are a number of Fc receptors which are specific for different classes of antibody, including IgG (gamma receptors, or Ig$\lambda$Rs), IgE (epsilon receptors, or Ig$\epsilon$s), IgA (alpha receptors, or Ig$\alpha$Rs) and IgM ($\mu$ receptors, or Ig$\mu$Rs). Binding of antibodies to Fc receptors on cell surfaces triggers a number of important and diverse biological responses including endocytosis of immune complexes, engulfment and destruction of antibody-coated particles or microorganisms (also called antibody-dependent phagocytosis, or ADCP), clearance of immune complexes, lysis of antibody-coated target cells by killer cells (called antibody-dependent cell-mediated cytotoxicity, or ADCC), release of inflammatory mediators, regulation of immune system cell activation, placental transfer and control of antibody production.

As used herein, the term "antigen-independent effector function" refers to an effector function which may be induced by an antibody, regardless of whether it has bound its corresponding antigen. Typical antigen-independent effector functions include cellular transport, circulating half-life and clearance rates of antibodies, and facilitation of purification. A structurally unique Fc receptor, the "neonatal Fc receptor" or "FcRn", also known as the salvage receptor, plays a critical role in regulating half-life and cellular transport. Other Fc receptors purified from microbial cells (e.g. Staphylococcal Protein A or G) are capable of binding to the Fc region with high affinity and can be used to facilitate the purification of the Fc-containing protein.

Constant region domains can be cloned, e.g., using the polymerase chain reaction and primers which are selected to amplify the domain of interest. The cloning of antibody sequences is described in for example, in U.S. Pat. No. 5,658,570.

The protein of the present disclosure may comprise any number of constant regions/domains of different types.

The constant domains or portions thereof making up the constant region of an protein may be derived from different antibody molecules. For example, a protein may comprise a $C_H2$ domain or portion thereof derived from an IgG1 molecule and a $C_H3$ region or portion thereof derived from an IgG3 molecule.

In another example of the disclosure, the protein of the present disclosure may comprise at least a region of an Fc sufficient to confer FcRn binding. For example, the portion of the Fc region that binds to FcRn may comprise from about amino acids 282-438 of IgG1, according to Kabat EU numbering.

In one example, an altered protein of the present disclosure may comprise a modified constant regions wherein or more constant region domains are partially or entirely deleted ("domain-deleted constant regions"). The present disclosure also encompasses modified Fc regions or parts there having altered, e.g., improved or reduced effector function. Many such modified Fc regions are known in the art and described, for example, in WO2005/035586, WO2005/063815 or WO2005/047327.

The present disclosure also encompasses proteins which may comprise additional regions capable of inducing effector function. For example, the protein may comprise an antibody variable region capable of binding to a T cell (e.g., binding to CD4, such as a BiTE) or a NK cells (e.g., binding to CD19).

The present disclosure also contemplates a deimmunized protein. Deimmunized proteins have one or more epitopes, e.g., B cell epitopes or T cell epitopes removed (i.e., mutated) to thereby reduce the likelihood that a subject will raise an immune response against the protein. Methods for producing deimmunized proteins are known in the art and described, for example, in WO00/34317, WO2004/108158 and WO2004/064724. For example, the method may comprise performing an in silico analysis to predict an epitope in a protein and mutating one or more residues in the predicted epitope to thereby reduce its immunogenicity. The protein is then analyzed, e.g., in silico or in vitro or in vivo to ensure that it retains its ability to bind to an antigen. For example, an epitope that occurs within a CDR is not mutated unless the mutation is unlikely to reduce antigen binding. Methods for predicting epitopes are known in the art and described, for example, in Saha (2004).

Methods for introducing suitable mutations and expressing and assaying the resulting protein will be apparent to the skilled artisan based on the description herein.

The present disclosure also encompasses a library of proteins which may comprise a plurality of $V_L$s (and, optionally, $V_H$s) modified according to the present disclosure, e.g., the library may comprise a plurality of proteins having with different binding characteristics Examples of this disclosure include naïve libraries, immunized libraries or synthetic libraries. Naïve libraries are derived from B-lymphocytes of a suitable host which has not been challenged with any immunogen, nor which is exhibiting symptoms of infection or inflammation. Immunized libraries are made from a mixture of B-cells and plasma cells obtained from a suitably "immunized" host, i.e., a host that has been challenged with an immunogen. In one example, the mRNA from these cells is translated into cDNA using methods known in the art (e.g., oligo-dT primers and reverse transcriptase). In an alternative example, nucleic acids encoding antibodies from the host cells (mRNA or genomic DNA) are amplified by PCR with suitable primers. Primers for such antibody gene amplifications are known in the art (e.g., US6096551 and WO00/70023). In a further example, the mRNA from the host cells is synthesized into cDNA and these cDNAs are then amplified in a PCR reaction with antibody specific primers (e.g., U.S. Pat. No. 6,319,690). Alternatively, the repertoires may be cloned by conventional cDNA cloning technology (Sambrook and Russell, eds, Molecular Cloning: A Laboratory Manual, $3^{rd}$ Ed, vols. 1-3, Cold Spring Harbor Laboratory Press, 2001), without using PCR. The DNAs are modified to include negatively charged amino acid(s) at the requisite sites either during or following cloning.

In another example, a database of published antibody sequences of human origin is established where the antibody sequences are aligned to each other. The database is used to define subgroups of antibody sequences which show a high degree of similarity in both the sequence and the canonical fold of CDR loops (as determined by analysis of antibody structures). For each of the subgroups a consensus sequence is deduced which represents the members of this subgroup; the complete collection of consensus sequences represent therefore the complete structural repertoire of human antibodies.

These artificial genes are then constructed, e.g., by total gene synthesis or by the use of synthetic genetic subunits. These genetic subunits correspond to structural sub-elements at the polypeptide level. On the DNA level, these genetic subunits are defined by cleavage sites at the start and the end of each of the sub-elements, which are unique in the vector system. All genes which are members of the collection of consensus sequences are constructed such that they contain a similar pattern of corresponding genetic sub-sequences. For example, said polypeptides are or are derived from the HuCAL consensus genes: Vκ1, Vκ2, Vκ3, Vκ4, Vλ1, Vλ2, Vλ3, $V_H1A$, $V_H1B$, $V_H2$, $V_H3$, $V_H4$, $V_H5$, $V_H6$, Cκ, Cλ, $C_H1$ or any combination of said HuCAL consensus genes. This collection of DNA molecules can then be used to create "synthetic libraries" of antibodies, preferably Fv, disulphide-linked Fv, single-chain Fv (scFv), Fab fragments, or Fab' fragments which may be used as sources of proteins that bind specifically to an antigen. U.S. Pat. No. 6,300,064 discloses methods for making synthetic libraries. Such synthetic libraries are modified to include a negatively charged amino acid according to the present disclosure. In another example, synthetic human antibodies are made by synthesis from defined V-gene elements. Winter (EP0368684) has provided a method for amplifying (e.g., by PCR), cloning, and expressing antibody variable domain genes. Starting with these genes he was able to create libraries of functional antibody fragments by randomizing the CDR3 of the heavy and/or the light chain. This process is functionally equivalent to the natural process of VJ and VDJ recombination which occurs during the development of B-cells in the immune system. For example, repertoires of human germ line $V_H$ gene segments can be rearranged in vitro by joining to synthetic "D-segments" of five random amino acid residues and a J-segment, to create a synthetic third complementarity determining region (CDR) of eight residues. U.S. Pat. No. 5,885,793 discloses methods of making such antibody libraries such as these. As will be apparent to the skilled artisan, a library which may comprise proteins of the present disclosure is produced such that the amplified V region may comprise codons encoding a negatively charged amino acid at a position described herein.

The proteins according to the disclosure may be soluble secreted proteins or may be presented as a fusion protein on the surface of a cell, or particle (e.g., a phage or other virus, a ribosome or a spore).

Various display library formats are known in the art and reviewed, for example, in Levin and Weiss (2006). For example, the library is an in vitro display library (i.e., the proteins are displayed using in vitro display wherein the expressed domain is linked to the nucleic acid from which it was expressed such that said domain is presented in the absence of a host cell). Accordingly, libraries produced by in vitro display technologies are not limited by transformation or transfection efficiencies. Examples of methods of in vitro display include ribosome display, covalent display and mRNA display.

In one example, the in vitro display library is a ribosome display library. The skilled artisan will be aware that a ribosome display library directly links mRNA encoded by the expression library to the protein that it encodes. Means for producing a ribosome display library comprise placing nucleic acid encoding the protein which may comprise a $V_L$ (and, optionally, a $V_H$) in operable connection with an appropriate promoter sequence and ribosome binding sequence. Preferred promoter sequences are the bacteriophage T3 and T7 promoters. Preferably, the nucleic acid is placed in operable connection with a spacer sequence and a modified terminator sequence with the terminator codon removed. As used in the present context, the term "spacer sequence" shall be understood to mean a series of nucleic acids that encode a peptide that is fused to the peptide. The spacer sequence is incorporated into the gene construct, as the peptide encoded by the spacer sequence remains within the ribosomal tunnel following translation, while allowing the protein which may comprise a $V_L$ (and, optionally, a $V_H$) to freely fold and interact with another protein or a nucleic acid. A preferred spacer sequence is, for example, a nucleic acid that encodes amino acids 211-299 of gene III of filamentous phage M13 mp19.

The display library is transcribed and translated in vitro using methods known in the art and/or described for example, in Ausubel et al (1987) and Sambrook et al (2001). Examples of commercially available systems for in vitro transcription and translation include, for example, the TNT in vitro transcription and translation systems from Promega. Cooling the expression reactions on ice generally terminates translation. The ribosome complexes are stabilized against dissociation from the peptide and/or its encoding mRNA by the addition of reagents such as, for example, magnesium acetate or chloroamphenicol. Such in vitro display libraries are screened by a variety of methods, as described herein.

In another example, the display library of the present disclosure is a ribosome inactivation display library. In accordance with this example, a nucleic acid is operably linked to a nucleic acid encoding a first spacer sequence. It is preferred that this spacer sequence is a glycine/serine rich sequence that allows a protein which may comprise a $V_L$ (and, optionally, a $V_H$) encoded therefrom to freely fold and interact with a target antigen. The first spacer sequence is linked to a nucleic acid that encodes a toxin that inactivates a ribosome. It is preferred that the toxin may comprise the ricin A chain, which inactivates eukaryotic ribosomes and stalls the ribosome on the translation complex without release of the mRNA or the encoded peptide. The nucleic acid encoding the toxin is linked to another nucleic acid that encodes a second spacer sequence. The second spacer is an anchor to occupy the tunnel of the ribosome, and allow both the peptide and the toxin to correctly fold and become active. Examples of such spacer sequences are sequences derived from gene III of M13 bacteriophage. Ribosome inactivation display libraries are generally transcribed and translated in vitro, using a system such as the rabbit reticulocyte lysate system available from Promega. Upon translation of the mRNA encoding the toxin and correct folding of this protein, the ribosome is inactivated while still bound to both the encoded polypeptide and the mRNA from which it was translated.

In another example, the display library is a mRNA display library. In accordance with this example, a nucleic acid is operably linked to a nucleic acid encoding a spacer sequence, such as a glycine/serine rich sequence that allows a protein which may comprise a $V_L$ (and, optionally, a $V_H$) encoded by the expression library of the present disclosure to freely fold and interact with a target antigen. The nucleic acid encoding the spacer sequence is operably linked to a transcription terminator. mRNA display libraries are generally transcribed in vitro using methods known in the art, such as, for example, the HeLaScribe Nuclear Extract In Vitro Transcription System available from Promega. Encoded mRNA is subsequently covalently linked to a DNA oligonucleotide that is covalently linked to a molecule that binds to a ribosome, such as, for example, puromycin, using techniques known in the art and are described in, for example, Roberts and Szostak (1997). Preferably, the oligonucleotide is covalently linked to a psoralen moiety, whereby the oligonucleotide is photo-crosslinked to a mRNA encoded by the expression library of the present disclosure. The mRNA transcribed from the expression library is then translated using methods known in the art. When the ribosome reaches the junction of the mRNA and the oligonucleotide the ribosome stalls and the puromycin moiety enters the phosphotransferase site of the ribosome and thus covalently links the encoded polypeptide to the mRNA from which it was expressed.

In yet another example, the display library is a covalent display library. In accordance with this example, a nucleic acid encoding a protein which may comprise a $V_L$ (and, optionally, a $V_H$) is operably linked to a second nucleic acid that encodes a protein that interacts with the DNA from which it was encoded. Examples of a protein that interacts with the DNA from which it interacts include, but are not limited to, the *E. coli* bacteriophage P2 viral A protein (P2A) and equivalent proteins isolated from phage 186, HP1 and PSP3. A covalent display gene construct is transcribed and translated in vitro, using a system such as the rabbit reticulocyte lysate system available from Promega. Upon translation of the fusion of the protein which may comprise a $V_L$ (and, optionally, a $V_H$) and the P2A protein, the P2A protein nicks the nucleic acid to which it binds and forms a covalent bond therewith. Accordingly, a nucleic acid fragment is covalently linked to the peptide that it encodes.

In yet another example, the display library is a phage display library wherein the expressed proteins which may comprise a $V_L$ (and, optionally, a $V_H$) are displayed on the surface of a bacteriophage, as described, for example, in U.S. Pat. No. 5,821,047; U.S. Pat. No. 6,248,516 and U.S. Pat. No. 6,190,908. The basic principle described relates to the fusion of a first nucleic acid which may comprise a sequence encoding a protein which may comprise a $V_L$ (and, optionally, a $V_H$) to a second nucleic acid which may comprise a sequence encoding a phage coat protein, such as, for example a phage coat proteins selected from the group, M13 protein-3, M13 protein-7, or M13, protein-8. These sequences are then inserted into an appropriate vector, i.e., one that is able to replicate in bacterial cells. Suitable host cells, such as, for example *E. coli*, are then transformed with the recombinant vector. Said host cells are also infected with a helper phage particle encoding an unmodified form of the coat protein to which a nucleic acid fragment is operably linked. Transformed, infected host cells are cultured under conditions suitable for forming recombinant phagemid particles which may comprise more than one copy of the fusion protein on the surface of the particle. This system has been shown to be effective in the generation of virus particles such as, λ phage, T4 phage, M13 phage, T7 phage and baculovirus. Such phage display particles are then screened to identify a displayed domain having a conformation sufficient for binding to a target antigen.

Other viral display libraries include a retroviral display library wherein the expressed peptides or protein domains are displayed on the surface of a retroviral particle, e.g., as described in U.S. Pat. No. 6,297,004

The present disclosure also contemplates bacterial display libraries, e.g., as described in U.S. Pat. No. 5,516,637; yeast display libraries, e.g., as described in U.S. Pat. No. 6,423, 538 or a mammalian display library, e.g., as described in Strenglin et al 1988.

Methods for screening display libraries are known in the art. In one example, a display library of the present disclosure is screened using affinity purification. Affinity purification techniques are known in the art and are described in, for example, Scopes (1994). Methods of affinity purification typically involve contacting the proteins which may comprise a $V_L$ (and, optionally, a $V_H$) displayed by the library with a target antigen and/or a superantigen (e.g., Protein A or Protein L) and, following washing, eluting those domains that remain bound to the antigen. The antigen is preferably bound to another molecule to allow for ease of purification, such as, for example, a molecule selected from the group consisting of protein G, Sepharose, agarose, biotin, glutathione S-transferase (GST), and FLAG epitope. Accordingly, the target protein or nucleic acid is isolated simply through centrifugation, or through binding to another molecule, e.g. streptavidin, or binding of a specific antibody, e.g. anti-FLAG antibodies, or anti-GST antibodies.

In another example, the display library of the present disclosure is expressed so as to allow identification of a bound peptide using FACS analysis. The screening of libraries using FACS analysis is described in U.S. Pat. No. 645,563. For example, an in vitro display library is screened by FACS sorting. In vitro display proteins are covalently linked to a particle or bead suitable for FACS sorting, such as, for example, glass, polymers such as for example polystyrene, latex or cross-linked dextrans such as Sepharose, cellulose, nylon. Teflon, amongst others. The displayed library bound to particles or beads is added to a antigen or superantigen that has been labeled with a detectable label, such as for example a fluorescent molecule, or a molecule which is detected by a second fluorescent molecule. The beads are then washed and subjected to sorting by FACS, which allows the beads with bound fluorescent antigen or superantigen, to be separated from the beads that have not bound to a fluorescent target protein or nucleic acid.

Alternatively the library is screened using a biosensor-based assay, such as, for example, Biacore sensor chip technology (Biacore AB, UK). The Biacore sensor chip is a glass surface coated with a thin layer of gold modified with carboxymethylated dextran, to which the target protein or nucleic acid is covalently attached. The libraries of the present disclosure are then exposed to the Biacore sensor chip which may comprise the antigen.

DNA encoding a protein which may comprise a variable domain is isolated using standard methods in the art. For example, primers are designed to anneal to conserved regions within a variable domain that flank the region of interest, and those primers are then used to amplify the intervening nucleic acid, e.g., by PCR. Suitable methods and/or primers are known in the art and/or described, for example, in Borrebaeck (ed), 1995 and/or Froyen et al., 1995. Suitable sources of template DNA for such amplification methods is derived from, for example, hybridomas, transfectomas and/or cells expressing proteins which may comprise a variable domain, e.g., as described herein.

Following isolation, the DNA is modified to include codons encoding negatively charged amino acid at the requisite locations by any of a variety of methods known in the art. These methods include, but are not limited to, preparation by site-directed (or oligonucleotide-mediated) mutagenesis, PCR mutagenesis, and cassette mutagenesis of an earlier prepared DNA encoding the protein. Variants of recombinant proteins may be constructed also by restriction fragment manipulation or by overlap extension PCR with synthetic oligonucleotides. Mutagenic primers encode the negatively charged amino acids, for example include residues that make up a codon encoding a negatively charged amino acid, e.g., aspartic acid (i.e., GAA or GAG) or glutamic acid (i.e., GAT or GAC). Standard mutagenesis techniques can be employed to generate DNA encoding such mutant DNA. General guidance can be found in Sambrook et al 1989; and/or Ausubel et al 1993.

Site-directed mutagenesis is one method for preparing substitution variants, i.e. mutant proteins. This technique is known in the art (see for example, Carter et al 1985; or Ho et al 1989). Briefly, in carrying out site-directed mutagenesis of DNA, the starting DNA is altered by first hybridizing an oligonucleotide encoding the desired mutation (e.g., insertion of one or more negatively charged amino acid encoding codons) to a single strand of such starting DNA. After hybridization, a DNA polymerase is used to synthesize an entire second strand, using the hybridized oligonucleotide as a primer, and using the single strand of the starting DNA as a template. Thus, the oligonucleotide encoding the desired mutation is incorporated in the resulting double-stranded DNA. Site-directed mutagenesis may be carried out within the gene expressing the protein to be mutagenized in an expression plasmid and the resulting plasmid may be sequenced to confirm the introduction of the desired negatively charged amino acid replacement mutations. Site-directed protocols and formats include commercially available kits, e.g. QuikChange® Multi Site-Directed Mutagenesis Kit (Stratagene, La Jolla, Calif.).

PCR mutagenesis is also suitable for making amino acid sequence variants of the starting protein. See Higuchi, 1990; Ito et at 1991. Briefly, when small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template.

Another method for preparing variants, cassette mutagenesis, is based on the technique described by Wells et al, 1985. The starting material is the plasmid (or other vector) which may comprise the starting protein DNA to be mutated. The codon(s) in the starting DNA to be mutated are identified. There must be a unique restriction endonuclease site on each side of the identified mutation site(s). If no such restriction sites exist, they may be generated using the above described oligonucleotide-mediated mutagenesis method to introduce them at appropriate locations in the starting DNA. The plasmid DNA is cut at these sites to linearize it. A double-stranded oligonucleotide encoding the sequence of the DNA between the restriction sites but containing the desired mutation(s) is synthesized using standard procedures, wherein the two strands of the oligonucleotide are synthesized separately and then hybridized together using standard techniques. This double-stranded oligonucleotide is referred to as the cassette. This cassette is designed to have 5' and 3' ends that are compatible with the ends of the linearized plasmid, such that it can be directly ligated to the plasmid. This plasmid now contains the mutated DNA sequence. Mutant DNA containing the encoded negatively charged amino acid replacements can be confirmed by DNA sequencing.

Single mutations are also generated by oligonucleotide directed mutagenesis using double stranded plasmid DNA as template by PCR based mutagenesis (Sambrook et al., 2001).

In one example, if a protein of the disclosure may comprise an aspartic acid at position 50 and a glutamic acid at position 56, one or more of the following apply:
 (i) the amino acid at position 51 is not alanine;
 (ii) the amino acid at position 52 is not serine;
 (iii) the amino acid at position 53 is not asparagine or serine;
 (iv) the amino acid at position 54 is not leucine; and/or
 (v) the amino acid at position 56 is not threonine or serine.

In one example, if a protein of the disclosure may comprise an aspartic acid at position 50 and an aspartic acid at position 53, one or more of the following apply:
 (i) the amino acid at position 51 is not alanine;
 (ii) the amino acid at position 52 is not lysine;
 (iii) the amino acid at position 54 is not leucine;
 (iv) the amino acid at position 55 is not histidine; and/or
 (v) the amino acid at position 56 is not threonine or serine.

In one example, if a protein of the disclosure may comprise one negatively charged amino acid, which is at position 50 or at position 55, one or more of the following apply:
 (i) the amino acid at position 51 is not alanine;
 (ii) the amino acid at position 52 is not lysine;
 (iii) the amino acid at position 53 is not asparagine or serine or threonine;
 (iv) the amino acid at position 54 is not leucine or arginine or tryptophan or lysine; and/or
 (v) the amino acid at position 56 is not threonine or serine or phenylalanine.

In one example, a protein of the disclosure does not comprise one or more (e.g., two or three or four) FRs or is not derived from or based on a human germiline Vκ segment selected from the group consistsing of O8, O18, L18, L4, L12, L22, A2, DPK14, A17, A1, A11, L20, L6 and B3.

In one example, a protein of the disclosure which may comprise two or more negatively charged amino acids does not comprise one or more (e.g., two or three or four) FRs or is not derived from or based on a human germiline Vκ segment selected from the group consistsing of O8, O18, L18, L4, L2 and L22.

In one example, a protein of the disclosure does not comprise a fully human CDR2 of $V_L$. By "fully human CDR2 of $V_L$" will be understood to mean that the CDR2 can be from a species other than human or can be synthetic or can be a mutant form of a human CDR2, e.g., produced by affinity maturation.

In the case of a recombinant protein, nucleic acid encoding same is preferably placed into expression vectors, which are then transfected into host cells, preferably cells that can produce a disulphide bridge or bond, such as *E. coli* cells, yeast cells, insect cells, or mammalian cells, such as simian COS cells, Chinese Hamster Ovary (CHO) cells, or myeloma cells that do not otherwise produce immunoglobulin protein, to obtain the synthesis of proteins in the recombinant host cells. Review articles on recombinant expression in bacteria of DNA encoding antibodies include Skerra et al, (1993) and Plückthun, (1992). Molecular cloning techniques to achieve these ends are known in the art and described, for example in Ausubel et al (1987) and Sambrook et al (2001).

A wide variety of cloning and in vitro amplification methods are suitable for the construction of recombinant nucleic acids. Methods of producing recombinant antibodies are also known in the art. See U.S. Pat. No. 4,816,567.

Following isolation, the nucleic acid encoding a protein of the present disclosure is preferably inserted into an expression construct or replicable vector for further cloning (amplification of the DNA) or for expression in a cell-free system or in cells. Preferably, the nucleic acid is operably linked to a promoter, As used herein, the term "promoter" is to be taken in its broadest context and includes the transcriptional regulatory sequences of a genomic gene, including the TATA box or initiator element, which is required for accurate transcription initiation, with or without additional regulatory elements (e.g., upstream activating sequences, transcription factor binding sites, enhancers and silencers) that alter expression of a nucleic acid, e.g., in response to a developmental and/or external stimulus, or in a tissue specific manner. In the present context, the term "promoter" is also used to describe a recombinant, synthetic or fusion nucleic acid, or derivative which confers, activates or enhances the expression of a nucleic acid to which it is operably linked. Preferred promoters can contain additional copies of one or more specific regulatory elements to further enhance expression and/or alter the spatial expression and/or temporal expression of said nucleic acid.

As used herein, the term "operably linked to" means positioning a promoter relative to a nucleic acid such that expression of the nucleic acid is controlled by the promoter.

Cell free expression systems are also contemplated by the present disclosure. For example, a nucleic acid encoding a protein of the present disclosure is operably linked to a suitable promoter, e.g., a T7 promoter, and the resulting expression construct exposed to conditions sufficient for transcription and translation. Typical expression vectors for in vitro expression or cell-free expression have been described and include, but are not limited to the TNT T7 and TNT T3 systems (Promega), the pEXP1-DEST and pEXP2-DEST vectors (Invitrogen).

Many vectors for expression in cells are available. The vector components generally include, but are not limited to, one or more of the following: a signal sequence, a sequence encoding protein of the present disclosure (e.g., derived from the information provided herein), an enhancer element, a promoter, and a transcription termination sequence. The skilled artisan will be aware of suitable sequences for expression of a protein. For example, exemplary signal sequences include prokaryotic secretion signals (e.g., pelB, alkaline phospholipase, penicillinase, Ipp, or heat-stable enterotoxin II), yeast secretion signals (e.g., invertase leader, α factor leader, or acid phosphatase leader) or mammalian secretion signals (e.g., herpes simplex gD signal).

Exemplary promoters include those active in prokaryotes (e.g., phoA promoter, β-lactamase and lactose promoter systems, alkaline phosphatase, a tryptophan (trp) promoter system, and hybrid promoters such as the tac promoter). These promoter are useful for expression in prokaryotes including eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis, Pseudomonas* such as *P. aeruginosa*, and *Streptomyces*. Preferably, the host is *E. coli*. One preferred *E. coli* cloning host is *E. coli* 294 (ATCC 31,446), although other strains such as *E. coli* B, *E. coli* X 1776 (ATCC 31,537), and *E. coli* W3110 (ATCC 27,325), DH5α or DH10B are suitable.

Exemplary promoters active in mammalian cells include cytomegalovirus immediate early promoter (CMV-IE), human elongation factor 1-α promoter (EF1), small nuclear RNA promoters (U1a and U1b), α-myosin heavy chain promoter, Simian virus 40 promoter (SV40), Rous sarcoma virus promoter (RSV), Adenovirus major late promoter, β-actin promoter, hybrid regulatory element which may comprise a CMV enhancer/β-actin promoter or an immunoglobulin promoter or active fragment thereof. Examples of useful mammalian host cell lines are monkey kidney CV line transformed by SV40 (COS-7, ATCC CRL 1651); human embryonic kidney line (293 or 293 cells subcloned for growth in suspension culture; baby hamster kidney cells (BHK, ATCC CCL 10); or Chinese hamster ovary cells (CHO).

Typical promoters suitable for expression in yeast cells such as for example a yeast cell selected from the group which may comprise *Pichia pastoris, Saccharomyces cerevisiae* and *S. pombe*, include, but are not limited to, the ADH1 promoter, the GAL1 promoter, the GAL4 promoter, the CUP1 promoter, the PHO5 promoter, the nmt promoter, the RPR1 promoter, or the TEF1 promoter.

Typical promoters suitable for expression in insect cells include, but are not limited to, the OPEI2 promoter, the insect actin promoter isolated from *Bombyx muri*, the *Drosophila* sp. Dsh promoter (Marsh et al 2000) and the inducible metallothionein promoter. Preferred insect cells for expression of recombinant proteins include an insect cell selected from the group which may comprise, BT1-TN-5B1-4 cells, and *Spodoptera frugiperda* cells (e.g., sf19 cells, sf21 cells). Suitable insects for the expression of the nucleic acid fragments include but are not limited to *Drosophila* sp. The use of *S. frugiperda* is also contemplated.

Means for introducing the isolated nucleic acid molecule or a gene construct which may comprise same into a cell for expression are known to those skilled in the art. The technique used for a given cell depends on the known successful techniques. Means for introducing recombinant DNA into cells include microinjection, transfection mediated by DEAE-dextran, transfection mediated by liposomes such as by using lipofectamine (Gibco, Md., USA) and/or cellfectin (Gibco, Md., USA), PEG-mediated DNA uptake, electroporation and microparticle bombardment such as by using DNA-coated tungsten or gold particles (Agracetus Inc., WI, USA) amongst others.

The host cells used to produce the protein of this disclosure may be cultured in a variety of media, depending on the cell type used. Commercially available media such as Ham's F10 (Sigma), Minimal Essential Medium ((MEM), (Sigma), RPM1-1640 (Sigma), and Dulbecco's Modified Eagle's Medium ((DMEM), Sigma) are suitable for culturing mammalian cells. Media for culturing other cell types discussed herein are known in the art.

A protein of the present disclosure is preferably isolated, engineered or non-naturally occurring. By "isolated, engineered or non-naturally occurring" is meant that the protein is substantially purified or is removed from its naturally-occurring environment, e.g., is in a heterologous environment. By "substantially purified" is meant the protein is substantially free of contaminating agents, e.g., at least about 70% or 75% or 80% or 85% or 90% or 95% or 96% or 97% or 98% or 99% free of contaminating agents.

Methods for purifying a protein of the present disclosure are known in the art and/or described herein. For example, the protein is contacted with an agent capable of binding thereto for a time and under conditions sufficient for binding to occur. Optionally, following washing to remove unbound protein, the protein of the present disclosure is isolated, e.g., eluted.

When using recombinant techniques, the protein of the present disclosure can be produced intracellularly, in the periplasmic space, or directly secreted into the medium. If the protein is produced intracellularly, as a first step, the particulate debris, either host cells or lysed fragments, is removed, for example, by centrifugation or ultrafiltration. Carter et al. (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the protein is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The protein prepared from the cells can be purified using, for example, hydroxyl apatite chromatography, gel electrophoresis, dialysis, and affinity chromatography, with affinity chromatography being the preferred purification technique. The suitability of protein A as an affinity ligand depends on the species and isotype of any antibody Fc domain that is present in the protein (if present at all). Protein A can be used to purify antibodies that are based on human γ1, γ2, or γ4 heavy chains (Lindmark et al. 1983). Protein G is recommended for all mouse isotypes and for human γ3 (Guss et al. 1986). Otherwise affinity purification can be performed using the antigen or epitopic determinant to which a variable domain in a protein of the present disclosure binds or was raised. The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the protein to be recovered.

The skilled artisan will also be aware that a protein of the present disclosure can be modified to include a tag to facilitate purification or detection, e.g., a poly-histidine tag, e.g., a hexa-histidine tag, or a influenza virus hemagglutinin (HA) tag, or a Simian Virus 5 (V5) tag, or a FLAG tag, or a glutathione S-transferase (GST) tag. Preferably, the tag is a hexa-his tag. The resulting protein is then purified using methods known in the art, such as, affinity purification. For example, a protein which may comprise a hexa-his tag is purified by contacting a sample which may comprise the protein with nickel-nitrilotriacetic acid (Ni-NTA) that specifically binds a hexa-his tag immobilised on a solid or semi-solid support, washing the sample to remove unbound protein, and subsequently eluting the bound protein. Alternatively, or in addition a ligand or antibody that binds to a tag is used in an affinity purification method.

Following any preliminary purification step(s), the mixture which may comprise the protein of the present disclosure and contaminants may be subjected to low pH hydrophobic interaction chromatography.

A protein of the present disclosure is readily synthesized from its determined amino acid sequence using standard techniques, e.g., using BOC or FMOC chemistry. Synthetic peptides are prepared using known techniques of solid phase, liquid phase, or peptide condensation, or any combination thereof, and can include natural and/or unnatural amino acids. Amino acids used for peptide synthesis may be standard Boc (Nα-amino protected Nα-t-butyloxycarbonyl) amino acid resin with the deprotecting, neutralization, coupling and wash protocols of the original solid phase procedure of Merrifield, 1963, or the base-labile Nα-amino protected 9-fluorenylmethoxycarbonyl (Fmoc) amino acids described by Carpino and Han, 1972. Both Fmoc and Boc Nα-amino protected amino acids can be obtained from various commercial sources, such as, for example, Fluka, Bachem, Advanced Chemtech, Sigma, Cambridge Research Biochemical, Bachem, or Peninsula Labs.

The aggregation-resistance of the proteins or compositions of the disclosure can be analyzed using methods known in the art. Aggregation-resistance parameters acceptable to those in the art may be employed. Exemplary parameters are described in more detail below. In some examples, thermal refoldability is evaluated. In some examples, the expression levels (e.g., as measured by % yield) of the protein of the present disclosure are evaluated. In other examples, the aggregation levels of the proteins of the present disclosure are evaluated. In certain examples, the aggregation-resistance of a protein or composition of the disclosure is compared with that of a suitable control.

The aggregation-resistance of a protein of the present disclosure may be analyzed using a number of non-limiting biophysical or biochemical techniques known in the art. An example of such a technique is analytical spectroscopy, such as Circular Dichroism (CD) spectroscopy. CD spectroscopy measures the optical activity of a protein as a function of increasing temperature. Circular dichroism (CD) spectroscopy measures differences in the absorption of left-handed polarized light versus right-handed polarized light which arise due to structural asymmetry. A disordered or unfolded structure results in a CD spectrum very different from that of an ordered or folded structure. The CD spectrum reflects the sensitivity of the proteins to the denaturing effects of increasing temperature and is therefore indicative of a protein's aggregation-resistance (see van Mierlo and Steemsma, 2000).

Another exemplary analytical spectroscopy method for measuring aggregation-resistance is Fluorescence Emission Spectroscopy (see van Mierlo and Steemsma, supra). Yet another exemplary analytical spectroscopy method for measuring aggregation-resistance is Nuclear Magnetic Resonance (NMR) spectroscopy (see, e.g. van Mierlo and Steemsma, supra).

In other examples, the aggregation-resistance of a composition or protein of the present disclosure is measured biochemically. An exemplary biochemical method for assessing aggregation-resistance is a thermal challenge assay. In a "thermal challenge assay", a protein of the present disclosure is subjected to a range of elevated temperatures for a set period of time. For example, a test protein or is subject to a range of increasing temperatures. The activity of the protein is then assayed by a relevant biochemical assay. For example, the binding activity of the binding protein may be determined by a functional or quantitative ELISA. Another method for determining binding affinity employs surface plasmon resonance. Surface plasmon resonance is an optical phenomenon that allows for the analysis of real-time bispecific interactions by detection of alterations in protein concentrations within a biosensor matrix, for example using the BIAcore system (Pharmacia Biosensor AB, Uppsala, Sweden and Piscataway, N.J.).

In other examples, the aggregation-resistance of a composition or protein of the present disclosure is determined by measuring its propensity to aggregate. Aggregation can be measured by a number of non-limiting biochemical or biophysical techniques. For example, the aggregation of a composition or protein of the present disclosure may be evaluated using turbidity measurements. For this purpose, absorbance at 320 nm or alternatively at 330 nm, 340 nm or 350 nm is monitored.

Alternatively, or additionally, aggregation-resistance of a composition or protein can be evaluated using chromatography, e.g. Size-Exclusion Chromatograpy (SEC). SEC separates molecules on the basis of size. A column is filled with semi-solid beads of a polymeric gel that will admit ions and small molecules into their interior but not large ones. When a protein or composition is applied to the top of the column, the compact folded proteins (i.e., non-aggregated proteins) are distributed through a larger volume of solvent than is available to the large protein aggregates. Consequently, the large aggregates move more rapidly through the column, and in this way the mixture can be separated or fractionated into its components. Each fraction can be separately quantified (e.g. by light scattering) as it elutes from the gel. Accordingly, the percentage aggregation of a protein or composition of the disclosure can be determined by comparing the concentration of a fraction with the total concentration of protein applied to the gel. Aggregation-resistant compositions elute from the column as essentially a single fraction and appear as essentially a single peak in the elution profile or chromatogram.

In other examples, the aggregation-resistance of a composition of the disclosure is evaluated by measuring the amount of protein that is recovered (herein the "% yield") following expression (e.g. recombinant expression) of the protein. For example, the % yield can be measured by determining milligrams of protein recovered for every ml of host culture media (e.g., mg/ml of protein). In a preferred example, the % yield is evaluated following expression in a mammalian host cell (e.g. a CHO cell).

In yet another example, the aggregation-resistance of a composition of the disclosure is evaluated by monitoring the loss of protein at a range of temperatures (e.g. from about 25° C. to about 80° C.) following storage for a defined time period. The amount or concentration of recovered protein can be determined using any protein quantification method known in the art, and compared with the initial concentration of protein. Exemplary protein quantification methods include SDS-PAGE analysis or the Bradford assay.

In yet other examples, the aggregation-resistance of a protein of the present disclosure may be assessed by quantifying the binding of a labeled compound to denatured or unfolded portions of a binding molecule. Such molecules are preferably hydrophobic, as they preferably bind or interact with large hydrophobic patches of amino acids that are normally buried in the interior of the native protein, but which are exposed in a denatured or unfolded binding molecule. An exemplary labeled compound is the hydrophobic fluorescent dye, 1-anilino-8-naphthaline sulfonate (ANS).

Other examples, involve detecting binding of a protein that only binds to a correctly folded variable domain (e.g., Protein A binds to correctly folded IgG3 $V_H$)

The present disclosure also provides proteins of the present disclosure conjugated to another compound, e.g., a conjugate (immunoconjugate) which may comprise a protein of the present disclosure conjugated to a distinct moiety, e.g., a therapeutic agent which is directly or indirectly bound to the protein. Examples of other moieties include, but are not limited to, an enzyme, a fluorophophore, a cytotoxin, a radioisotope (e.g., iodine-131, yttrium-90 or indium-111), an immunomodulatory agent, an anti-angiogenic agent, an anti-neovascularization and/or other vascularization agent, a toxin, an anti-proliferative agent, a pro-apoptotic agent, a chemotherapeutic agent and a therapeutic nucleic acid.

A cytotoxin includes any agent that is detrimental to (e.g., kills) cells. For a description of these classes of drugs which are known in the art, and their mechanisms of action, see Goodman et al. (1990). Additional techniques relevant to the preparation of antibody immunotoxins are provided in for instance U.S. Pat. No. 5,194,594. Exemplary toxins include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin and the tricothecenes. See, for example, WO93/21232.

Suitable therapeutic agents for forming immunoconjugates of the present disclosure include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin, antimetabolites (such as methotrexate, 6-mercaptopurine, 6-thioguanine, cytarabine, fludarabin, 5-fluorouracil, decarbazine, hydroxyurea, asparaginase, gemcitabine, cladribine), alkylating agents (such as mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C, cisplatin and other platinum derivatives, such as carboplatin), antibiotics (such as dactinomycin (formerly actinomycin), bleomycin, daunorubicin (formerly daunomycin), doxorubicin, idarubicin, mithramycin, mitomycin, mitoxantrone, plicamycin, anthramycin (AMC)).

A variety of radionuclides are available for the production of radioconjugated antibodies. Examples include, but are not limited to, $^{212}Bi$, $^{131}I$, $^{90}Y$, and $^{186}Re$.

In another example, the protein may be conjugated to a "receptor" (such as streptavidin) for utilization in pretargeting wherein the protein-receptor conjugate is administered to the patient, followed by removal of unbound conjugate from the circulation using a clearing agent and then administration of a "ligand" (e.g., avidin) that is conjugated to a therapeutic agent (e.g., a radionucleotide).

The proteins of the present disclosure can be further modified to contain additional nonproteinaceous moieties that are known in the art and readily available. Preferably, the moieties suitable for derivatization of the protein are water soluble polymers. Non-limiting examples of water soluble polymers include, but are not limited to, polyethylene glycol (PEG), copolymers of ethylene glycol/propylene glycol, carboxymethylcellulose, dextran or polyvinyl alcohol.

Various methods are known in the art for conjugating a compound to a protein residue are known in the art and will be apparent to the skilled artisan.

The proteins of the present disclosure are useful in a variety of applications, including research, diagnostic/prognostic, industrial and therapeutic applications. Depending on the antigen to which the protein binds it may be useful for delivering a compound to a cell, e.g., to kill the cell or prevent growth and/or for imaging and/or for in vitro assays. In one example, the protein is useful for both imaging and delivering a cytotoxic agent to a cell, i.e., it is conjugated to a detectable label and a cytotoxic agent or a composition may comprise a mixture of proteins some of which are conjugated to a cytotoxic agent and some of which are conjugated to a detectable label.

The proteins described herein can also act as antagonists to inhibit (which can be reducing or preventing) (a) binding (e.g., of a ligand, an inhibitor) to a receptor, (b) a receptor signalling function, and/or (c) a stimulatory function. Proteins which act as antagonists of receptor function can block ligand binding directly or indirectly (e.g., by causing a conformational change).

A protein of the present disclosure may also be an agonist of a receptor, e.g., (a) enhancing or inducing binding (e.g., of a ligand) to a receptor, (b) enhancing or inducing receptor signalling function, and/or (c) providing a stimulatory function.

The present disclosure contemplates a protein which may comprise at least one $V_L$ (and optionally a $V_H$) modified according to the present disclosure capable of specifically binding to any antigen(s) other than those specifically excluded in any example, example or claim herein, i.e., an example of the disclosure is generic as opposed to requiring a specific antigen.

In one example, the protein of the present disclosure does not bind to a protein from a microorganism and/or from an avian.

In one example, the protein does not bind to lysozyme (e.g., hen egg lysozyme) and/or beta-galactosidase and/or amylase (e.g., alpha amylase) and/or anhydrase (e.g., carbonic anhydrase) and or B5R (e.g., from *Vaccinia*). In one example the protein does not bind to human albumin. In one example, the protein does not binds to human VEGF.

Exemplary proteins bind specifically to a human protein or are derived from antibodies raised against a human protein.

Examples of the present disclosure contemplate a protein that specifically binds to an antigen associated with a disease or disorder (i.e., a condition) e.g., associated with or expressed by a cancer or cancerous/transformed cell and/or associated with an autoimmune disease and/or associated with an inflammatory disease or condition and/or associated with a neurodegenerative disease and/or associated with an immune-deficiency disorder.

Exemplary antigens against which a protein of the present disclosure can be produced include BMPRIB (bone morphogenetic protein receptor-type IB; WO2004063362); E16 (LAT1, SLC7A5, WO2004048938); STEAP1 (six transmembrane epithelial antigen of prostate, WO2004065577); CA125 (MUC16, WO2004045553); MPF (MSLN, SMR, megakaryocyte potentiating factor, mesothelin, WO2003101283); Napi3b (WO2004022778); Sema 5b (WO2004000997); PSCA (US2003129192); ETBR (WO2004045516); MSG783 (WO2003104275); STEAP2 (WO2003087306); TrpM4 (US2003143557); CRIPTO (US2003224411); CD21 (WO2004045520); CD79b (WO2004016225); SPAPIB (WO2004016225); HER2 (WO2004048938); NCA (WO2004063709); MDP (WO2003016475); IL-20Rα (EP1394274); Brevican (US2003186372); EphB2R (WO2003042661); ASLG659 (US20040101899); PSCA (WO2004022709); GEDA (WO2003054152); BAFF-R (WO2004058309); CD22 (WO2003072036); CD79a (WO2003088808); CXCR5 (WO2004040000); HLA-DOB (WO9958658); P2X5 (WO2004047749); CD72 (WO2004042346); LY64 (US2002193567); FcRH1 (WO2003077836); IRTA2 (WO2003077836); TENB2 (WO2004074320); CD20 (WO94/11026); VEGF-A (Presta et al., 1997); p53; EGFR; progesterone receptor; cathepsin D; Bcl-2; E cadherin; CEA; Lewis X; Ki67; PCNA; CD3; CD4; CD5; CD7; CD11c; CD11d; c-Myc; tau; PrPSC; TNFα; sonic hedgehog; hepatocyte growth factor; hepatocyte growth factor receptor, EPHA2; prolactin receptor; prolactin; IL-2; TNF-Receptor; IL-21; IL-21 Receptor; CXCR7; FGFR2; FGF2 or Aβ.

In another example, a protein of the present disclosure binds to a soluble protein, preferably a soluble protein that is secreted in vivo. Exemplary soluble proteins include cytokines. The term "cytokine" is a generic term for proteins or peptides released by one cell population which act on another cell as intercellular mediators. Examples of cytokines include lymphokines, monokines, growth factors and traditional polypeptide hormones. Included among the cytokines are growth hormones such as human growth hormone, N-methionyl human growth hormone, and bovine growth hormone; parathyroid hormone, thyroxine, insulin, proinsulin, relaxin, prorelaxin, glycoprotein hormones such as follicle stimulating hormone (FSH), thyroid stimulating hormone (TSH) and luteinizing hormone (LH), hepatic growth factor, prostaglandin, fibroblast growth factor, prolactin, placental lactogen, OB protein, tumor necrosis factor-α and -β; mullerian-inhibiting substance, gonadotropin-associated peptide, inhibin, activin, vascular endothelial growth factor, integrin, thrombopoietin (TPO), nerve growth factors such as NGF-B, platelet-growth factor, transforming growth factors (TGFs) such as TGF-α and TGF-β, insulin-like growth factor-I or -II, erythropoietin (EPO), osteoinductive factors, interferons such as interferon-α, -β, or -γ; colony stimulating factors (CSFs) such as macrophage-CSF (M-CSF), granulocyte-macrophage-CSF (GM-CSF); and granulocyte-CSF (G-CSF), interleukins (Ils) such as IL-1, IL-1α, IL-2, IL-3, IL-4, IL-5, IL-6, IL-7, IL-8, IL-9, IL-10, IL-11, IL-12; IL-13, IL-14, IL-15, IL-16, IL-17, IL-18, IL-21 and LIF. Exemplary cytokines are selected from the group consisting of Interleukin 2, 13 or 21, TNF alpha, TGF beta, BAFF and GM-CSF.

In another example, a soluble protein is a chemokine. Chemokines generally act as chemoattractants to recruit immune effector cells to the site of chemokine expression. Chemokines include, but are not limited to, RANTES, MCAF, MIP1-alpha or MIP1-Beta. The skilled artisan will recognize that certain cytokines are also known to have chemoattractant effects and could also be classified under the term chemokines. A preferred chemokine is RANTES.

In another example, a soluble protein is a peptide hormone. Exemplary peptide hormones include insulin, NPY, PYY, glucagon and prolactin.

In a further example, a soluble protein is a protease. Exemplary proteases include Factor X, Factor VII, Factor IX or kallikrein.

In another example, a protein of the present disclosure binds to a receptor or a membrane associated protein. Exemplary antigens include, G-protein coupled receptors (such as, CXCR7, CXCR5, CXCR3, C5aR or beta-2-adrenergic receptor) or an ion-channel (such as, a sodium channel or a potassium channel or a calcium channel, preferably, Nicotinic acetylcholine receptor) or a single-span membrane protein (such as a T-cell receptor or a prolactin receptor or a cytokine receptor (e.g., an IL-21-receptor) or a MHC class 1 or a MHC class 2 or CD4 or CD8).

In a further example, a protein of the present disclosure binds to one or more of interferon alpha receptor 1 (IF-NAR1), angiopietin-2, IL-4Rα, IL-33, CXCL13, receptor for advanced glycation end products (RAGE), ICOS, IgE, interferon α, IL-6, IL-6 receptor, EphB4, CD19, GM-CSF receptor, CD22, IL-22, EphA2, IL-13, high mobility group protein 1 (HMG1), anaplastic lymphoma kinase (ALK), an integrin (e.g., Integrin αVβ3), Eph receptor, IL-9, EphA4, PC-cell-derived growth factor (PCDGF), nerve growth factor (NGF), insulin-like growth factor (IGF), platelet-derived growth factor (PDGF), platelet-derived growth factor receptor (PDGFR e.g., PDGFRα or PDGFRβ) or IL-5.

Exemplary antibodies from which a protein of the present disclosure can be derived will be apparent to the skilled artisan and include those listed hereinabove.

Exemplary bispecific proteins may bind to two different epitopes of the antigen of interest. Other such proteins may combine one antigen binding site with a binding site for another protein. Alternatively, an anti-antigen of interest region may be combined with a region which binds to a triggering molecule on a leukocyte such as a T-cell receptor molecule (e.g., CD3), or Fc receptors for IgG (FcγR), such as FcγRI (CD64), FcγRII (CD32) and/or FcγRIII (CD16), so as to focus and localize cellular defense mechanisms to the cells expressing the antigen of interest. Bispecific proteins may also be used to localize cytotoxic agents to cells which express the antigen of interest. These proteins possess a region that binds the antigen of interest and a region which binds the cytotoxic agent (e.g., saporin, anti-interferon-α, vinca alkaloid, ricin A chain, methotrexate or radioactive isotope hapten). WO 96/16673 describes a bispecific anti-ErbB2/anti-FcγRIII antibody and U.S. Pat. No. 5,837,234 discloses a bispecific anti-ErbB2/anti-FcγRI antibody. A bispecific anti-ErbB2/Fcα antibody is shown in WO98/02463. U.S. Pat. No. 5,821,337 teaches a bispecific anti-ErbB2/anti-CD3 antibody.

The proteins of the present disclosure (syn. Active ingredients) are useful for parenteral, topical, oral, or local administration, aerosol administration, or transdermal administration for prophylactic or for therapeutic treatment. The pharmaceutical compositions can be administered in a variety of unit dosage forms depending upon the method of administration. For example, unit dosage forms suitable for oral administration include powder, tablets, pills, capsules and lozenges or by parenteral administration. It is recognized that the pharmaceutical compositions of this disclosure, when administered orally, should be protected from digestion. This is typically accomplished either by complexing the proteins with a composition to render it resistant to acidic and enzymatic hydrolysis or by packaging the compound in an appropriately resistant carrier such as a liposome. Means of protecting proteins from digestion are known in the art.

Typically, a therapeutically effective amount of the protein will be formulated into a composition for administration to a subject. The phrase "a therapeutically effective amount" refers to an amount sufficient to promote, induce, and/or enhance treatment or other therapeutic effect in a subject. As will be apparent, the concentration of proteins of the present disclosure in these formulations can vary widely, and will be selected primarily based on fluid volumes, viscosities, body weight and the like in accordance with the particular mode of administration selected and the patient's needs. Depending on the type and severity of the disease, a therapeutically effective amount may be about 1 µg/kg to 100 mg/kg (e.g. for 0.1-10 mg/kg) of protein, whether, for example, by one or more separate administrations, or by continuous infusion. A typical daily dosage might range from about 1 µg/kg to 100 mg/kg or more. For repeated administrations over several days or longer, depending on the condition, the treatment is sustained until a desired suppression of disease symptoms occurs. An exemplary dosing regimen may comprise administering an initial loading dose of about 4 mg/kg, followed by a weekly maintenance dose of about 2 mg/kg of the protein. Other dosage regimens may be useful. For example, an anti-CD20 antibody such as rituximab is administered at a dose of about 375 mg/m$^2$. An anti-VEGF antibody such as bevacizumabis administered at a dose of 5-10 mg/kg. An anti-Her2/neu antibody such as trastuzumab is administered at a loading dose of 4-8 mg/kg and a weekly/fortnightly maintenance dose of 2-6 mg/kg. An anti-TNFα antibody such as adalimumab is administered at a dose of about 400 mg per week to treat rheumatoid arthritis, or at a loading dose of 160 mg for the first week and a maintenance dose of 40 mg per week, or for psoriasis a loading dose of 80 mg and a maintenance dose of 40 mg per week. The progress of therapy is easily monitored by conventional techniques and assays.

Suitable dosages of proteins of the present disclosure will vary depending on the specific protein, the condition to be diagnosed/treated/prevented and/or the subject being treated. It is within the ability of a skilled physician to determine a suitable dosage, e.g., by commencing with a sub-optimal dosage and incrementally modifying the dosage to determine an optimal or useful dosage. Alternatively, to determine an appropriate dosage for treatment/prophylaxis, data from cell culture assays or animal studies are used, wherein a suitable dose is within a range of circulating concentrations that include the ED50 of the active compound with little or no toxicity. The dosage may vary within this range depending upon the dosage form employed and the route of administration utilized. A therapeutically/prophylactically effective dose can be estimated initially from cell culture assays. A dose may be formulated in animal models to achieve a circulating plasma concentration range that includes the IC50 (i.e., the concentration of the compound which achieves a half-maximal inhibition of symptoms) as determined in cell culture. Such information can be used to more accurately determine useful doses in humans. Levels in plasma maybe measured, for example, by high performance liquid chromatography.

Alternatively, the protein of the present disclosure is formulated at a concentrated dose that is diluted to a therapeutically effective dose prior to administration to a subject.

The compositions of this disclosure are particularly useful for parenteral administration, e.g., formulated for injection via the intravenous, intramuscular, sub-cutaneous, transdermal, or other such routes, including peristaltic administration and direct instillation into a tumour or disease site (intracavity administration). The compositions for administration will commonly comprise a solution of the proteins of the present disclosure dissolved in a pharmaceutically acceptable carrier, preferably an aqueous carrier. A variety of aqueous carriers can be used, e.g., buffered saline and the like. Other exemplary carriers include water, saline, Ringer's solution, dextrose solution, and 5% human serum albumin. Nonaqueous vehicles such as mixed oils and ethyl oleate may also be used. Liposomes may also be used as carriers. The vehicles may contain minor amounts of additives that enhance isotonicity and chemical stability, e.g., buffers and preservatives. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like.

Techniques for preparing pharmaceutical compositions are generally known in the art as exemplified by Remington's Pharmaceutical Sciences, 16$^{th}$ Ed. Mack Publishing Company, 1980.

WO2002/080967 describes compositions and methods for administering aerosolized compositions which may comprise proteins for the treatment of, e.g., asthma, which are also suitable for administration of protein of the present disclosure.

A protein of the present disclosure may be combined in a pharmaceutical combination, formulation, or dosing regimen as combination therapy, with a second compound. The second compound of the pharmaceutical combination formulation or dosing regimen preferably has complementary activities to the protein of the combination such that they do not adversely affect each other.

The second compound may be a chemotherapeutic agent, cytotoxic agent, cytokine, growth inhibitory agent, antihormonal agent, and/or cardioprotectant. Such molecules are suitably present in combination in amounts that are effective for the purpose intended. A pharmaceutical composition containing a protein of the present disclosure may also have a therapeutically effective amount of a chemotherapeutic agent such as a tubulin-forming inhibitor, a topoisomerase inhibitor, or a DNA binder.

Pharmaceutical "slow release" capsules or compositions may also be used. Slow release formulations are generally designed to give a constant drug level over an extended period and may be used to deliver compounds of the present disclosure.

The present disclosure also provides a method of treating or preventing a condition in a subject, the method which may comprise administering a therapeutically effective amount of a protein of the present disclosure to a subject in need thereof.

As used herein, the terms "preventing", "prevent" or "prevention" in the context of preventing a condition include administering an amount of a protein described herein sufficient to stop or hinder the development of at least one symptom of a specified disease or condition.

As used herein, the terms "treating", "treat" or "treatment" include administering a therapeutically effective amount of an inhibitor(s) and/or agent(s) described herein sufficient to reduce or eliminate at least one symptom of a specified disease or condition.

As used herein, the term "subject" shall be taken to mean any animal including humans, preferably a mammal. Exemplary subjects include but are not limited to humans, primates, livestock (e.g. sheep, cows, horses, donkeys, pigs), companion animals (e.g. dogs, cats), laboratory test animals (e.g. mice, rabbits, rats, guinea pigs, hamsters), captive wild animals (e.g. fox, deer). Preferably the mammal is a human or primate. More preferably the mammal is a human.

As used herein, a "condition" is a disruption of or interference with normal function, and is not to be limited to any specific condition, and will include diseases or disorders. In an example, the condition is a cancer or an autoimmune or inflammatory disorder.

Exemplary cancers include, but are not limited to, carcinoma, lymphoma, blastoma, sarcoma, and leukemia or lymphoid malignancies. More particular examples of such cancers include blood cancers (e.g., lymphoma or leukemia), squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer. For example, a cancer is breast cancer or lung cancer or ovarian cancer or prostate cancer.

Inflammatory or autoimmune conditions are conditions caused by the reactions of immunoglobulins or T cell receptors to antigens. These conditions include autoimmune diseases and hypersensitivity responses (e.g. Type I: anaphylaxis, hives, food allergies, asthma; Type II: autoimmune haemolytic anaemia, blood transfusion reactions; Type III: serum sickness, necrotizing vasculitis, glomerulonephritis, rheumatoid arthritis, lupus; Type IV: contact dermatitis, graft rejection). Autoimmune diseases include rheumatologic disorders (such as, for example, rheumatoid arthritis. Sjogren's syndrome, scleroderma, lupus such as SLE and lupus nephritis, polymyositis/dermatomyositis, cryoglobulinemia, anti-phospholipid antibody syndrome, and psoriatic arthritis), osteoarthritis, autoimmune gastrointestinal and liver disorders (such as, for example, inflammatory bowel diseases (e.g., ulcerative colitis and Crohn's disease), autoimmune gastritis and pernicious anemia, autoimmune hepatitis, primary biliary cirrhosis, primary sclerosing cholangitis, and celiac disease), vasculitis (such as, for example, ANCA-associated vasculitis, including Churg-Strauss vasculitis, Wegener's granulomatosis, and polyarteriitis), autoimmune neurological disorders (such as, for example, multiple sclerosis, opsoclonus myoclonus syndrome, myasthenia gravis, neuromyelitis optica, and autoimmune polyneuropathies), renal disorders (such as, for example, glomerulonephritis. Goodpasture's syndrome, and Berger's disease), autoimmune dermatologic disorders (such as, for example, psoriasis, urticaria, hives, pemphigus vulgaris, bullous pemphigoid, and cutaneous lupus erythematosus), hematologic disorders (such as, for example, thrombocytopenic purpura, thrombotic thrombocytopenic purpura, post-transfusion purpura, and autoimmune hemolytic anemia), atherosclerosis, uveitis, autoimmune hearing diseases (such as, for example, inner ear disease and hearing loss), Behcet's disease, Raynaud's syndrome, organ transplant, and autoimmune endocrine disorders (such as, for example, diabetic-related autoimmune diseases such as insulin-dependent diabetes mellitus (IDDM), Addison's disease, and autoimmune thyroid disease (e.g., Graves' disease and thyroiditis)). More preferred such diseases include, for example, rheumatoid arthritis, ulcerative colitis, ANCA-associated vasculitis, lupus, multiple sclerosis, Sjogren's syndrome, Graves' disease, IDDM, pernicious anemia, thyroiditis, and glomerulonephritis.

In another example, an inflammatory condition is a condition involving neutrophils, monocytes, mast cells, basophils, eosinophils, macrophages where cytokine release, histamine release, oxidative burst, phagocytosis, release of other granule enzymes and chemotaxis occur. Hypersensitivity responses (described above) can also be regarded as inflammatory diseases (acute or chronic) since they often involve complement activation and recruitment/infiltration of various leukocytes such as neutrophils, mast cells, basophils, etc.

The compositions of the present disclosure will be administered in a manner compatible with the dosage formulation and in such amount as is therapeutically/prophylactically effective. Formulations are easily administered in a variety of manners, e.g., by ingestion or injection or inhalation.

Other therapeutic regimens may be combined with the administration of a protein of the present disclosure. The combination therapy may be administered as a simultaneous or sequential regimen. When administered sequentially, the combination may be administered in two or more administrations. The combined administration includes co-administration, using separate formulations or a single pharmaceutical formulation, and consecutive administration in either order, wherein preferably there is a time period while both (or all) active agents simultaneously exert their biological activities.

Prior to therapeutic use, a protein of the present disclosure is preferably tested in vitro and/or in vivo, e.g., as described below.

In one example, a protein of the present disclosure binds to an antigen, even if conjugated to a compound. In the case of proteins derived from pre-existing proteins (e.g., antibodies), the protein of the present disclosure may bind to the antigen at least as well as the protein from which it is derived. Alternatively, the protein of the present disclosure binds to the antigen with at least about 10% or 20% or 30% or 40% or 50% or 60% or 70% or 80% or 90% of the affinity or avidity of the protein from which it is derived or a form of the protein lacking the negatively charged residues.

Exemplary methods for determining binding affinity of a protein include a simple immunoassay showing the ability of the protein to block an antibody to a target antigen, e.g., a competitive binding assay. Competitive binding is determined in an assay in which the protein under test inhibits specific binding of a reference protein to a common antigen. Numerous types of competitive binding assays are known, for example, solid phase direct or indirect radioimmunoassay (RIA), solid phase direct or indirect enzyme immunoassay (EIA), sandwich competition assay (see Stahli et al., 1983); solid phase direct biotin-avidin EIA (see Kirkland et al., 1986); solid phase direct labeled assay, solid phase direct labeled sandwich assay (see Harlow and Lane, 1988); solid phase direct biotin-avidin EIA (Cheung et al., 1990); or direct labeled RIA (Moldenhauer et al., 1990). Typically, such an assay involves the use of purified antigen bound to a solid surface or cells bearing either of these, an unlabeled test protein and a labeled reference protein. Competitive inhibition is measured by determining the amount of label bound to the solid surface or cells in the presence of the test protein The present disclosure also encompasses methods for testing the activity of a protein of the present disclosure. Various assays are available to assess the activity of a protein of the present disclosure in vitro. For example, a protein of the present disclosure is administered to a cell or population thereof to determine whether or not it can bind to said cell and/or be internalized by said cell. Such an assay is facilitated by labeling the protein of the present disclosure with a detectable label (i.e., producing a conjugate), however this is not essential since the protein of the present disclosure can also be detected with a labeled protein. Such an assay is useful for assessing the ability of a protein of the present disclosure to deliver a compound (i.e., a payload) to a cell and/or its utility in imaging. Preferably the cell expresses an antigen to which the protein of the present disclosure binds and more preferably is a cell line or primary cell culture of a cell type that it desired to be detected or treated.

Generally, the cytotoxic or cytostatic activity of a protein of the present disclosure, e.g. conjugated to a cytotoxic molecule is measured by: exposing cells expressing an antigen to which the protein of the present disclosure binds to the protein of the present disclosure; culturing the cells for a suitable period for the protein to exert a biological effect, e.g., from about 6 hours to about 5 days; and measuring cell viability, cytotoxicity and/or cell death. Cell-based in vitro assays useful for measure viability (proliferation), cytotoxicity, and cell death are known in the art.

For example, the CellTiter-Glo® Luminescent Cell Viability Assay is a commercially available (Promega Corp., Madison, Wis.) homogeneous assay method based on the recombinant expression of Coleoptera luciferase (U.S. Pat. Nos. 5,583,024; 5,674,713 and 5,700,670). This cell proliferation assay determines the number of viable cells in culture based on quantitation of the ATP present in a cell, an indicator of metabolically active cells. Alternatively, cell viability is assayed using non-fluorescent resazurin, which is added to cells cultured in the presence of a protein of the present disclosure. Viable cells reduce resazurin to red-fluorescent resorufin, easily detectable, using, for example microscopy or a fluorescent plate reader. Kits for analysis of cell viability are available, for example, from Molecular Probes, Eugene, Oreg., USA.

Other assays for cell viability include determining incorporation of $^3$H-thymidine or $^{14}$C-thymidine into DNA as it is synthesized (i.e., to determine DNA synthesis associated with cell division). In such an assay, a cell is incubated in the presence of labeled thymidine for a time sufficient for cell division to occur. Following washing to remove any unincorporated thymidine, the label (e.g. the radioactive label) is detected, e.g., using a scintillation counter. Alternative assays for determining cellular proliferation, include, for example, measurement of DNA synthesis by BrdU incorporation (by ELISA or immunohistochemistry, kits available from Amersham Pharmacia Biotech).

Exemplary assays for detecting cell death include APOPTEST (available from Immunotech) stains cells early in apoptosis, and does not require fixation of the cell sample (Martin et al. 1994). This method utilizes an annexin V antibody to detect cell membrane re-configuration that is characteristic of cells undergoing apoptosis. Apoptotic cells stained in this manner can then be sorted either by fluorescence activated cell sorting (FACS), ELISA or by adhesion and panning using immobilized annexin V antibodies. Alternatively, a terminal deoxynucleotidyl transferase-mediated biotinylated UTP nick end-labeling (TUNEL) assay is used to determine the level of cell death. The TUNEL assay uses the enzyme terminal deoxynucleotidyl transferase to label 3'-OH DNA ends, generated during apoptosis, with biotinylated nucleotides. The biotinylated nucleotides are then detected by using streptavidin conjugated to a detectable marker. Kits for TUNEL staining are available from, for example, Intergen Company, Purchase, N.Y.

In vivo stability of a protein of the present disclosure can also be assessed or predicted by exposing a protein of the present disclosure to serum and/or cells and subsequently isolating the protein of the present disclosure using, for example, immunoaffinity purification. A reduced amount of recovered protein of the present disclosure indicates that the protein of the present disclosure is degraded in serum or when exposed to cells.

In another example, the ability of the protein of the present disclosure to block binding of a ligand to a receptor is assessed using a standard radio-immunoassay or fluorescent-immunoassay.

The ability of a protein of the present disclosure to agonize or antagonize a receptor can also be assessed by determining signalling of the receptor in the presence or absence of the protein.

A protein of the present disclosure can also be tested for its stability and/or efficacy in vivo. For example, the protein of the present disclosure is administered to a subject and the serum levels of the protein is detected over time, e.g., using an ELISA or by detecting a detectable label conjugated to the protein. This permits determination of the in vivo stability of the protein of the present disclosure.

A protein of the present disclosure can also be administered to an animal model of a human disease and its effect on a symptom thereof determined. The skilled artisan will be readily able to determine a suitable model based on the antigen to which the protein of the present disclosure binds. Exemplary models of, for example, human cancer are known in the art. For example, mouse models of breast cancer include mice overexpressing fibroblast growth factor 3 (Muller et al., 1990); TGF-alpha (Matsui et al, 1990); erbB2 (Guy, et al., 1992); or transplantation of human breast cancer cells into SCID mice. Models of ovarian cancer include transplantation of ovarian cancer cells into mice (e.g., as described in Roby et al., 2000); transgenic mice chronically secreting luteinising hormone (Risma et al., 1995); or Wx/Wv mice. Mouse models of prostate cancer are also known in the art and include, for example, models resulting from enforced expression of SV40 early genes (e.g., the TRAMP model that utilizes the minimal rat probasin promoter to express the SV40 early genes or transgenic mice using the long probasin promoter to express large T antigen, collectively termed the 'LADY' model or mice expressing c-myc or Bcl-2 or Fgf8b or expressing dominant negative TGFβ (see, Matusik et al., 2001, for a review of transgenic models of prostate cancer).

A protein of the present disclosure can also be administered to an animal model of a disease other than cancer, e.g., NOD mice to test their ability to suppress, prevent, treat or delay diabetes (e.g., as described in Tang et al., 2004) and/or to a mouse model of GVHD (e.g., as described in Trenado, 2002) and/or to a mouse model of psoriasis (e.g., Wang et al. 2008) and/or to a model of rheumatoid arthritis e.g., a SKG strain of mouse (Sakaguchi et al.), rat type II collagen arthritis model, mouse type II collagen arthritis model or antigen induced arthritis models in several species (Bendele, 2001)) and/or a model of multiple sclerosis (for example, experimental autoimmune encephalomyelitis (EAE; Bradl and Linington, 1996)) and/or inflammatory airway disease (for example, OVA challenge or cockroach antigen challenge (Chen et al. 2007) and/or models of inflammatory bowel disease (e.g., dextran sodium sulphate (DSS)-induced colitis or Muc2 deficient mouse model of colitis (Van der Sluis et al. 2006).

In one example, the present disclosure provides methods for diagnosing or prognosing a condition.

As used herein, the term "diagnosis", and variants thereof such as, but not limited to, "diagnose", "diagnosed" or "diagnosing" includes any primary diagnosis of a clinical state or diagnosis of recurrent disease.

"Prognosis", "prognosing" and variants thereof as used herein refer to the likely outcome or course of a disease, including the chance of recovery or recurrence.

In one example, the method may comprise determining the amount of an antigen in a sample. Thus, the proteins of the present disclosure have utility in applications such as cell sorting (e.g., flow cytometry, fluorescence activated cell sorting), for diagnostic or research purposes. For example, a sample is contacted with a protein of the present disclosure for a time and under conditions sufficient for it to bind to an antigen and form a complex and the complex is then detected or the level of complex is determined. For these purposes, the proteins can be labeled or unlabeled. The proteins can be directly labeled, e.g., using a label described herein. When unlabeled, the proteins can be detected using suitable means, as in agglutination assays, for example. Unlabeled antibodies or fragments can also be used in combination with another (i.e., one or more) suitable reagent which can be used to detect a protein, such as a labeled antibody (e.g., a second antibody) reactive with the protein or other suitable reagent (e.g., labeled protein A).

Preferably, a protein of the present disclosure is used in an immunoassay. Preferably, using an assay selected from the group consisting of, immunohistochemistry, immunofluorescence, enzyme linked immunosorbent assay (ELISA), fluorescence linked immunosorbent assay (FLISA) Western blotting, RIA, a biosensor assay, a protein chip assay and an immunostaining assay (e.g. immunofluorescence).

Standard solid-phase ELISA or FLISA formats are particularly useful in determining the concentration of a protein from a variety of samples.

In one form, such an assay involves immobilizing a biological sample onto a solid matrix, such as, for example a polystyrene or polycarbonate microwell or dipstick, a membrane, or a glass support (e.g. a glass slide). A protein of the present disclosure that specifically binds to an antigen of interest is brought into direct contact with the immobilized sample, and forms a direct bond with any of its target antigen present in said sample. This protein of the present disclosure is generally labeled with a detectable reporter molecule, such as for example, a fluorescent label (e.g. FITC or Texas Red) or a fluorescent semiconductor nanocrystal (as described in U.S. Pat. No. 6,306,610) in the case of a FLISA or an enzyme (e.g. horseradish peroxidase (HRP), alkaline phosphatase (AP) or β-galactosidase) in the case of an ELISA, or alternatively a labeled antibody can be used that binds to the protein of the present disclosure. Following washing to remove any unbound protein the label is detected either directly, in the case of a fluorescent label, or through the addition of a substrate, such as for example hydrogen peroxide, TMB, or toluidine, or 5-bromo-4-chloro-3-indol-beta-D-galaotopyranoside (x-gal) in the case of an enzymatic label. Such ELISA or FLISA based systems are particularly suitable for quantification of the amount of a protein in a sample, by calibrating the detection system against known amounts of a protein standard to which the protein binds, such as for example, an isolated, engineered or non-naturally occurring and/or recombinant protein or immunogenic fragment thereof or epitope thereof.

In another form, an ELISA or FLISA may comprise immobilizing a protein of the present disclosure or an antibody that binds to an antigen of interest on a solid matrix, such as, for example, a membrane, a polystyrene or polycarbonate microwell, a polystyrene or polycarbonate dipstick or a glass support. A sample is then brought into physical contact with said protein of the present disclosure or antibody, and the protein to which said compound binds is bound or 'captured'. The bound protein is then detected using a labeled protein of the present disclosure that binds to a different protein or a different site in the same antigen. Alternatively, a third labeled antibody can be used that binds the second (detecting) protein.

As will be apparent to the skilled artisan from the foregoing, the present disclosure also contemplates imaging methods using a protein of the present disclosure. For imaging, protein of the present disclosure is conjugated to a detectable label, which can be any molecule or agent that can emit a signal that is detectable by imaging. For example, the detectable label may be a protein, a radioisotope, a fluorophore, a visible light emitting fluorophore, infrared light emitting fluorophore, a metal, a ferromagnetic substance, an electromagnetic emitting substance a substance with a specific magnetic resonance (MR) spectroscopic signature, an X-ray absorbing or reflecting substance, or a sound altering substance.

The protein of the present disclosure can be administered either systemically or locally to the tumor, organ, or tissue to be imaged, prior to the imaging procedure. Generally, the protein is administered in doses effective to achieve the desired optical image of a tumour, tissue, or organ. Such doses may vary widely, depending upon the particular protein employed, the tumour, tissue, or organ subjected to the imaging procedure, the imaging equipment being used, and the like.

In some examples of the disclosure, the protein of the present disclosure is used as in vivo optical imaging agents of tissues and organs in various biomedical applications including, but not limited to, imaging of tumors, tomographic imaging of organs, monitoring of organ functions, coronary angiography, fluorescence endoscopy, laser guided surgery, photoacoustic and sonofluorescence methods, and the like. Exemplary diseases, e.g., cancers, in which a protein of the present disclosure is useful for imaging are described herein and shall be taken to apply mutatis mutandis to the present example of the disclosure. In one example, a protein conjugate of the disclosure is useful for the detection of the presence of tumors and other abnormalities by monitoring where a particular protein of the present disclosure is concentrated in a subject. In another example, the protein of the present disclosure is useful for laser-assisted guided surgery for the detection of micro-metastases of tumors upon laparoscopy. In yet another example, the protein of the present disclosure is useful in the diagnosis of atherosclerotic plaques and blood clots.

Examples of imaging methods include magnetic resonance inaging (MRI), MR spectroscopy, radiography, CT, ultrasound, planar gamma camera imaging, single-photon emission computed tomography (SPECT), positron emission tomography (PET), other nuclear medicine-based imaging, optical imaging using visible light, optical imaging using luciferase, optical imaging using a fluorophore, other optical imaging, imaging using near infrared light, or imaging using infrared light.

Certain examples of the methods of the present disclosure further include imaging a tissue during a surgical procedure on a subject.

A variety of techniques for imaging are known to those of ordinary skill in the art. Any of these techniques can be applied in the context of the imaging methods of the present disclosure to measure a signal from the detectable label. For example, optical imaging is one imaging modality that has gained widespread acceptance in particular areas of medicine. Examples include optical labeling of cellular components, and angiography such as fluorescein angiography and indocyanine green angiography. Examples of optical imaging agents include, for example, fluorescein, a fluorescein derivative, indocyanine green, Oregon green, a derivative of Oregon green derivative, rhodamine green, a derivative of rhodamine green, an eosin, an erytlirosin, Texas red, a derivative of Texas red, malachite green, nanogold sulfosuccinimidyl ester, cascade blue, a coumarin derivative, a naphthalene, a pyridyloxazole derivative, cascade yellow dye, dapoxyl dye.

Gamma camera imaging is contemplated as a method of imaging that can be utilized for measuring a signal derived from the detectable label. One of ordinary skill in the art would be familiar with techniques for application of gamma camera imaging. In one example, measuring a signal can involve use of gamma-camera imaging of an $^{111}$In or $^{99m}$Tc conjugate, in particular $^{111}$In-octreotide or $^{99m}$Tc-somatostatin analogue.

Computerized tomography (CT) is contemplated as an imaging modality in the context of the present disclosure. By taking a series of X-rays from various angles and then combining them using computer software, CT makes it possible to construct a three-dimensional image of any part of the body. A computer is programmed to display two-dimensional slices from any angle and at any depth. The slices may be combined to build three-dimensional representations.

In CT, intravenous injection of a radiopaque contrast agent conjugated to a protein of the present disclosure, which binds to an antigen of interest can assist in the identification and delineation of tissue masses (e.g., soft tissue masses) when initial CT scans are not diagnostic. Similarly, contrast agents aid in assessing the vascularity of a soft tissue lesion. For example, the use of contrast agents may aid the delineation of the relationship of a tumor and adjacent vascular structures.

CT contrast agents include, for example, iodinated contrast media. Examples of these agents include iothalamate, iohexol, diatrizoate, iopamidol, ethiodol, and iopanoate. Gadolinium agents have also been reported to be of use as a CT contrast agent, for example, gadopentate.

Magnetic resonance imaging (MRI) is an imaging modality that uses a high-strength magnet and radio-frequency signals to produce images. In MRI, the sample to be imaged is placed in a strong static magnetic field and excited with a pulse of radio frequency (RF) radiation to produce a net magnetization in the sample. Various magnetic field gradients and other RF pulses then act to code spatial information into the recorded signals. By collecting and analyzing these signals, it is possible to compute a three-dimensional image which, like a CT image, is normally displayed in two-dimensional slices. The slices may be combined to build three-dimensional representations.

Contrast agents used in MRI or MR spectroscopy imaging differ from those used in other imaging techniques. Examples of MRI contrast agents include gadolinium chelates, manganese chelates, chromium chelates, and iron particles. For example, a protein of the present disclosure is conjugated to a compound which may comprise a chelate of a paramagnetic metal selected from the group consisting of scandium, titanium, vanadium, chromium, manganese, iron, cobalt, nickel, copper, molybdenum, ruthenium, cerium, indium, praseodymium, neodymium, promethium, samarium, europium, gadolinium, terbium, dysprosium, holmium, erbium, thulium, and ytterbium. A further example of imaging agents useful for the present disclosure is halocarbon-based nanoparticle such as PFOB or other fluorinebased MRI agents. Both CT and MRI provide anatomical information that aid in distinguishing tissue boundaries and vascular structure.

Imaging modalities that provide information pertaining to information at the cellular level, such as cellular viability, include positron emission tomography (PET) and single-photon emission computed tomography (SPECT). In PET, a patient ingests or is injected with a radioactive substance that emits positrons, which can be monitored as the substance moves through the body.

The major difference between PET and SPECT is that instead of a positron-emitting substance, SPECT uses a radioactive tracer that emits high-energy photons. SPECT is valuable for diagnosing multiple illnesses including coronary artery disease, and already some 2.5 million SPECT heart studies are done in the United States each year.

For PET, a protein of the present disclosure is commonly labeled with positron-emitters such as $^{11}$C, $^{13}$N, $^{15}$O, $^{18}$F, $^{82}$Rb, $^{62}$Cu, and $^{68}$Ga. Proteins of the present disclosure are labeled with positron emitters such as 99mTc, $^{201}$Tl, and $^{67}$Ga, $^{111}$In for SPECT.

Non-invasive fluorescence imaging of animals and humans can also provide in vivo diagnostic information and be used in a wide variety of clinical specialties. For instance, techniques have been developed over the years including simple observations following UV excitation of fluorophores up to sophisticated spectroscopic imaging using advanced equipment (see, e.g., Andersson-Engels et al, 1997). Specific devices or methods known in the art for the in vivo detection of fluorescence, e.g., from fluorophores or fluorescent proteins, include, but are not limited to, in vivo near-infrared fluorescence (see, e.g., Frangioni, 2003), the Maestro™ in vivo fluorescence imaging system (Cambridge Research & Instrumentation, Inc.; Woburn, Mass.), in vivo fluorescence imaging using a flying-spot scanner (see, e.g., Ramanujam et al, 2001), and the like.

Other methods or devices for detecting an optical response include, without limitation, visual inspection, CCD cameras, video cameras, photographic film, laser-scanning devices, fluorometers, photodiodes, quantum counters, epifluorescence microscopes, scanning microscopes, flow cytometers, fluorescence microplate readers, or signal amplification using photomultiplier tubes.

In some examples, an imaging agent is tested using an in vitro or in vivo assay prior to use in humans, e.g., using a model described herein.

The present disclosure also provides an article of manufacture, or "kit", containing a protein of the present disclosure. The article of manufacture can comprise a container and a label or package insert on or associated with the container, e.g., providing instructions to use the protein of the present disclosure in a method described herein according to any example. Suitable containers include, for example, bottles, vials, syringes, blister pack, etc. The containers may be formed from a variety of materials such as glass or plastic. The container holds a protein of the present disclosure composition and may have a sterile access port (for example the container may be an intravenous solution bag or a vial having a stopper pierceable by a hypodermic injection needle). Alternatively, or additionally, the article of manufacture may further comprise a second (or third) container which may comprise a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes. The kit may also or alternatively comprise reagents for detecting a protein of the present disclosure and/or for conjugating to a protein of the present disclosure.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

Example 1

Materials and Methods 1.1 Generation of Mutant $V_L$ and scFv

Mutants of human variable domains were generated using the method as described by Zoller and Smith (1987), with modifications introduced by Kunkel et al. (1987). For this purpose, synthetic oligonucleotides encoding the desired mutations were annealed to a uracil-containing single-stranded template DNA (dU-ssDNA), enzymatically extended and ligated to form covalently closed circular DNA. Template was generated by the cloning of DNA fragments encoding a single human light chain variable ($V_L$) domain (DPK9 (SEQ ID NO: 2) or $V_L$ from adalimumab (SEQ ID NO: 8) or 4D5 (SEQ ID NO: 12)) into the phage display vector, FdMyc, using ApaLI and NotI sites. Covalently closed circular DNA was transformed by electroporation into the ung$^+$ E. coli strain TG1, causing preferential destruction of non-mutated dU-ssDNA. The sequences of the constructed mutants were confirmed by DNA sequence analysis.

For the generation of scFv mutants, DNA fragments encoding a $V_H$ domain and synthetic linker region were cloned into the corresponding $V_L$-FdMyc constructs using ApaLI and SalI cloning sites. The sequences of the constructed mutants were confirmed by DNA sequence analysis. The sequence encoding a control scFv is set forth in SEQ ID NO: 6, the sequence encoding a scFv derived from adalimumab is set forth in SEQ ID NO: 10, and the sequence encoding a scFv derived from 4D5 is set forth in SEQ ID NO: 14.

When $V_L$ were expressed as soluble protein, the N-terminal glutamine was substituted with aspartic acid. When $V_H$ or scFv were expressed as soluble protein, the N-terminal glutamine was substituted with glutamic acid Phage display repertoires of human $V_L$ domains were generated based on Vκ1/DPK9. The repertoires were constructed in FdMyc using synthetic oligonucleotide-mediated diversification (Kunkel el al., 1987) (amino acid numbering according to Kabat and nucleotide codes according to IUPAC-IUB, Cornish-Bowden, 1985). For this purpose, diversity was introduced into L1 using synthetic oligonucleotides encoding the degenerate codon KMT (Y/A/D/S) at positions 28, 30, 31 and 32. L3 diversity was introduced at positions 91, 92, 93, 94 and 96 using trinucleotide phosphoramidite oligonucleotides (Virnekäs et al., 1994) encoding (20% Y; 17% G; 15% S; 7% D/A; 4% T/P/V/R/I/L; 2% W/F/M/Q/N/HK/E). L2 was restricted to either the germline Vκ1/DPK9 consensus sequence (WT) or aspartic acid at positions 52 and 53 (52D/53D).

1.2 Phage ELISA for Aggregation-Resistance ("Heat/Cool Assay")

The aggregation-resistance of clones was analyzed by measuring retention of signal after heat incubation in a phage ELISA format (McCafferty et al., 1990; Jespers et al., 2004). Wells of a Nunc Maxisorp Immuno-plate were coated overnight with protein A, protein L or a target antigen in carbonate buffer (pH 9.6). The plate was washed once with PBS and blocked with about 4% (w/v) milk powder diluted in PBS (MPBS). Single colonies were picked from agar plates and grown overnight in 2×TY medium (containing about 16 g/L tryptone; about 10 g/L yeast extract; about 5 g/L NaCl, pH 7.0) supplemented with about 15 µg/ml tetracycline shaking at about 30° C. Cells were removed by centrifugation and phages were biotinylated directly in the culture supernatant by adding biotin-PEO$_4$—N-hydroxysuccinimide (Pierce; about 50 M final concentration). Excess biotinylation reagent was quenched using 100 mM TrisHcl pH7.5. For heat selection, supernatant was first incubated at about 80° C. for about 10 min and then at about 4° C. for about 10 min. Supernatant was added to the blocked ELISA wells. After three washes with PBS, bound phage particles were detected using an Extravidin-HRP conjugate (Sigma) and 3,3',5,5'-tetramethylbenzidine (TMB) substrate. Absorbance was calculated by subtracting measurements at 450 and 650 nm.

The aggregation-resistance of clones on target antigen was analyzed by measuring retention of signal after heat incubation in a phage ELISA format (McCafferty et al., 1990; Jespers et al., 2004). Wells of a Nunc Maxisorp Immuno-plate were coated overnight with streptavidin in PBS buffer. The plate was washed once with PBS and blocked with about 4% (w/v) milk powder diluted in PBS (MPBS). Biotinylated antigen was then added to the plate. Single colonies were picked from agar plates and grown overnight in 2×TY medium (containing about 16 g/L tryptone; about 10 g/L yeast extract; about 5 g/L NaCl, pH 7.0) supplemented with about 15 µg/ml tetracycline shaking at about 30° C. Cells were removed by centrifugation. 100 mM TrisHCl pH7.5 was added to the supernatant. For heat selection, supernatant was first incubated at about 80° C. for about 10 min and then at about 4° C. for about 10 min. Supernatant was added to the blocked ELISA wells. After three washes with PBS, bound phage particles were detected using an Extravidin-HRP conjugate (Sigma) and 3,3',5,5'-tetramethylbenzidine (TMB) substrate. Absorbance was calculated by subtracting measurements at 450 and 650 nm.

1.3 Expression and Purification of $V_L$ Domains

Experiments were performed to determine the level of soluble expression of native and mutant $V_L$s. For this purpose DNA fragments encoding the domains were cloned into the expression vector pET12 using SalI and BamHI sites. Plasmids were transformed into E. coli BL21-Gold (clone DE3) (Novagen) and soluble protein expression induced by the addition of isopropyl β-D-1-thiogalactopyranoside (IPTG; 1 mM final concentration). Cells were then grown at 30° C. for 48 hr with a re-induction step after 24 hours. Cells were removed by centrifugation and supernatant containing expressed protein was filtered (0.22 µm). Supernatant of $V_L$ domains was added to rProtein L resin (Genscript) and incubated overnight at 4° C. Protein L resin was added to gravity columns where supernatant was allowed to pass over resin before being washed with PBS. $V_L$ domains were eluted by adding 0.1 M glycine-HCl pH 2.7 and fractions were neutralized by adding 0.1 M Tris-HCl pH 8.0. Domains were dialysed against PBS and concentrated. Protein purity was assessed by SDS-PAGE on a 4-12% Bis-Tris gel (Invitrogen).

1.4 Determining Soluble Expression Levels of $V_L$ Domains

The soluble expression level of each $V_L$ variant was determined using a protein L ELISA, in which the concentration of soluble domain was measured against a standard curve of the same purified protein. For this purpose, three separate colonies of freshly transformed E. coli BL21-Gold were grown and induced for expression for 48 hr as described above. Cells were removed by centrifugation and fragments were biotinylated directly in the culture supernatant by adding biotin-PEO$_4$—N-hydroxysuccinimide (Pierce; 50 µM final concentration). Culture supernatant and biotinylated purified fragments of the same mutant at known concentrations were added to a 96-well Maxisorp immuno-plate (Nunc) coated overnight with 5 µg/ml Protein L (Sigma) and blocked with 4% (w/v) skim milk powder in PBS. After three washes with PBST, bound antibody fragments were detected using Extravidin-HRP conjugate (Sigma) and TMB substrate. Absorbance was measured at 450 nm (reference 650 nm) and concentrations of each sample were extrapolated from the standard curve using linear regression analysis.

1.5 Size Exclusion Chromatography and Refoldability after Heating $V_L$ elution volumes and refolding yields after heating were determined by size-exclusion chromatography. For this purpose, purified $V_L$ variants at 100 µM in 20 mM PO$_4$ (pH 7.4) were heated to 85° C. for 20 min, followed by 4° C. for 10 min; or unheated. Both heated and unheated samples were centrifuged at 16,000×g for 10 min before being analyzed on a Superdex-G75 column (GE Healthcare) equilibrated with PBS, connected to an AKTA Purifier (GE Healthcare). Samples were injected at a volume of 500 µl with a flow rate of 0.5 ml/min. The recovery of each variant was determined by measuring the area under the curve of the heated sample, expressed as percentage of the unheated sample.

The elution volumes of whole IgG molecules were also measured by size-exclusion chromatography. For this purpose, human IgG1 containing the germline $V_H$ domain DP47 and germline $V_L$ domain DPK9 with aspartic acid and/or glutaminc acid substitutions in either CDR-H1 (31-33DED), CDR-L2 (50,52-53DDD) or in both domains together (31-33DED/50,52-53DDD) were analyzed on a Superdex-S200 column (GE Healthcare) equilibrated with PBS, connected to an AKTA Purifier (GE Healthcare). Samples at 0.5 mg/ml in PBS were injected at a volume of 100 µl with a flow rate of 0.5 ml/min. Likewise, the elution volumes of IgGs of 4D5 containing aspartic acid substitutions in CDR-H1 (position 30), CDR-L2 (position 52) or both, were assessed by size exclusion chromatography as described above.

1.6 Turbidity Measurements

Turbidity measurements of solutions containing mutant germ-line $V_L$ and scFv fragments were performed by measuring the absorbance at 360 nm of purified fragments while heating. The conditions for each fragment type was as follows: germ-line $V_L$ mutants were at 100 µM in 20 mM PO$_4$ (pH 7.4), 85° C.; scFv mutants were at 10 µM in Phosphate buffered saline, 85° C. Measurements were made on a Varian Cary 50 Bio UV-Vis spectrophotometer (Agilent Technologies) using QS-24 quartz cuvette with a 1 cm path length.

1.7 SK-BR-3 Cell Binding Assay

Whole cell binding assays using 4D5 variants as whole IgG were performed on the SK-BR-3 human breast cancer cell line. For this purpose, varying concentrations of 4D5 as human IgG1 containing mutations in CDR-H1 (position 30), CDR-L2 (position 52) or both, were added to cells (2.5×10⁴ cells/sample), in duplicate, for 1 hr on ice. Following washes in PBS containing 1% BSA, secondary antibody anti-human IgG-FITC (Sigma) was added for 30 min on ice. Fluorescence intensity of the live cell population was recorded using FACSCalibur (BD Biosciences) and analyzed using FlowJo 7.6.5 software (Tree Star).

1.8 SK-BR-3 Cell Proliferation Assays

SK-BR-3 cells were maintained in RPMI-1640 medium (Invitrogen, Carlsbad, Calif.) supplemented with 10% fetal bovine serum (FBS). Cells were detached using 0.05% trypsin/EDTA (Invitrogen) and suspended in complete medium at 2×10⁴ cells/ml. Aliquots of 500 µl were added to a 48-well cell culture plate (Corning, Lowell, Mass.) and allowed to adhere for 30 minutes before 4D5 IgG variants were added at a final concentration of 10 µg/ml. After 7 days, wells were washed with RPMI medium (without FBS), detached (as above) and live cells counted. Cell proliferation levels were calculated as a percentage of cells grown in the absence of IgG.

1.9 Affinity Measurements

The binding affinities of 4D5 scFv variants were measured using surface plasmon resonance (BIAcore, GE Healthcare). Biotinylated HER2 extracellular domain was immobilized on a streptavidin sensor chip. Dilution series of each scFv variant were injected at a flow rate of 20 µl/min and curves fitted to a 1:1 langmuir binding model.

Example 2

Aggregation-Resistance of DPK9 CDR1 Mutants

Experiments were performed to investigate the effects of introducing single or multiple negatively charged amino acids into CDR1 of DPK9. The mutant $V_L$s constructed and tested for aggregation-resistance, as detailed above (see the Materials and Methods section). Briefly, phage-displayed $V_L$ were heated to 80° C. for 10 min, followed by cooling at 4° C. for 10 min. Correctly folded $V_L$ were captured by protein L ELISA and the absorbance signal of the treated sample was calculated as a percentage of the untreated sample.

Results are shown in FIG. 1. In summary, the introduction of negatively charged amino acids into CDR1 of DPK9 $V_L$ improved aggregation resistance to a small degree, with substitutions at positions 24 and 29 conferring the greatest level of aggregation resistance.

Example 3

Aggregation-Resistance of DPK9 FR2/CDR2 Mutants

Experiments were then performed to investigate the effects of introducing single or multiple negatively charged amino acids into CDR2 and adjacent FR2 residues of DPK9. Single amino acid changes and combinations of changes in the CDR2 and adjacent FR2 region of the DPK9 $V_L$ domain were constructed and tested for aggregation-resistance, as detailed above (see the Materials and Methods section). Briefly, phage-displayed $V_L$ were heated to 80° C. for 10 min, followed by cooling at 4° C. for 10 min. Correctly folded $V_H$ were captured by protein L ELISA and the absorbance signal of the treated sample was calculated as a percentage of the untreated sample.

Figure 2:
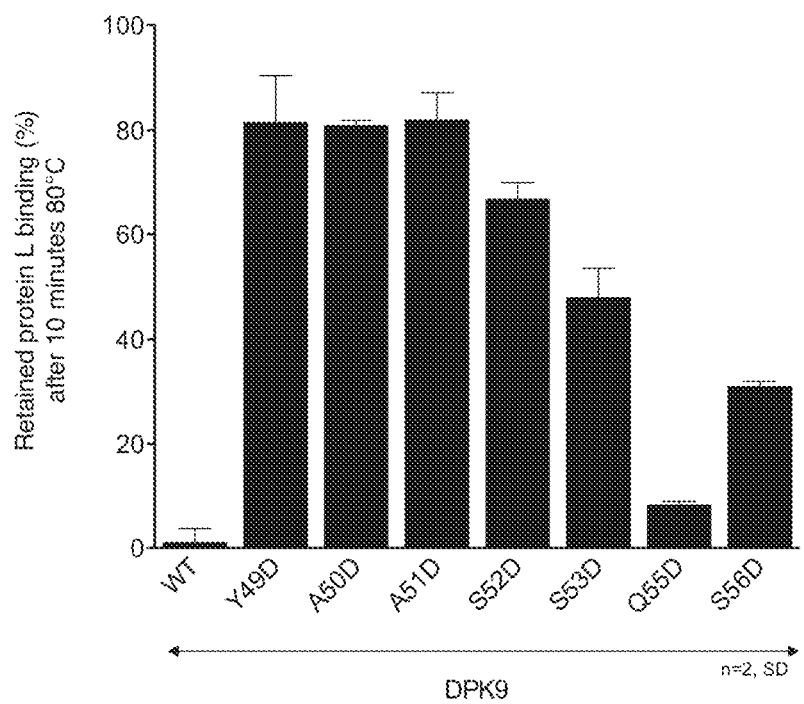
FIG. 2 is a graphical representation showing aggregation-resistance of $V_L$ from DPK9 which may comprise single negative charged amino acid (aspartic acid) changes, and combinations thereof between residues 49 and 56. Positioning of any substitutions is indicated on the X axis. Y-axis depicts percentage retained protein L binding when subjected to the "heat/cool" assay on phage exemplified herein.

Results are shown in FIG. 2. In summary, introduction of negatively charged amino acids at position 49 of FR2 or any one of positions 50, 51, 52 and 53 of CDR2 resulted in considerable aggregation-resistance of the $V_L$ domain. Furthermore, combinations of two, three or four mutations resulted in aggregation-resistance, with many of these combinations achieving almost 100% aggregation-resistance.

Example 4

Production of Libraries of Aggregation-Resistant Variable Domains

Figure 3:
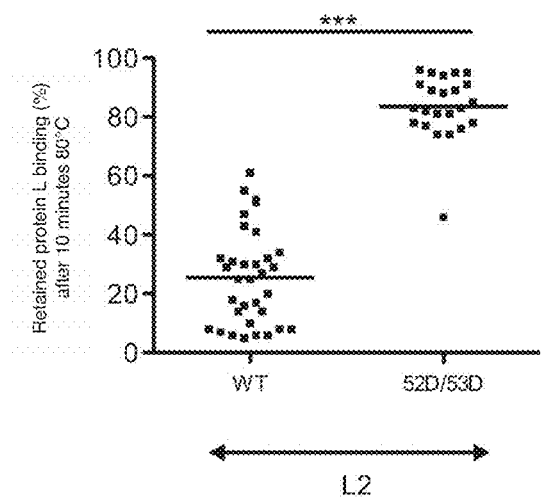
FIG. 3 is a graphical representation showing aggregation-resistance of individual members of a library of $V_L$s which may comprise negatively charged amino acids at positions 52 and 53. Also shown are aggregation resistance of wild type variable domains (WT). The Y-axis depicts percentage binding to protein L of heated and cooled variable domains on phage, compared to untreated controls. ***p<0.001

Libraries of $V_H$ and $V_L$ variants were produced by randomizing surface exposed CDR residues, mimicking the natural amino acid distribution in the antibody repertoire. The introduction of aspartates at positions 32 and 33 of $V_H$ or at positions 52 and 53 of $V_L$ significantly increased the mean aggregation-resistance of the libraries (FIG. 3). The observed effect was largely independent of other CDR residues, highlighting the dominant effect of mutations at hot-spot positions.

Example 5

Characterization of Aggregation-Resistance in Solution

Figure 4A:
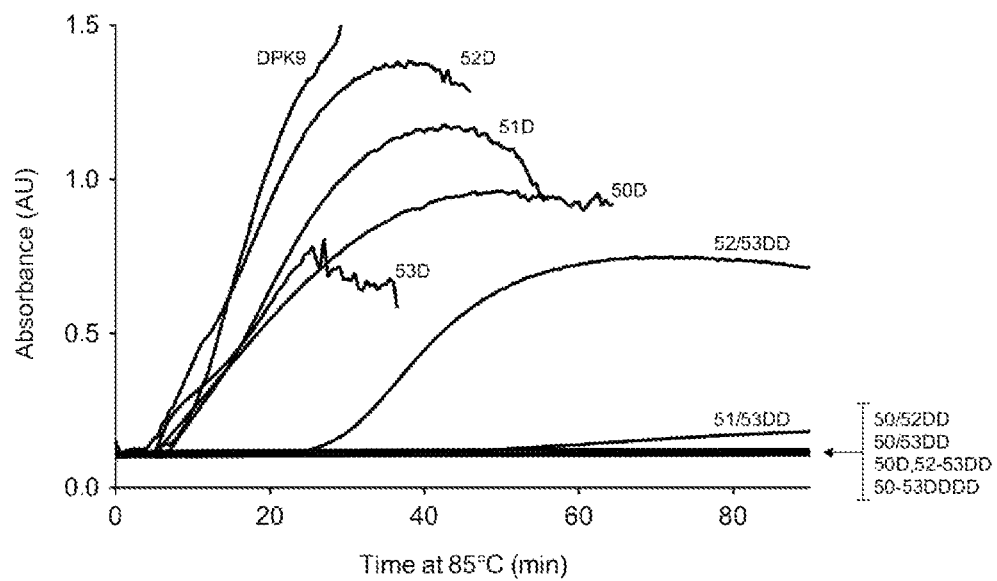
FIG. 4A is a graphical representation showing turbidity of $V_L$s following heating to 85° C. Depicted are results produced using $V_L$s which may comprise no negatively charged amino acids (DPK9), one negatively charged amino acid (50D, 51D, 52D or 53D), two negatively charged amino acids (50/52DD, 50/53DD, 51/53DD, 52/53DD) and three negatively charged amino acids (50-53DADD), and four negatively charged amino acids (50-53DDDD). The X-axis depicts time for which the $V_L$s are maintained at 85° C. The Y-axis depicts absorbance measured at 360 nm.

Representative protein variants were expressed as single domains to assess their aggregation propensity as soluble proteins. Germ-line $V_H$ and $V_L$ domains rapidly aggregate when heated above their melting temperatures. Introduction of single negative charge within the $V_L$ (including position 50, 51, 52 or 53) moderately increased resistance to aggregation (FIG. 4). Charges at two or more positions selected from positions 50-53 further increased aggregation-resistance (FIGS. 4A and B). The introduction of an increasing number of negative charges also improves a range of other biophysical properties of antibody variable domains (Table 1 and FIG. 5). As the number of mutations increases from none to three, expression levels increase 2-fold for $V_L$ domains. Other common measures, such as elution volume on gel filtration and refolding yields also improve noticeably (Table 1 and FIG. 5).

TABLE 1

Effects of negatively charged residues in $V_L$.

| | | Mutations | | |
|---|---|---|---|---|
| | None | Single | Double | Triple |
| | Expression (mg/l) | | | |
| $V_L$ | 50.0 | 50D = 140.9 | 50D/52D = 164.2 | 50-53DADD = 104.6 |
| | | 51D = 50.6 | 51D/53D = 82.3 | |
| | | 52D = 52.9 | 52D/53D = 67.5 | |
| | | 53D = 69.8 | | |

TABLE 1-continued

Effects of negatively charged residues in $V_L$.

| | Mutations | | | |
|---|---|---|---|---|
| | None | Single | Double | Triple |
| Mean | 50 | 78.6 | 104.7 | 104.6 |
| St. Dev. | | 42.4 | 52.1 | |
| Elution (ml) | | | | |
| $V_L$ | 13.5 | 50D = 13.1 | 50D/52D = 12.9 | 50-53DADD = 12.9 |
| | | 52D = 13.5 | 50D/53D = 13 | |
| | | 53D = 13.4 | 51D/53D = 12.9 | |
| | | | 52D/53D = 13.2 | |
| Mean | 13.5 | 13.3 | 13.0 | 12.9 |
| St. Dev. | | 0.2 | 0.1 | |
| Refolding (%) | | | | |
| $V_L$ | 13.5 | 50D = 13.1 | 50D/52D = 12.9 | 50-53DADD = 12.9 |
| | | 52D = 13.5 | 50D/53D = 13 | |
| | | 53D = 13.4 | 51D/53D = 12.9 | |
| | | | 52D/53D = 13.2 | |
| Mean | 13.5 | 13.3 | 13.0 | 12.9 |
| St. Dev. | | 0.2 | 0.1 | |

Example 6

Aggregation-Resistance of Mutant $V_L$ Derived from Adalimumab

Figure 6:
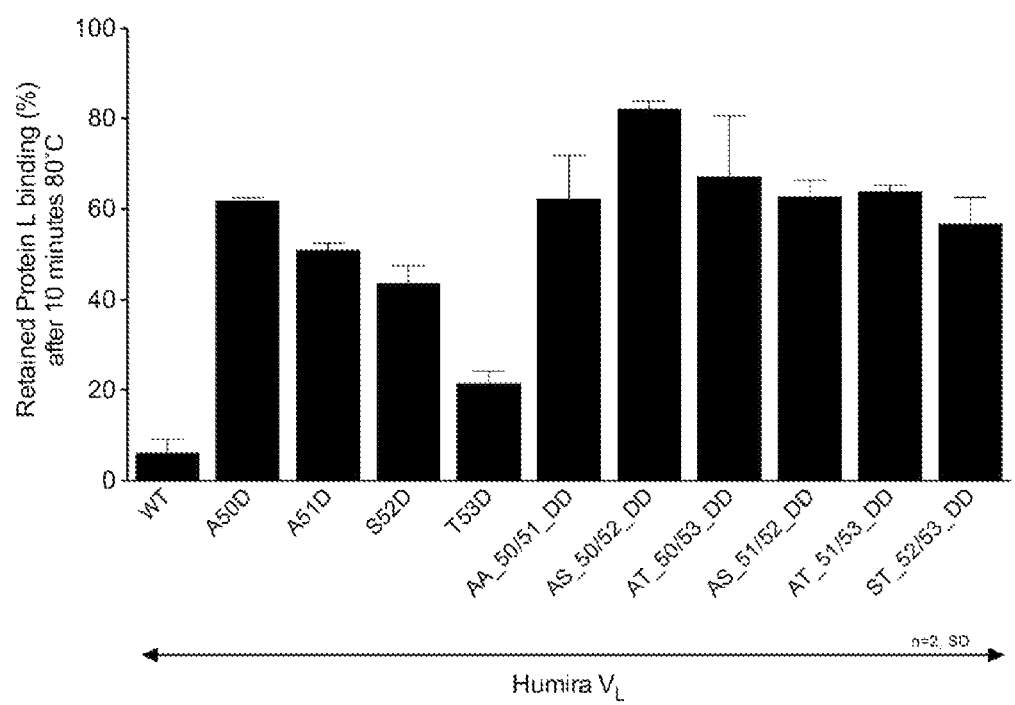
FIG. 6 is a graphical representation showing aggregation-resistance of a $V_L$ from adalimumab (Humira) which may comprise single negative charged amino acid changes, and combinations thereof between residues 50 and 53. Positioning of any substitutions is indicated on the X axis. DPK9 is an example of a $V_L$ that has a low level of aggregation resistance. "WT" is the $V_L$ from adalimumab.

The $V_L$ of adalimumab was mutated to introduce negatively charged amino acids at single or multiple positions within LCDR2, displayed on the surface of phage and tested for aggregation-resistance, as detailed above (see the Materials and Methods section). Briefly, phage were heated to 80° C. for 10 min, followed by cooling at 4° C. for 10 min. Correctly folded $V_L$ were captured by a protein L ELISA and the absorbance signal of the treated sample was calculated as a percentage of the untreated sample. Results of the protein L ELISA are shown in FIG. 6. Briefly, all tested negatively charged amino acids and combinations thereof increased binding of the $V_L$ to protein L after heating compared to wild type (non mutant) $V_L$. The combination of negatively charged amino acids at positions 50 and 52 provided the greatest level of aggregation resistance.

Example 7

Aggregation-Resistance of Mutant $V_L$ Derived from 4D5

Experiments were performed to investigate the effects of introducing single or multiple negatively charged amino acids into CDR2 of the $V_L$ of 4D5.

Single amino acid changes and combinations of changes in the CDR2 of the 4D5 $V_L$ domain were constructed and tested for aggregation-resistance, as detailed above (see the Materials and Methods section).

Briefly, phage-displayed $V_L$ were heated to 80° C. for 10 min, followed by cooling at 4° C. for 10 min. Correctly folded $V_L$ were captured by protein L ELISA and the absorbance signal of the treated sample was calculated as a percentage of the untreated sample.

Figure 7:
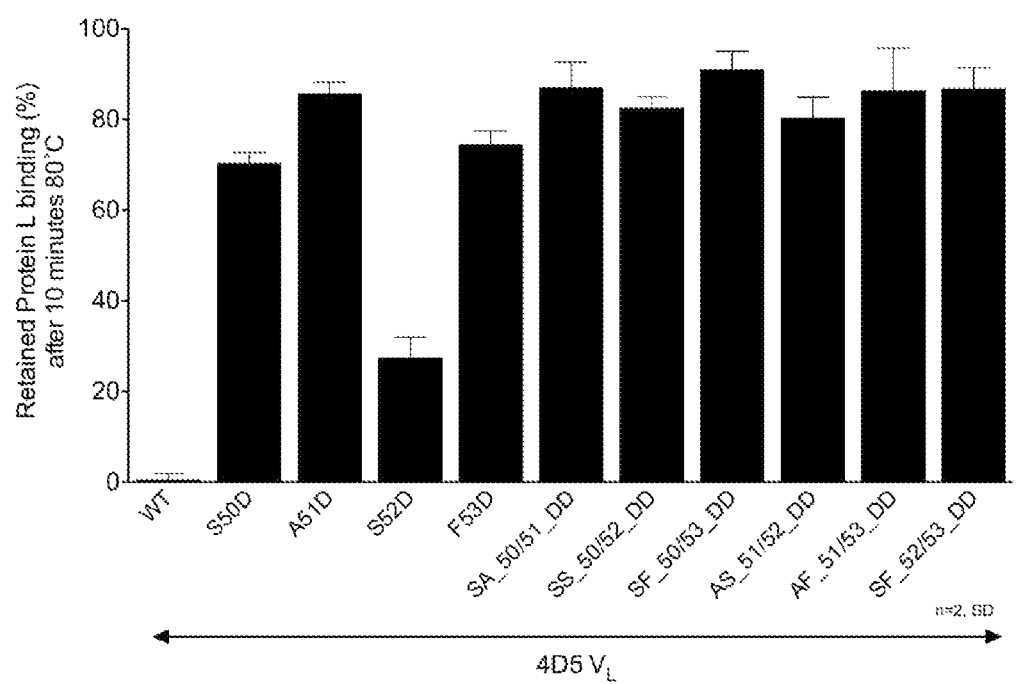
FIG. 7 is a graphical representation showing aggregation-resistance of a $V_L$ from antibody 4D5 which may comprise single negative charged amino acid changes, and combinations thereof between residues 50 and 53. Positioning of any substitutions is indicated on the X axis. DPK9 is an example of a $V_L$ that has a low level of aggregation resistance. "WT" is the $V_L$ from 4D5.

Results of the protein L ELISA are shown in FIG. 7. In summary, introduction of negatively charged amino acids at any of positions 50-53 and any of the tested combinations thereof enhanced aggregation resistance of the $V_L$ compared to the wild type (non-mutant) $V_L$.

Example 8

Aggregation-Resistance of Mutant scFv Derived from 4D5

The $V_L$ and $V_H$ of 4D5 were paired via a linker in a scFv format (see the Materials and Methods section for experimental details). Additionally, the $V_L$ was mutated to introduce negatively charged amino acids at single or multiple positions within CDR1 or CDR2. Single chain Fv were displayed on the surface of phage and tested for aggregation-resistance, as detailed above (see the Materials and Methods section). Briefly, phage were heated to 80° C. for 10 min, followed by cooling at 4° C. for 10 min. Correctly folded scFv were captured by a protein L ELISA or an ELISA using immobilized Her2 and the absorbance signal of the treated sample was calculated as a percentage of the untreated sample.

Figure 8A:
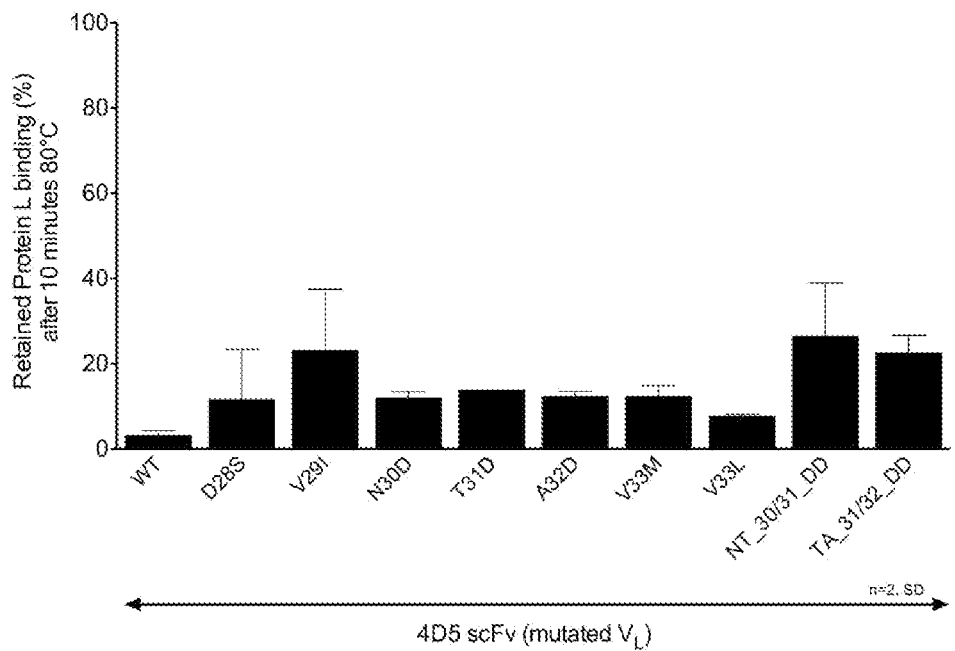
FIG. 8A is a graphical representation showing aggregation-resistance of a scFv from 4D5 which may comprise single negative charged amino acid changes, and combinations thereof in CDR1 of the $V_L$. Positioning of any substitutions is indicated on the X axis. "WT" is the scFv from 4D5.
Figure 8B:
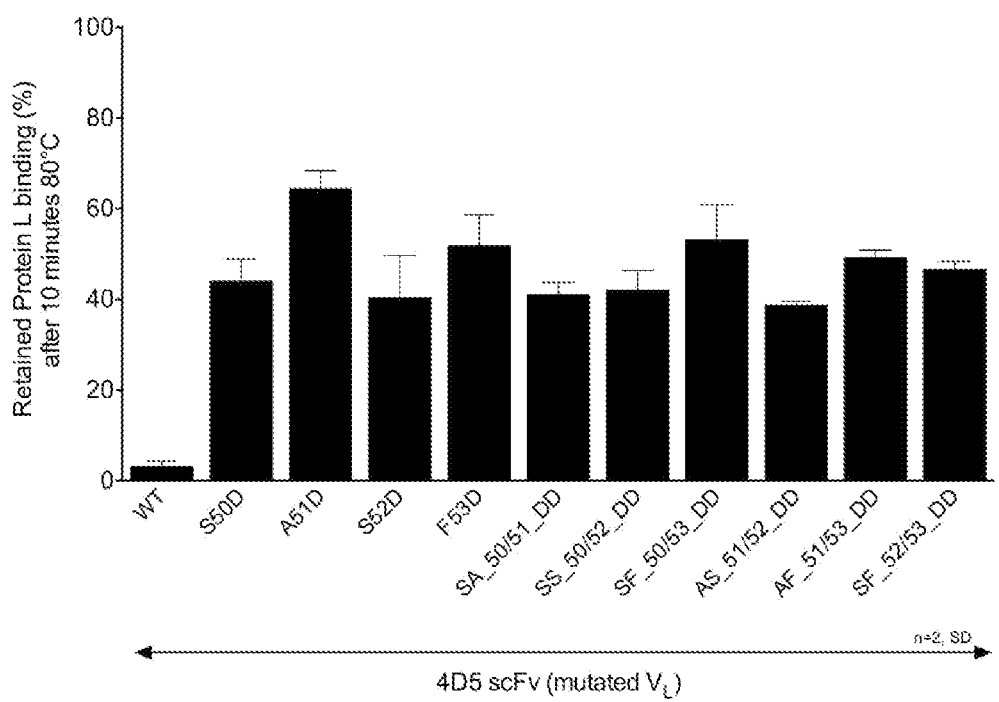
FIG. 8B is a graphical representation showing aggregation-resistance of a scFv from 4D5 which may comprise single negative charged amino acid changes, and combinations thereof in CDR2 of the $V_L$. Positioning of any substitutions is indicated on the X axis. "WT" is the scFv from 4D5.

Results of the protein L ELISA are shown in FIG. 8. Briefly, introducing negatively charged amino acids at one or more positions within CDR2 considerably increased the aggregation-resistance of the scFv compared to the wild-type (non mutant) scFv. Negatively charged amino acids in CDR1 also increased aggregation-resistance compared to wild type scFv (FIG. 8A), however not to the same degree as mutations in CDR2 (FIG. 8B). Positions in CDR1 providing the greatest effect were 29 and the combination of 30 and 31 and the combination of 31 and 32.

Figure 9:
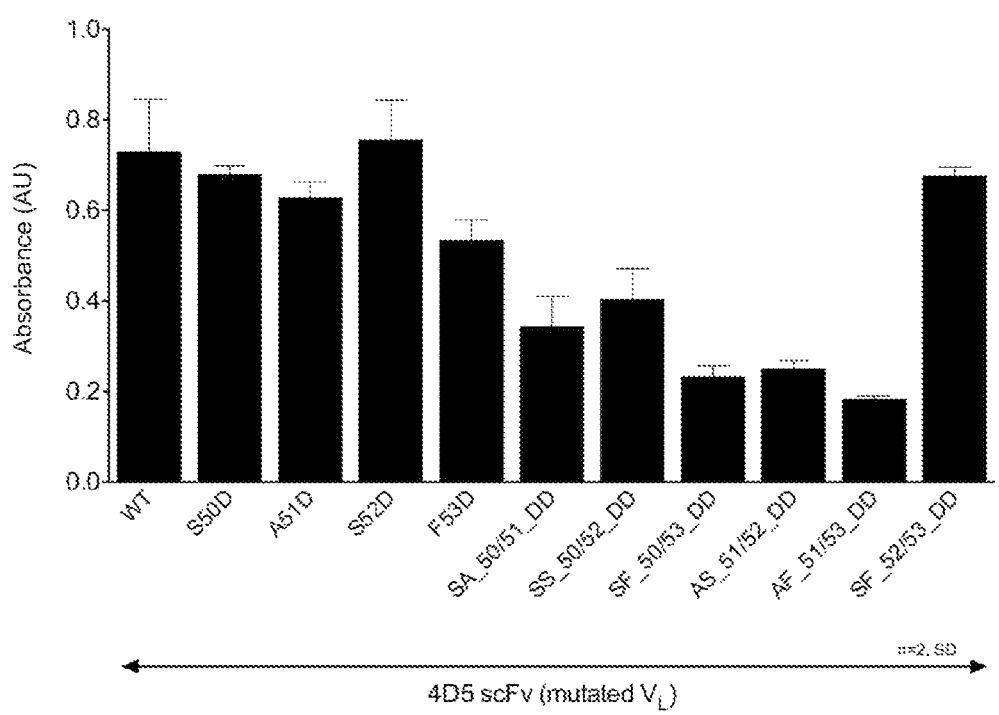
FIG. 9 is a graphical representation showing binding of scFv from 4D5 and mutant forms thereof which may comprise single negative charged amino acid changes, and combinations thereof between residues 50 and 53 to Her2 (as indicated on the X-axis). The Y-axis shows absorbance as measured at 450 nm. "WT" is the scFv from 4D5.

FIG. 9 shows that introducing negatively charged amino acids into CDR2 of a scFv derived from 4D5 does not prevent the scFv binding to Her2. In several cases, introduction of the negatively charged amino acid did not substantially change the level of binding detected compared to the level detected for wild type (non mutant) scFv.

Figure 10:
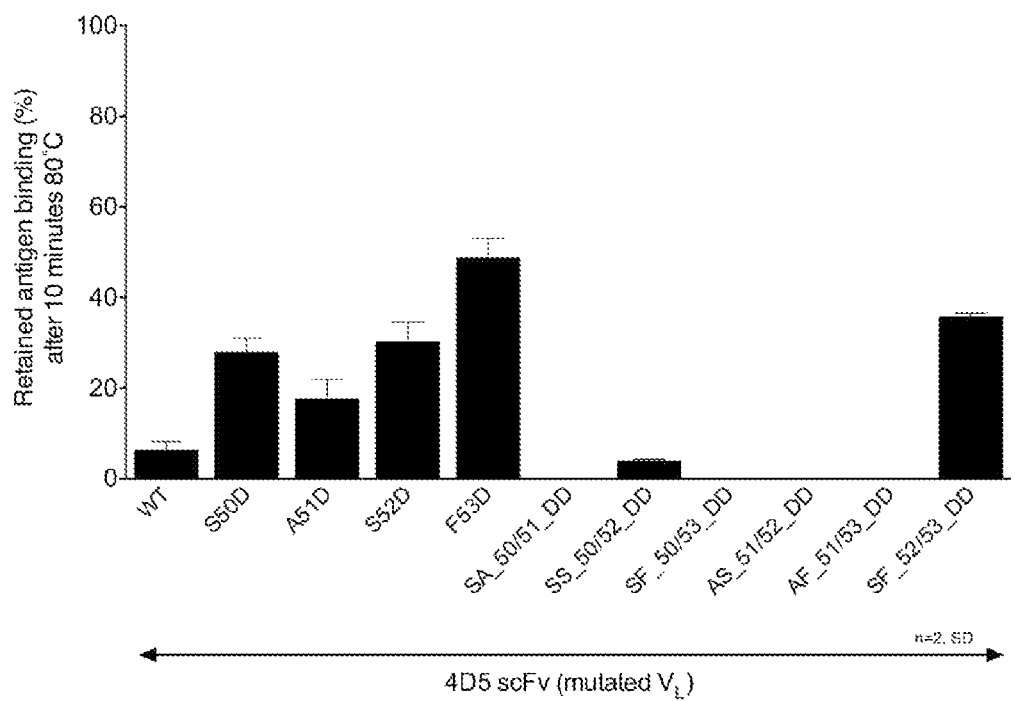
FIG. 10 is a graphical representation showing binding of scFv from 4D5 and mutant forms thereof which may comprise single negative charged amino acid changes, and combinations thereof between residues 50 and 53 to Her2 after heating to 80° C. as a percentage of the level of binding before heating. "WT" is the scFv from 4D5.

FIG. 10 shows that following heating and cooling as described above, a single negatively charged amino acid between positions 50-53 or a combination of negatively charged at positions 52 and 53 increased aggregation resistance compared to wild type (non-mutant) scFv as determined by binding to Her2 antigen after heating.

Example 9

Combinations of Negatively Charged Amino Acids in $V_L$ and $V_H$

The $V_L$ and $V_H$ of 4D5 were expressed as scFv. Mutant forms of these scFv were also produced containing one or more negatively charged amino acids within CDR2 of $V_L$ and one or more negatively charged amino acids within CDR1 of $V_H$. Single chain Fv were displayed on the surface of phage and tested for aggregation-resistance, as detailed above (see the Materials and Methods section). Briefly, phage were heated to 80° C. for 10 min, followed by cooling at 4° C. for 10 min. Correctly folded scFv were captured by a Protein A ELISA or a Protein L ELISA or an ELISA using immobilized antigen and the absorbance signal of the treated sample was calculated as a percentage of the untreated sample.

Figure 11:
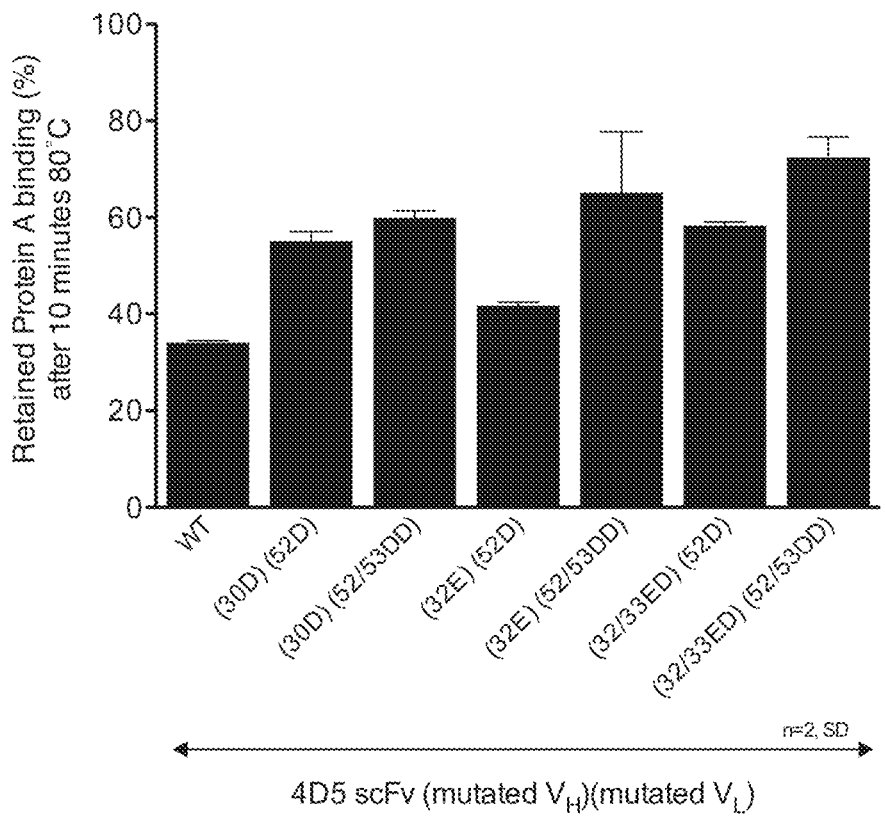
FIG. 11 is a graphical representation showing aggregation-resistance of a scFv from 4D5 which may comprise single negative charged amino acid changes, and combinations thereof in CDR2 of $V_L$ and in CDR1 of $V_H$. Positioning of any substitutions is indicated on the X axis. "WT" is the scFv from 4D5.

Results of the protein A ELISA are shown in FIG. 11. All of the combinations of negatively charged amino acids increased the level of aggregation resistance of scFvs above that observed for wild type (non mutant 4D5-derived) scFv.

Figure 12:
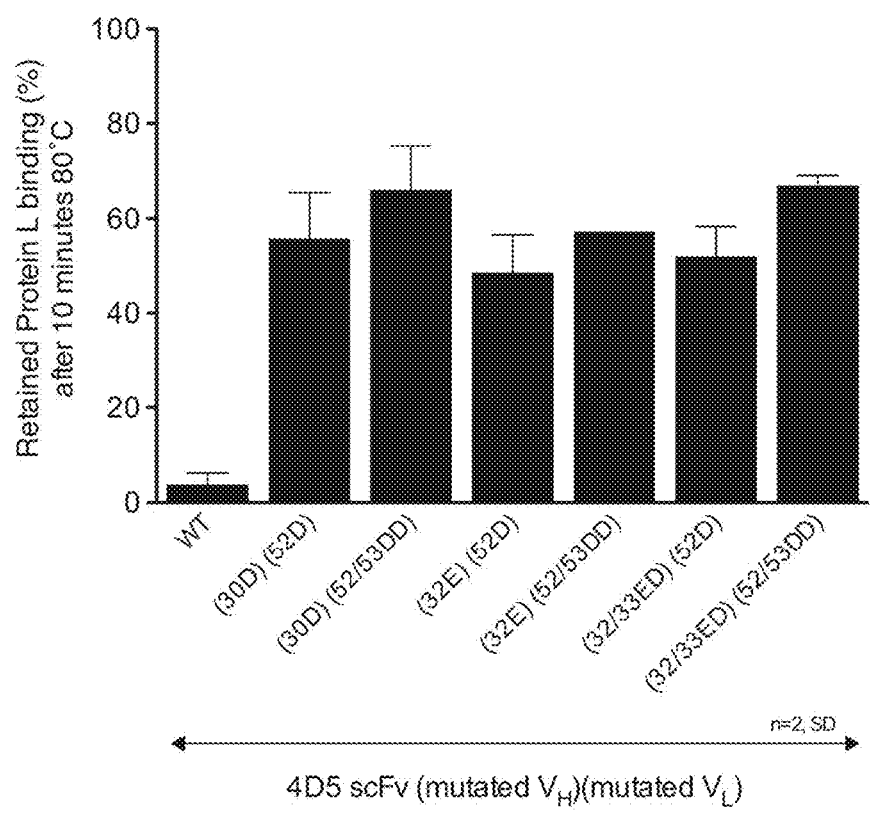
FIG. 12 is a graphical representation showing aggregation-resistance of a scFv from 4D5 which may comprise single negative charged amino acid changes, and combinations thereof in CDR2 of $V_L$ and in CDR1 of $V_H$. Positioning of any substitutions is indicated on the X axis. "WT" is the scFv from 4D5.

Results of the protein L ELISA are shown in FIG. 12. All of the combinations of negatively charged amino acids increased the level of aggregation resistance of mutant scFvs above that observed for wild type (non mutant) corresponding scFv.

Figure 13:
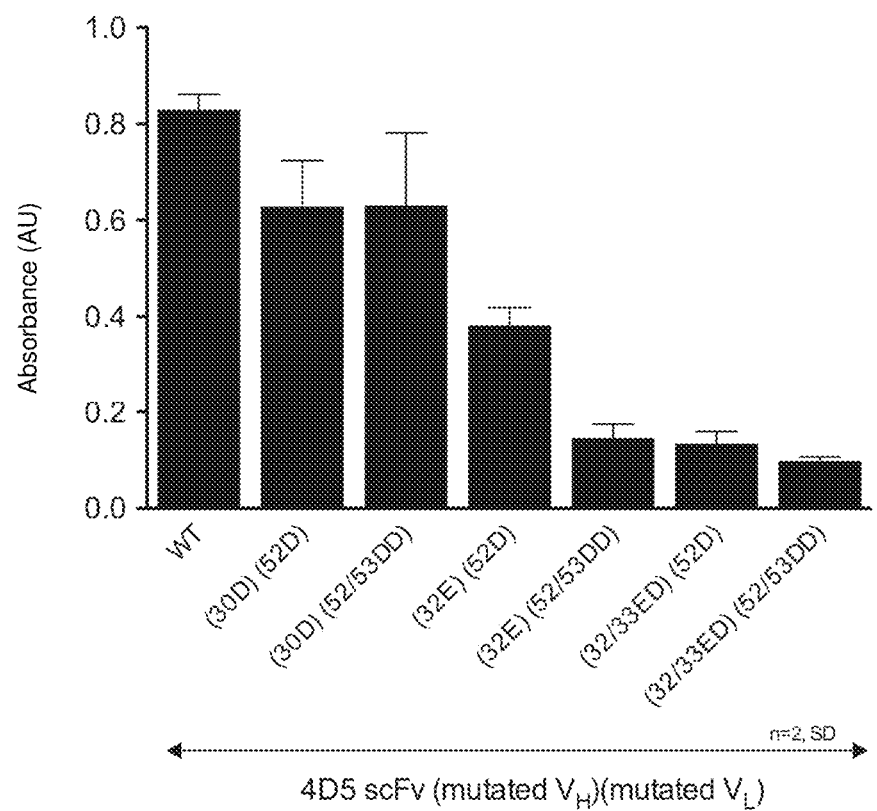
FIG. 13 is a graphical representation showing binding of scFv from 4D5 which may comprise single negative charged amino acid changes, and combinations thereof in CDR2 of $V_L$ and in CDR1 of $V_H$ to antigen. Positioning of any substitutions is indicated on the X axis. The Y-axis shows absorbance at 450 nm. "WT" is the scFv from 4D5.

FIG. 13 shows that even with negatively charged amino acid in $V_L$ CDR2 and $V_H$ CDR1, scFv were capable of binding to target antigen, with the level of binding of some mutant scFvs approaching the level observed with the corresponding wild type (non mutant) scFv.

Figure 14:
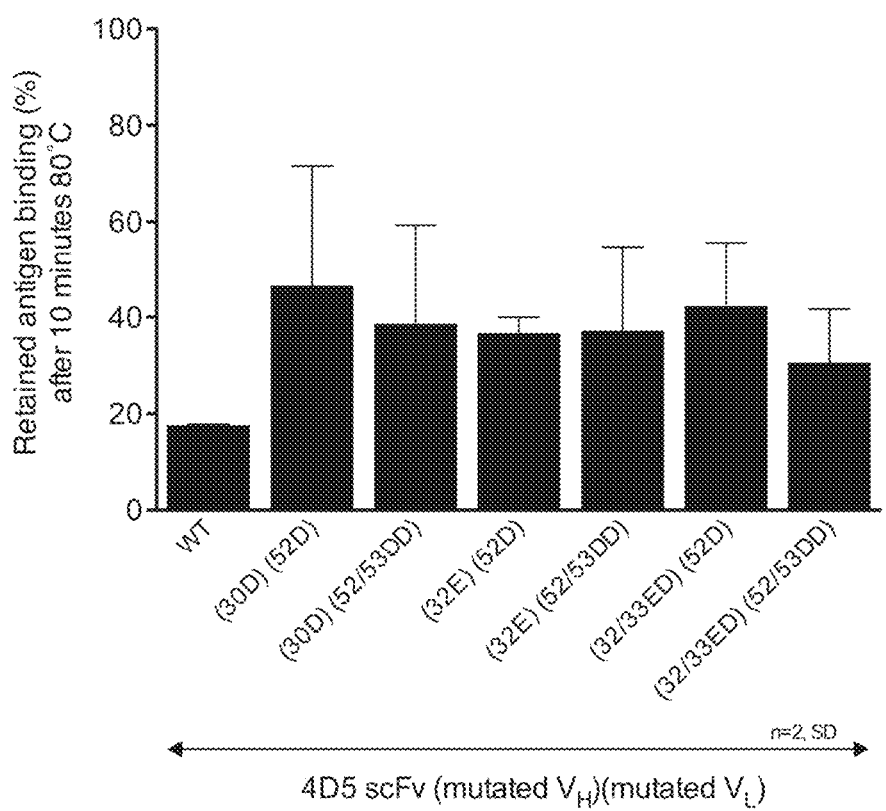
FIG. 14 is a graphical representation showing binding of scFv from 4D5 which may comprise single negative charged amino acid changes, and combinations thereof in CDR2 of $V_L$ and in CDR1 of $V_H$ to antigen after heating to 80° C. Positioning of any substitutions is indicated on the X axis. "WT" is the scFv from 4D5.

FIG. 14 shows that following heating and cooling some mutant scFvs have increased levels of retained antigen binding compared to wild type (non mutant) scFvs. All tested combinations performed better than wild type (non mutant) scFv.

Example 10

Figure 15:
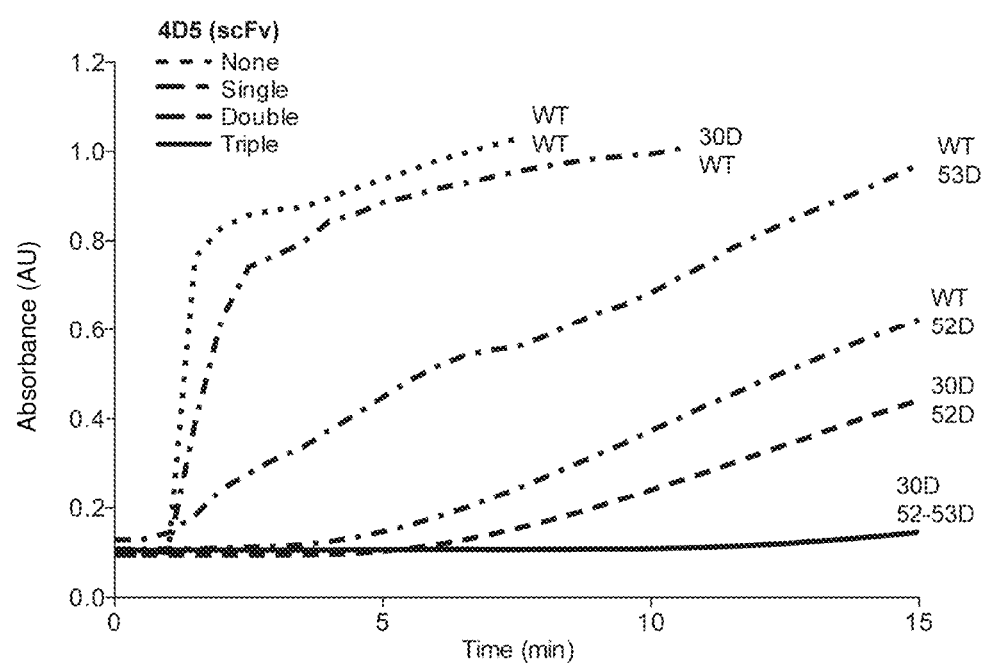
FIG. 15 is a graphical representation showing aggregation of mutant forms of scFv produced from 4D5. Positions of mutations are indicated for each line with the $V_H$ mutation being listed on top and the $V_L$ mutation being listed on the bottom. "WT" means wild type 4D5 sequence. The X-axis represents time (minutes), with time 0 being commencement of heating to 80° C. The Y axis represents absorbance measured at 360 nm as a measure of turbidity.

Combinations of Negatively Charged Amino Acids in $V_L$ and/or $V_H$ Do Not Prevent Biological Activity As a model system, mutant forms of the therapeutic antibody that binds HER2, 4D5, were studied. Negatively charged amino acids were substituted into position 30 of HCDR1 and/or either or both 52 and/or 53 of LCDR2 of 4D5 and variants were expressed as antibody fragments. To examine resistance against aggregation, 4D5 variants were heated at high concentration and turbidity measured. Resistance improved considerably as the number of mutations increased, with clear differences apparent even by simple visual inspection. This trend was observed for both $V_H$ and $V_L$ domains of 4D5. Similar results were also observed when pairing the domains through an interdomain linker in an scFv fragment format as had been observed in the single domain format (FIG. 15).

Binding affinities of representative 4D5 variants for recombinant HER2 antigen were also determined (Table 2). Affinities in the scFv fragment format ranged from about 1 nM for 4D5 to about 500 nM for some of the variants. Changes at several positions were well tolerated, with no loss of equilibrium binding affinity ($K_D$) observed. Moreover, no loss of $K_D$ was observed when combining changes within $V_H$ and $V_L$. One of the highly aggregation-resistant scFv double mutants (4D5-d) bound to HER2 with wild type (4D5) like affinity (Table 2).

TABLE 2

Affinity of 4D5 scFv mutants.

| | Mutations | | HER2 affinity | | |
|---|---|---|---|---|---|
| Clone | $V_H$ | $V_L$ | $k_a$ ($10^5$ M$^{-1}$ s$^{-1}$) | $k_d$ ($10^{-4}$ s$^{-1}$) | $K_D$ (nM) |
| 4D5 | — | — | 1.3 | 4.9 | 3.8 |
| 4D5-a | 30D | — | 2.4 | 4.9 | 2.3 |
| 4D5-b | — | 52D | 1.2 | 9.1 | 7.6 |
| 4D5-c | — | 53D | 1.5 | 175 | 118 |
| 4D5-d | 30D | 52D | 2.1 | 8.6 | 4.1 |
| 4D5-e | 30D | 52D-53D | 0.4 | 192 | 472 |

Figure 16A:
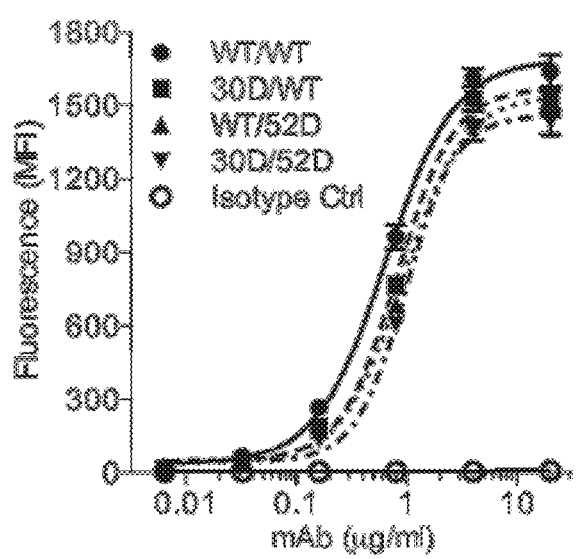
FIG. 16A is a graphical representation showing binding curves of 4D5 as complete IgG, containing mutations in CDR1 of $V_H$ and CDR2 of $V_L$, to SK-BR-3 cells as measured by flow cytometry.

To further investigate the effect of negatively charged amino acids within HCDR1 (position 30) and/or LCDR2 (position 52) on antigen binding, 4D5 variants were expressed in an immunoglobulin G (human IgG1) format. The effect of negatively charged amino acid substitutions on whole cell (SK-BR-3) binding of the variants compared to unmutated 4D5 IgG was assessed by flow cytometry (FIG. 16A). These experiments demonstrate that the binding curves and $EC_{50}$ values of 4D5 IgG variants were not considerably different to the unmutated 4D5 IgG (FIG. 16 and Table 3).

Figure 16B:
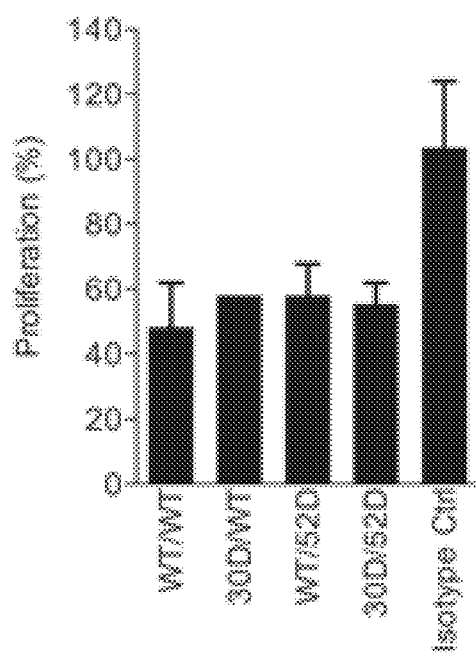
FIG. 16B is a graphical representation showing inhibition of proliferation of SK-BR-3 cells by 4d5 (WT/WT) and variants thereof containing a negatively charged amino acid in $V_H$ (30D/WT), $V_L$ (WT/52D), $V_1$ and $V_L$ (30D/52D) or isotype control antibody. Data are presented as percent proliferation in the presence of isotype control.

FIG. 16B also shows that 4D5 variants inhibited proliferation of SK-BR-3 cells to the same degree as wild-type 4D5.

TABLE 3

$EC_{50}$ values of 4D5 as human IgG1 containing negatively charged amino acid substitutions, as determined by SK-BR-3 binding assay.

| | WT/WT | 30D/WT | WT/52D | 30D/52D | Isotype Ctrl |
|---|---|---|---|---|---|
| $EC_{50}$ (μg/ml) | 0.6421 | 0.8267 | 0.9255 | 0.9779 | — |

Example 11

Effect of Negatively Charged Amino Acids on Full Length Antibodies

Figure 17A:
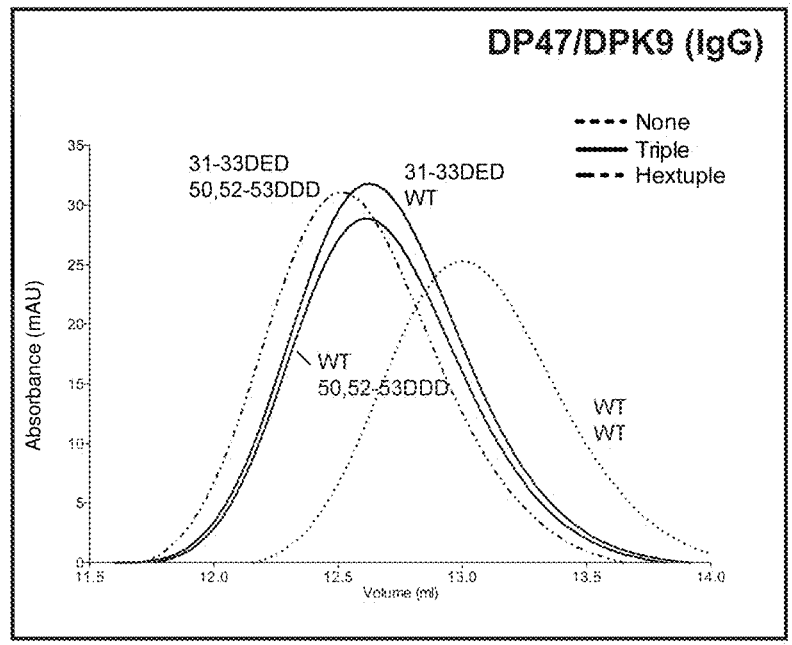
FIG. 17A is a graphical representation of the elution profile of human IgG1 which may comprise the germline $V_H3$ DP47 and the germline $V_Lk$ DPK9 containing negatively charged amino acids in CDRH1 and/or CDRL2, respectively, as measured by size-exclusion chromatography. The X-axis shows the total elution volume. The Y-axis shows absorbance at 280 nm.

To investigate the effect of negatively charged amino acids on other properties of full-length antibodies, human IgG1 molecules containing the germline $V_H$ domain DP47 and germline $V_L$ domain DPK9 with aspartate and/or glutamate substitutions in either CDR-H1 (31-33DED), CDR-L2 (50,52-53DDD) or in both domains together (31-33DED/50,52-53DDD) were analyzed by size-exclusion chromatography. Results are shown in FIG. 17A. Elution profiles showed that IgGs containing three negatively charged amino acids in both $V_H$ and $V_L$ domains (31-33DED/50,52-53DDD) eluted at a lower volume than IgGs containing triple mutations in $V_H$ (31-33DED/WT) or $V_L$ (WT/50,52-53DDD) alone, which in turn eluted at a much lower volume than IgGs with no negatively charged mutations (WT/WT).

Figure 17B:
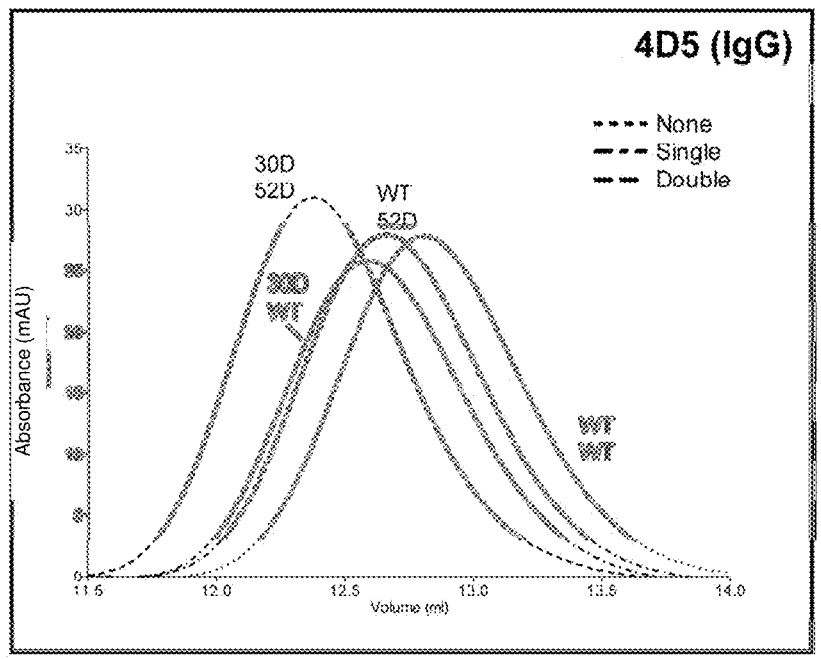
FIG. 17B is a graphical representation of the elution profile of 4D5 as whole IgG containing negatively charged amino acids in CDRH1 and/or CDRL2 as measured by size-exclusion chromatography. The X-axis shows the total elution volume. The Y-axis shows absorbance at 280 nm.

Similarly, variants of 4D5 as IgG, containing negatively charged amino acid substitutions, were assessed by size-exclusion chromatography. Results are shown in FIG. 17B. Elution profiles showed that the 4D5 IgG containing negatively charged amino acid substitutions in both $V_H$ and $V_L$ domains: at position 30 of $V_H$ and position 52 of $V_L$ (30D/52D) eluted at a lower volume compared to 4D5 IgGs containing the negatively charged amino acid substitutions in single domains alone (30D/WT or WT/52D). These in turn, eluted at a lower volume than 4D5 IgGs containing no additional negatively charged amino acid substitutions (WT/WT).

Figure 17C:
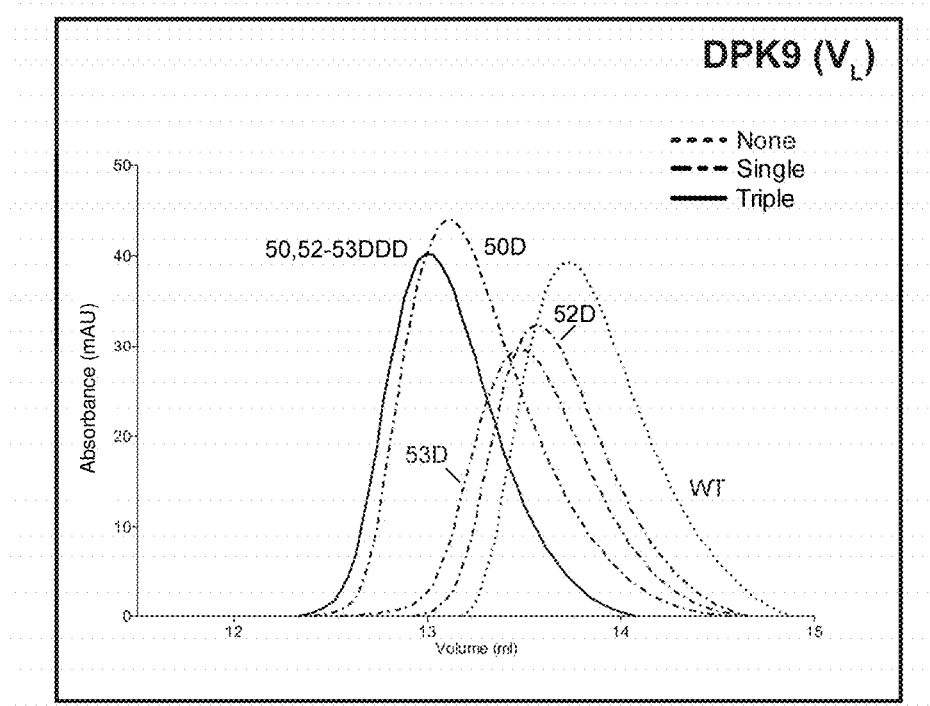
FIG. 17C is a graphical representation of the elution profile of DPK9 $V_L$ containing negatively charged amino acids in CDRL2 (either single or triple; as indicated) as measured by size-exclusion chromatography. The X-axis shows the total elution volume. The Y-axis shows absorbance at 280 nm.

These data indicate that IgGs containing negatively charged amino acid substitutions in HCDR1 or LCDR2 positions show less non-specific interactions or "stickiness" with gel-purification matrices, than IgGs without such mutations, as described by Jespers et al. (2004). This may yield higher levels of purified antibody during production and manufacture of whole IgGs. Similar results were also obtained with antibody fragments, e.g., DPK9 $V_L$ (FIG. 17C).

Example 12

Purification of Soluble Protein and Turbidity Measurements

Figure 4B:
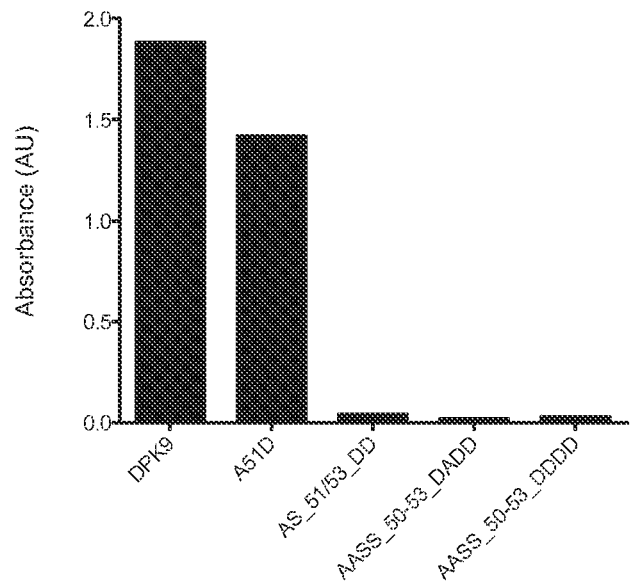
FIG. 4B is a graphical representation showing aggregation-resistance of $V_L$ from DPK9 which may comprise single negative charged amino acid changes, and combinations thereof in CDR2 of $V_L$ after heating to 85° C. as soluble protein at 100 µM. Aggregation of the $V_L$s is determined by absorbance at 320 nm as a measure of turbidity (as shown on the Y-axis). DPK9 is an example of a $V_L$ that has a low level of aggregation resistance.
Figure 5A:
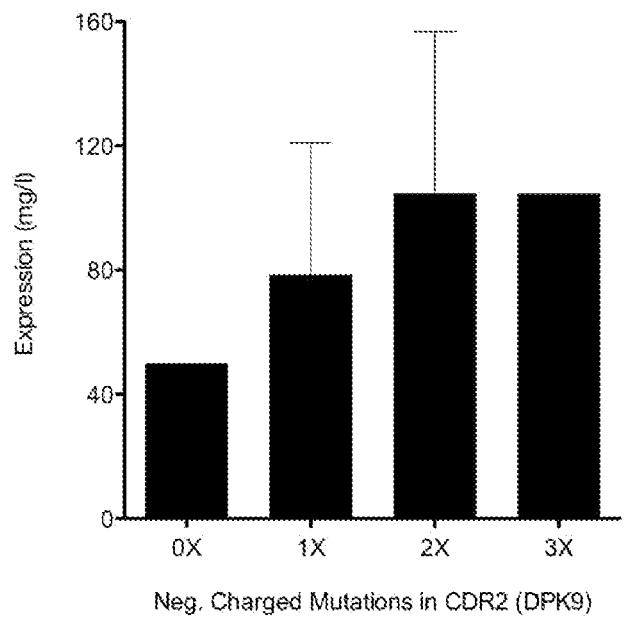
FIG. 5A-5C includes a series of graphical representations of germline $V_L$ domain DPK9 which may comprise negatively charged amino acids with improved biophysical properties such as soluble expression level (FIG. 5A), retention on gel-filtration columns (FIG. 5B) and aggregation resistance of purified protein after heating (FIG. 5B). "1×" is one negatively charged amino acid; "2×" is two negatively charged amino acids; and "3×" is three negatively charged amino acids.
Figure 5B:
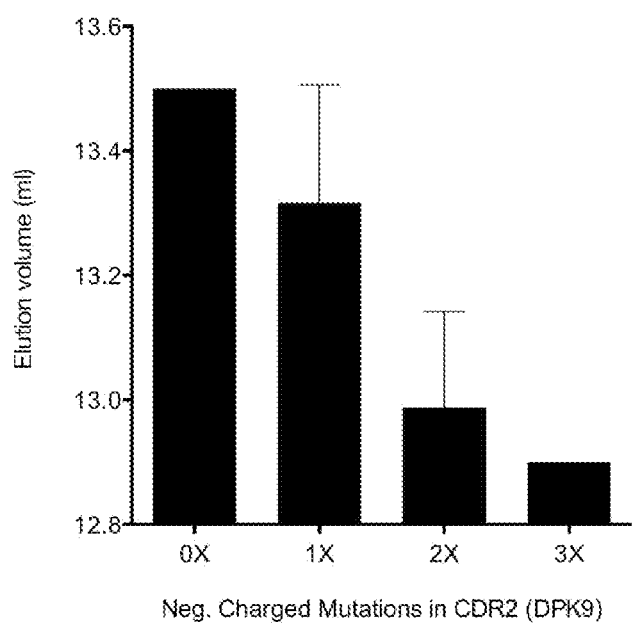
Figure 5C:
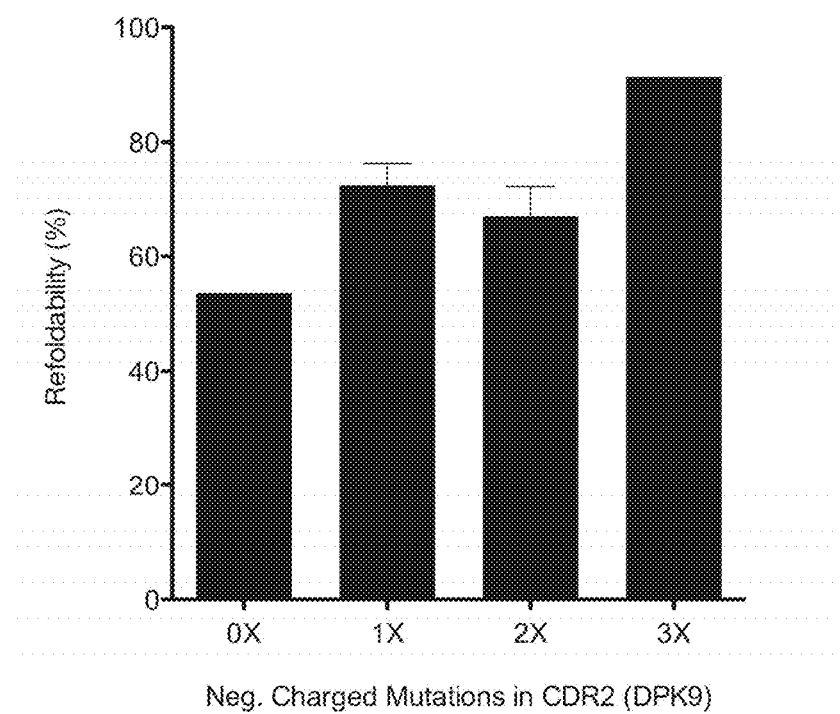

Wild type and mutant forms of $V_L$ from DPK9 or 4D5 were expressed as soluble protein and purified by affinity chromatography using Protein L resin. FIG. 4B shows that following heating and cooling mutant $V_L$ containing a single negatively charged amino acid at position 51 or multiple negatively charged amino acids between positions 50-53 have increased aggregation resistance compared to wild type (non-mutant) $V_L$ as determined by turbidity. Combinations of negatively charged amino acids between positions 50-53 provided the greatest level of aggregation resistance.

Example 13

Effect of Negatively Charged Amino Acids on Stability Following Concentration

To investigate the effect of negatively charged amino acids on resistance to aggregation following concentration (i.e., lyophilization or diafilltration) $V_L$ domains corresponding to DPK9 with aspartate substitutions in CDR-L2 (50, 52-53DDD) or without the substitutions (control) were analysed.

For lyophilization experiments, 100 µM (1.15 mg/ml) protein in 20 mM phosphate buffer pH 7.4 was snap frozen first in liquid nitrogen then transferred to speed-vac for 2 hours drying at "room temperature condition". After lyophilization, the protein was reconstituted or resuspended in water and turbidity analysed by measuring absorbance at 320 nm sing a spectrophotometer (Biophotometer, Eppendorf). Following lyophilization, the control DPK9 $V_L$ had an absorbance of 2.444, while the mutant $V_L$ had an absorbance of 0.023.

Protein recovery following gel filtration using Superdex75 was also analysed, substantially as described above. Results of this analysis showed that about 69% of the control DPK9 $V_L$ could be recovered whereas 87% of the mutant $V_L$ could be recovered.

For diafiltration experiments, 200 µl of 2 mg/ml sample in PBS buffer was centrifuged in an Amicon Ultracel (0.5 ml, 10K; Millipore) for a total of 20 min at 13,200×g. Twenty µl of PBS was added to the 30 µl retentate and absorbance at 320 nm was measured using a spectrophotometer (Biophotometer, Eppendorf). Following concentration by diafiltration, the control DPK9 $V_L$ had an absorbance of 0.580 whereas the mutant $V_L$ had an absorbance of 0.064.

These results indicate that negatively charged amino acids in CDR2 of a $V_L$ substantially reduce aggregation of the variable domain following concentration.

REFERENCES

Al-Lazikani et al., *J Mol Biol* 273, 927-948, 1997;
Andersson-Engels et al, *Phys. Med. Biol*, 42:815-824, 1997;
Arbabi-Ghahroudi et al., *Prot. Eng., Des. & Sel.*, 22: 59-66, 2009;
F. M. Ausubel et al. (editors), Current Protocols in Molecular Biology, Greene Pub. Associates and Wiley-Interscience (1988, including all updates until present);
Bendele *J Musculoskel Neuron Interact;* 1(4):377-385, 2001;
Borrebaeck (ed), Antibody Engineering, Oxford University Press, 1995 (ISBN0195091507);
Bork et al., *J Mol. Biol.* 242, 309-320, 1994;
Bradl and Linington *Brain Pathol.*, 6:303-311, 1996;
Brennan et al, *Science*, 229: 81-83, 1985;
Brinkmann et al., *Proc. Natl. Acad. Sci. USA*, 90: 7538-7542, 1993;
Carter et al *Nucleic Acids Res.* 13:4431-4443, 1985;
Carter et al. *Bio/Technology* 10: 163-167, 1992;
Chen et al. *Nature*, 446:203-207, 2007;
Cheung et al., *Virology* 176:546, 1990;
Chothia and Lesk *J. Mol Biol.* 196:901-917, 1987;
Chothia et al. *Nature* 342, 877-883, 1989;
Cornish-Bowden, *Nucl. Acids Res.* 13: 3021, 1985;
Dooley and Flajnik, *Dev Comp lmmunol.* 30:43-56, 2006;
Ewert et al., *J. mol. Biol.*, 325: 531-553, 2003;
Frangioni, *Curr. Opin. Chem. Biol*, 7:626-634, 2003;
Goding, Monoclonal Antibodies: Principles and Practice, Academic Press, (1986) pp. 59-103;
Goodman et al., (editors) Goodman and Gilman's The Pharmacological Basis of Therapeutics, 8$^{th}$ Ed., Macmillan Publishing Co. (1990);
Guss et al. *EMBO J.* 5: 1567-1575, 1986;
Guy et al., *Mol Cell Biol.* 12(3):954-61, 1992;
Harlow and Lane, Antibodies: A Laboratory Manual, Cold Spring Harbor Press, 1988;
Harris et al., *Trends Biotechnol.*, 17: 290-296, 1999;
Higuchi et al., *Nucleic Acids Res* 16(15): 7351-7367, 1988;
Higuchi, in *PCR Protocols*, pp. 177-183, Academic Press, 1990;
Ho et al *Gene (Amst.)* 77:51-59, 1989;
Holbrook et al., *Protein Eng.* 3: 659-665, 1990;
Holliger et al *Proc. Natl. Acad Sci. USA* 90: 6444-6448, 1993;
Hollinger and Hudson *Nature Biotechnology*, 23: 1126-1136, 2005;
Hoogenboom and Winter *J Mol Biol*, 227:381, 1991;
Hoyer et al., *Biophys. Chem.*, 96: 273-284, 2002;
Hu et al., *Cancer Res.*, 56: 3055-3061, 1996;
Hudson and Kortt *J. Immunol. Methods*, 231: 177-189, 1999;
Hust et al., *BMC Biotechnology* 7:14, 2007;
Ito et al *Gene* 102:67-70, 1991;
Jakobovits et al. *Nature Biotechnology* 25, 1134-1143, 2007;
Jespers et al., *J Mol Biol.;* 337: 893-903, 2004;
Kabat *Sequences of Proteins of Immunological Interest*, National Institutes of Health, Bethesda, Md., 1987 and 1991;
Kabat, E., Wu, T. T., Perry, H. M., Kay, S. and Gottesman, C. F. (1992) *Sequences of Proteins of Immunological Interest.* 5 ed. DIANE Publishing:

Kirkland et al., *J. Immunol.* 137:3614, 1986;
Kohler and Milstein *Nature*, 256:495-497, 1975;
Kostelny et al, *J. Immunol.*, 148(5):1547-1553, 1992;
Kruif and Logtenberg *J. Biol. Chem.*, 271: 7630-7634, 1996;
Kunkel et al., *Methods Enzymol.*, 154: 367, 1987;
Lee et al., *Nat Protoc.*, 2: 3001-3008, 2007;
Levin and Weiss, *Mol Biosyst.*, 2: 49-57, 2006;
Lonberg, N. "Transgenic Approaches to Human Monoclonal Antibodies." *Handbook of Experimental Pharmacology* 113: 49-101, 1994;
Largaespada et al, *Curr. Top. Microbiol. Immunol*, 166, 91-96, 1990;
Lindmark et al. *J Immunol Meth.* 62: 1-13, 1983;
Marks et al, *J. Mol. Biol.*, 222:581-597, 1991;
Matsui et al., *Cell.* 61(6):1147-55, 1990;
Matusik et al., In: Transgenics in Endocrinology, ed. By M M Matzuk, C W Brown, and T R Kumar. The Humana Press Inc (Totowa, N.J.) Chapter 19, pp 401-425, 2001
McCafferty et al., *Nature*, 348: 552-554, 1990;
Moldenhauer et al., *Scand. J. Immunol.* 32:77, 1990;
Muller et al *EMBO J.* 9(3):907-13, 1990;
Plückthun, *Immunol. Revs.*, 130:151-188, 1992;
Plückthun in The Pharmacology of Monoclonal Antibodies, vol. 113, Rosenburg and Moore eds., Springer Verlag, New York, pp. 269-315, 1994;
Presta et al., *Cancer Res.*, 57: 4593-4599, 1997;
Ramanujam et al, *IEEE Transactions on Biomedical Engineering*, 48:1034-1041, 2001;
Risma et al., *Proc Natl Acad Sci USA.*; 92(5):1322-6, 1995;
Roby et al., *Carcinogenesis.* 21(4):585-91, 2000;
Roux et al. *J. Immunol.* 161:4083, 1998;
Saha et al., BcePred:Prediction of Continuous B-Cell Epitopes in Antigenic Sequences Using Physico-chemical Properties. In Nicosia, Cutello, Bentley and Timis (Eds.) ICARIS 2004, LNCS 3239, 197-204, Springer, 2004;
Sakaguchi et al. *Nature*, 426: 454-460;
Sambrook et al. Molecular Cloning: A Laboratory Manual, Cold Spring Harbour Laboratory Press, 1989;
Sanchez-Ruiz, et al., *Biochemistry*, 27: 1648-52, 1988
Scopes In: Protein purification: principles and practice, Third Edition, Springer Verlag, 1994;
Skerra et al, *Curr. Opinion in Immunol.*, 5:256-262, 1993;
Stahli et al., *Methods in Enzinology* 9:242, 1983;
Strenglin et al *EMBO J*, 7, 1053-1059, 1988;
Tang et al. *J. Exp. Med.*, 199: 1455-1465, 2004;
Trenado et al. *J. Clin. Invest.*, 112: 1688-1696, 2002;
Van der Sluis et al. *Gastroenterology* 131: 117-129, 2006;
van Mierlo and Steemsma, *J. Biotechnol*, 79:281-98, 2000;
Virnekäs et al., *Nucl. Acids Res.* 22: 5600, 1994;
Wang et al. *J Clin Invest.* 118(7): 2629-2639, 2008;
Weissinger et al. *Proc. Natl. Acad. Sci USA*, 88, 8735-8739, 1991;
Wells et al *Gene* 34:315-323, 1985;
Willuda et al., *Cancer Res.*, 59: 5758-5767, 1999; and
Zoller and Smith, *Methods Enzymol.*, 154: 329, 1987.

The invention is further described by the following numbered paragraphs:

1. An isolated, engineered or non-naturally occurring protein comprising an antibody light chain variable domain ($V_L$) comprising a negatively charged amino acid at two or more positions between residues 49 and 56 according to the numbering system of Kabat, the protein capable of specifically binding to an antigen.

2. The protein of paragraph 1, comprising two or more negatively charged amino acids at positions selected from the group consisting of residues 49, 50, 51, 52, 53 and 56 according to the numbering system of Kabat.

3. An isolated, engineered or non-naturally occurring protein comprising:
    (i) an antibody light chain variable domain ($V_L$) comprising a negatively charged amino acid at one or more positions between residues 49 and 56 according to the numbering system of Kabat; and
    (ii) an antibody heavy chain variable domain ($V_H$) comprising a negatively charged amino acid at one or more positions selected from the group consisting of residues 28, 30, 31, 32, 33 and 35 according to the numbering system of Kabat,
    wherein the protein is capable of specifically binding to an antigen.

4. The protein of paragraph 3 comprising a negatively charged amino acid at two or more positions between residues 49 and 56 of the $V_L$ or comprising a negatively charged amino acid at two or more positions selected from the group consisting of residues 28, 30, 31, 32, 33, 35 of the $V_H$ according to the numbering system of Kabat.

5. An isolated, engineered or non-naturally occurring protein comprising:
    (i) an antibody light chain variable domain ($V_L$) comprising a negatively charged amino acid at two or more positions between residues 49 and 56 according to the numbering system of Kabat; and
    (ii) an antibody heavy chain variable domain ($V_H$) comprising a negatively charged amino acid at two or more positions selected from the group consisting of residues 28, 30, 31, 32, 33 and 35 according to the numbering system of Kabat,
    wherein the protein is capable of specifically binding to an antigen.

6. The protein of paragraph 3 or 4, wherein the $V_L$ comprises negatively charged amino acid at one or more positions selected from the group consisting of residues 49, 50, 51, 52, 53 and 56 according to the numbering system of Kabat.

7. The protein of any one of paragraphs 3 to 6, wherein the $V_L$ additionally comprises one or more negatively charged amino acids in CDR1 and/or the $V_H$ additionally comprises a negatively charged amino acid at one or more residues selected from the group consisting of residues 26, 39, 40, 50, 52, 52a and 53 according to the numbering system of Kabat.

8. The isolated, engineered or non-naturally occurring protein of any one of paragraphs 1 to 7, wherein the protein is capable of specifically binding to an antigen with an affinity of more than 10 μM.

9. The protein of any one of paragraphs 1 to 8, having a reduced tendency to aggregate compared to the protein without the negatively charged amino acid(s).

10. The protein of any one of paragraph 1 to 9, having a reduced tendency to aggregate after heating to at least about 60° C. compared to the protein without the negatively charged amino acid(s).

11. The protein according to any one of paragraphs 1 to 9 having an ability to specifically bind to the antigen after heating to at least about 60° C.

12. The protein according to any one of paragraphs 1 to 11 having a reduced tendency to aggregate after concentration and, optionally, dilution or reconstitution.

13. The protein of any one of paragraphs 1 to 12 capable of binding to a human protein.

14. The protein of any one of paragraphs 1 to 13 capable of binding to a protein associated with or causative of a human condition.

15. The protein of any one of paragraphs 1 to 14, wherein the negatively charged amino acids are aspartic acid.

16. The protein of any one of paragraphs 1 to 15, which is human or humanized or deimmunized or is fused to a human protein or region thereof.

17. A protein comprising a modified antibody light chain variable domain ($V_L$) capable of specifically binding to an antigen, wherein the $V_L$ comprises a negatively charged amino acid at one or more positions selected from the group consisting of residues 49, 51, 52, 53 and 56 according to the numbering system of Kabat, and wherein the unmodified form of the $V_L$ does not comprise the negatively charged amino acid(s).

18. The protein of paragraph 17 additionally comprising a negatively charged amino acid at position 55.

19. A protein comprising a modified antibody light chain variable domain ($V_L$) capable of specifically binding to an antigen, wherein the $V_L$ comprises a negatively charged amino acid at two or more positions between residues 49 and 56 according to the numbering system of Kabat, and wherein the unmodified form of the $V_L$ does not comprise two or more negatively charged amino acid(s) at the positions.

20. A protein comprising:
 (i) a modified antibody light chain variable domain ($V_L$) comprising a negatively charged amino acid at a position between residues 49 and 56 according to the numbering system of Kabat, wherein the unmodified form of the $V_L$ does not comprise a negatively charged amino acid at the position; and
 (ii) a modified antibody heavy chain variable domain ($V_H$) comprising a negatively charged amino acid at one or more positions selected from the group consisting of residues 28, 30, 31, 32, 33 and 35 according to the numbering system of Kabat, wherein the unmodified form of the $V_H$ does not comprise a negatively charged amino acid at the position,
 wherein the modified protein is capable of specifically binding to an antigen.

21. The protein of paragraph 19 or 20, comprising a negatively charged amino acid at one or more positions selected from the group consisting of residues 49, 50, 51, 52, 53 and 56 of $V_L$ according to the numbering system of Kabat.

22. The protein of any one of paragraphs 1 to 21, wherein the protein is selected from the group consisting of:
 (i) an antibody;
 (ii) a single domain antibody;
 (iii) a single chain Fv (scFv) containing protein;
 (iv) a diabody, a triabody or a tetrabody;
 (v) a fusion protein comprising any one of (ii)-(iv) and a Fc domain of an antibody or a domain thereof; and
 (vi) a fusion protein comprising any one of (ii)-(iv) and a protein capable of binding to an immune effector cell.

23. The protein according to any one of paragraphs 1 to 22 conjugated to a compound.

24. A composition comprising the protein of any one of paragraphs 1 to 23 and a pharmaceutically acceptable carrier.

25. A library comprising a plurality of proteins according to any one of paragraphs 1 to 24.

26. A library including proteins comprising antibody light chain variable domains ($V_L$s), the $V_L$s comprising negatively charged amino acids at one or more positions between residues 49 and 56 according to the numbering system of Kabat.

27. The library of paragraph 26, wherein the $V_1$s comprise negatively charged amino acids at two or more of the positions.

28. A library comprising proteins comprising antibody light chain variable domains ($V_L$s) and antibody heavy chain variable domains ($V_H$s), wherein the proteins comprise:
 (a) a $V_L$ comprising at least one negatively charged amino acid at one or more positions between residues 49 and 56 according to the numbering system of Kabat; and
 (b) a $V_H$ comprising a negatively charged amino acid at one or more positions selected from the group consisting of residues 28, 30, 31, 32, 33 and 35 according to the numbering system of Kabat.

29. The library of any one of paragraphs 26 to 28, wherein the proteins constitute at least 30% of the library.

30. A method for isolating the protein of any one of paragraphs 1 to 22, the method comprising contacting the library of any one of paragraphs 26 to 28 with the antigen and isolating a protein that binds thereto.

31. A method for increasing the aggregation-resistance of a protein comprising an antibody light chain variable domain ($V_L$), the method comprising modifying the $V_L$ by substituting an amino acid at one or more positions selected from the group consisting of residues 49, 50, 51, 52, 53 and 56 according to the numbering system of Kabat with a negatively charged amino acid.

32. A method for increasing the aggregation-resistance of a protein comprising an antibody light chain variable domain ($V_L$), the method comprising modifying the $V_L$ such that it comprises negatively charged amino acids at two or more positions between residues 49 and 56 according to the numbering system of Kabat, wherein the unmodified protein does not comprise the two or more negatively charged amino acids.

33. A method for increasing the aggregation-resistance of a protein comprising an antibody light chain variable domain ($V_L$) and an antibody heavy chain variable domain ($V_H$), the method comprising modifying the protein such that it comprises:
 (i) a negatively charged amino acid at one or more positions between residues 49 and 56 of the $V_L$ according to the numbering system of Kabat; and
 (ii) a negatively charged amino acid at one or more positions selected from the group consisting of residues 28, 30, 31, 32, 33 and 35 of the $V_H$ according to the numbering system of Kabat,
 wherein the protein prior to modification does not comprise a negatively charged amino acid at the positions in the $V_L$ and the $V_H$.

34. The method of paragraph 33, comprising:
 (i) modifying the $V_L$ by substituting an amino acid at one or more positions between residues 49 and 56 of the $V_L$ according to the numbering system of Kabat with a negatively charged amino acid; and
 (ii) modifying the $V_H$ by substituting an amino acid at one or more positions selected from the group consisting of residues 28, 30, 31, 32, 33 and 35 according to the numbering system of Kabat with a negatively charged amino acid.

35. A method for increasing the aggregation-resistance of a protein comprising an antibody light chain variable domain ($V_L$) and an antibody heavy chain variable domain ($V_H$), the method comprising modifying the protein such that it comprises:
 (i) a negatively charged amino acid at two or more positions between residues 49 and 56 of the $V_L$ according to the numbering system of Kabat; and
 (ii) a negatively charged amino acid at two or more positions selected from the group consisting of residues 28, 30, 31, 32, 33 and 35 of the $V_H$ according to the numbering system of Kabat, wherein the protein prior to modification does not comprise a negatively charged amino acid at the positions in the $V_L$ and the $V_H$.

36. The method of paragraph 35, comprising:
(i) modifying the $V_L$ by substituting an amino acid at two or more positions between residues 49 and 56 of the $V_L$ according to the numbering system of Kabat with a negatively charged amino acid; and
(ii) modifying the $V_H$ by substituting an amino acid at two or more positions selected from the group consisting of residues 28, 30, 31, 32, 33 and 35 according to the numbering system of Kabat with a negatively charged amino acid.

37. The method of any one of paragraphs 33 to 36 additionally comprising modifying the sprotein such that the $V_L$ additionally comprises one or more negatively charged amino acids in CDR1 and/or the $V_H$ additionally comprises a negatively charged amino acid at one or more residues selected from the group consisting of residues 26, 39, 40, 50, 52, 52a and 53 according to the numbering system of Kabat.

38. Use of the protein of any one of paragraphs 1 to 23 or the composition of paragraph 24 in medicine.

39. A method of treating or preventing a condition in a subject, the method comprising administering the protein of any one of paragraphs 1 to 23 or the composition according to paragraph 24 to a subject in need thereof.

40. A method for delivering a compound to a cell, the method comprising contacting the cell with the protein of paragraph 23 or the composition according to paragraph 24, wherein the protein is conjugated to the compound.

41. A method for diagnosing or prognosing a condition in a subject, the method comprising contacting a sample from the subject with the protein of any one of paragraphs 1 to 23 or the composition of paragraph 24 such that the protein binds to an antigen and forms a complex and detecting the complex, wherein detection of the complex is diagnostic or prognostic of the condition in the subject.

42. The method of paragraph 41, comprising determining the level of the complex, wherein an enhanced or reduced level of said complex is diagnostic or prognostic of the condition in the subject.

43. A method for localising or detecting an antigen in a subject, said method comprising detecting or localising the protein of paragraph 23 or the composition of paragraph 24 in the subject, wherein the protein binds to the antigen, and wherein the protein is conjugated to a detectable label.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method for increasing the aggregation-resistance of an antibody having a light chain variable domain ($V_L$) and a heavy chain variable domain ($V_H$), the method comprising
substituting an amino acid at one or more positions of the $V_L$ selected from the group consisting of residues 51, 52, 53 and 56 according to the numbering system of Kabat with an aspartate or a glutamate to obtain
an antibody with a reduced propensity to aggregate.

2. The method of claim 1, wherein the $V_H$ comprises an aspartate or a glutamate at one, two or three positions selected from the group consisting of residues 28, 30, 31, 32, 33 and 35 according to the numbering system of Kabat.

3. The method of claim 1, wherein the amino acid at one or more positions is a glutamate.

4. The method of claim 1, wherein the amino acid at one or more positions is an aspartate.

5. The method of claim 1, wherein two or more positions are substituted.

6. The method of claim 5, wherein the amino acids at the two or more positions are an aspartate and a glutamate.

7. The method of claim 1, wherein the antibody has a reduced propensity to aggregate at a temperature of at least about 60° C.

8. The method of claim 1, wherein the antibody has a reduced propensity to aggregate after concentration.

* * * * *

```
                       SEQUENCE LISTING

<160> NUMBER OF SEQ ID NOS: 16

<210> SEQ ID NO 1
<211> LENGTH: 107
<212> TYPE: PRT
<213> ORGANISM: Homo sapiens

<400> SEQUENCE: 1

Gln Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Asn
                85                  90                  95

Thr Phe Gly Gln Gly Thr Lys Val Glu Ile Lys
            100                 105

<210> SEQ ID NO 2
<211> LENGTH: 321
<212> TYPE: DNA
<213> ORGANISM: Homo sapiens

<400> SEQUENCE: 2
cagatccaga tgacccagtc tccatcctcc ctgtctgcat ctgtaggaga cagagtcacc      60
atcacttgcc gggcaagtca gagcattagc agctatttaa attggtatca gcagaaacca     120
gggaaagccc ctaagctcct gatctatgct gcatccagtt tgcaaagtgg ggtcccatca     180
```

```
aggttcagtg gcagtggatc tgggacagat ttcactctca ccatcagcag tctgcaacct    240
gaagattttg caacttacta ctgtcaacag agttacagta cccctaacac gttcggccaa    300
gggaccaagg tggaaatcaa a                                              321
```

<210> SEQ ID NO 3
<211> LENGTH: 107
<212> TYPE: PRT
<213> ORGANISM: Homo sapiens

<400> SEQUENCE: 3

```
Gln Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asp Tyr
            20                  25                  30

Leu Asn Trp Tyr Gln Gln Lys Pro Gly Lys Ala Pro Lys Leu Leu Ile
        35                  40                  45

Tyr Asp Asp Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Gly Tyr Ala Pro Ser
                85                  90                  95

Thr Phe Gly Gln Gly Thr Lys Val Glu Ile Lys
            100                 105
```

<210> SEQ ID NO 4
<211> LENGTH: 321
<212> TYPE: DNA
<213> ORGANISM: Homo sapiens

<400> SEQUENCE: 4

```
cagatccaga tgacccagtc tccatcctcc ctgtctgcat ctgtaggaga cagagtcacc    60
atcacttgcc gggcaagtca ggatattagc gattatttaa attggtatca gcagaaacca    120
gggaaagccc ctaagctcct gatctatgat gattcctctt tgcaaagtgg ggtcccatca    180
aggttcagtg gcagtggatc tgggacagat ttcactctca ccatcagcag tctgcaacct    240
gaagattttg caacttacta ctgtcaacag ggtggttacg ctccttctac gttcggccaa    300
gggaccaagg tggaaatcaa a                                              321
```

<210> SEQ ID NO 5
<211> LENGTH: 243
<212> TYPE: PRT
<213> ORGANISM: artificial
<220> FEATURE:
<223> OTHER INFORMATION: amino acid sequence encoding control scFv

<400> SEQUENCE: 5

```
Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Arg Ile Ser Asp Glu
            20                  25                  30

Asp Met Gly Trp Val Arg Gln Ala Pro Gly Lys Gly Leu Glu Trp Val
        35                  40                  45

Ser Ser Ile Tyr Gly Pro Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
```

```
                65                  70                  75                  80
Leu Gln Met Asn Ser Leu Arg Ala Glu Asp Thr Ala Val Tyr Tyr Cys
                        85                  90                  95

Ala Ser Ala Leu Glu Pro Leu Ser Glu Pro Leu Gly Phe Trp Gly Gln
                100                 105                 110

Gly Thr Leu Val Thr Val Ser Ser Gly Gly Gly Gly Ser Gly Gly Gly
            115                 120                 125

Gly Ser Gly Gly Gly Gly Ser Thr Asp Ile Gln Met Thr Gln Ser Pro
130                 135                 140

Ser Ser Leu Ser Ala Ser Val Gly Asp Arg Val Thr Ile Thr Cys Arg
145                 150                 155                 160

Ala Ser Gln Ser Ile Ser Ser Tyr Leu Asn Trp Tyr Gln Gln Lys Pro
                165                 170                 175

Gly Lys Ala Pro Lys Leu Leu Ile Tyr Asp Ala Ser Asp Leu Gln Ser
            180                 185                 190

Gly Val Pro Ser Arg Phe Ser Gly Ser Gly Ser Gly Thr Asp Phe Thr
        195                 200                 205

Leu Thr Ile Ser Ser Leu Gln Pro Glu Asp Phe Ala Thr Tyr Tyr Cys
    210                 215                 220

Gln Gln Ile Asp Tyr Thr Pro Thr Thr Phe Gly Gln Gly Thr Lys Val
225                 230                 235                 240

Glu Ile Lys

<210> SEQ ID NO 6
<211> LENGTH: 729
<212> TYPE: DNA
<213> ORGANISM: artificial
<220> FEATURE:
<223> OTHER INFORMATION: nucleotide sequence encoding control scFv

<400> SEQUENCE: 6
caggtgcagc tgttggagtc tgggggaggc ttggtacagc ctgggggtc cctgcgtctc      60
tcctgtgcag cctccggatt taggattagc gatgaggata tgggctgggt ccgccaggct     120
ccagggaagg gtctagagtg ggtatcaagc atttatggcc tagcggtag cacatactac      180
gcagactccg tgaagggccg gttcaccatc tcccgtgaca attccaagaa cacgctgtat     240
ctgcaaatga acagcctgcg tgccgaggac accgcggtat attattgcgc gagtgctttg    300
gagccgcttt cggagcccct gggcttttgg ggtcagggaa ccctggtcac cgtctcgagc    360
ggtggaggcg gttcaggcgg aggtggcagc ggcggtggcg gtcgacgga catccagatg      420
acccagtctc catcctccct gtctgcatct gtaggagaca gagtcaccat cacttgccgg    480
gcaagtcaga gcattagcag ctatttaaat tggtatcagc agaaaccagg aaagccccct    540
aagctcctga tctatgatgc atccgatttg caaagtgggg tcccatcaag gttcagtggc    600
agtggatctg ggacagattt cactctcacc atcagcagtc tgcaacctga gattttgca     660
acttactact gtcaacagat cgactacact cctactacgt tcggccaagg gaccaaggtg   720
gaaatcaaa                                                            729

<210> SEQ ID NO 7
<211> LENGTH: 107
<212> TYPE: PRT
<213> ORGANISM: artificial
<220> FEATURE:
<223> OTHER INFORMATION: amino acid sequence of adalimumab VL

<400> SEQUENCE: 7
```

Gln Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65              70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys
            100                 105

<210> SEQ ID NO 8
<211> LENGTH: 321
<212> TYPE: DNA
<213> ORGANISM: artificial
<220> FEATURE:
<223> OTHER INFORMATION: nucleotide sequence encoding adalimumab VL

<400> SEQUENCE: 8
cagattcaga tgacccagag cccgagcagc ctgagcgcaa gcgttggtga tcgtgttacc     60
attacctgtc gtgcaagcca gggtattcgt aattatctgg catggtatca gcagaaaccg    120
ggtaaagcac cgaaactgct gatttatgca gcaagcaccc tgcagagcgg tgttccgagc    180
cgttttagcg gtagcggtag tggcaccgat tttaccctga ccattagcag cctgcagccg    240
gaagatgttg caacctatta ttgtcagcgt tataatcgcg caccgtatac ctttggtcag    300
ggcaccaaag ttgaaattaa a                                              321

<210> SEQ ID NO 9
<211> LENGTH: 244
<212> TYPE: PRT
<213> ORGANISM: artificial
<220> FEATURE:
<223> OTHER INFORMATION: amino acid sequence of adalimumab scFv

<400> SEQUENCE: 9

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65              70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Ala Asp Ile Gln Met Thr Gln Ser

```
                130              135              140
Pro Ser Ser Leu Ser Ala Ser Val Gly Asp Arg Val Thr Ile Thr Cys
145                 150                 155                 160

Arg Ala Ser Gln Gly Ile Arg Asn Tyr Leu Ala Trp Tyr Gln Gln Lys
                165                 170                 175

Pro Gly Lys Ala Pro Lys Leu Leu Ile Tyr Ala Ala Ser Thr Leu Gln
            180                 185                 190

Ser Gly Val Pro Ser Arg Phe Ser Gly Ser Gly Ser Gly Thr Asp Phe
        195                 200                 205

Thr Leu Thr Ile Ser Ser Leu Gln Pro Glu Asp Val Ala Thr Tyr Tyr
    210                 215                 220

Cys Gln Arg Tyr Asn Arg Ala Pro Tyr Thr Phe Gly Gln Gly Thr Lys
225                 230                 235                 240

Val Glu Ile Lys

<210> SEQ ID NO 10
<211> LENGTH: 732
<212> TYPE: DNA
<213> ORGANISM: artificial
<220> FEATURE:
<223> OTHER INFORMATION: nucleotide sequence encoding adalimumab scFv

<400> SEQUENCE: 10
caggttcagc tggttgaaag cggtggtggt ctggttcagc ctggtcgtag cctgcgtctg    60
agctgtgcag caagcggttt tacctttgat gattatgcaa tgcattgggt tcgtcaggca   120
ccgggtaaag gtctggaatg ggttagcgca attacctgga atagcggtca tattgattat   180
gcagatagcg ttgaaggtcg ctttaccatt agccgtgata atgcaaaaaa tagcctgtat   240
ctgcagatga atagcctgcg tgcagaagat accgcagttt attattgtgc aaagttagc   300 tatctgagca ccgcaagcag cctggattat tggggtcagg gcaccctggt taccgtctcg   360
agcggtggtg gtggtagcgg tggtggcggt tcaggtggtg gtggcagtgc agatattcag   420
atgacccaga gcccgagcag cctgagcgca agcgttggtg atcgtgttac cattacctgt   480
cgtgcaagcc agggtattcg taattatctg gcatggtatc agcagaaacc gggtaaagca   540
ccgaaactgc tgatttatgc agcaagcacc ctgcagagcg gtgttccgag ccgttttagc   600
ggtagcggta gtggcaccga ttttaccctg accattagca gcctgcagcc ggaagatgtt   660
gcaacctatt attgtcagcg ttataatcgc gcaccgtata cctttggtca gggcaccaaa   720
gttgaaatta aa                                                      732

<210> SEQ ID NO 11
<211> LENGTH: 107
<212> TYPE: PRT
<213> ORGANISM: artificial
<220> FEATURE:
<223> OTHER INFORMATION: amino acid sequence of VL of 4D5

<400> SEQUENCE: 11

Gln Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Glu Ser Gly Val Pro Ser Arg Phe Ser Gly
    50                  55                  60
```

```
Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                 85                  90                  95

Thr Phe Gly Gln Gly Thr Lys Val Glu Ile Lys
            100                 105

<210> SEQ ID NO 12
<211> LENGTH: 321
<212> TYPE: DNA
<213> ORGANISM: artificial
<220> FEATURE:
<223> OTHER INFORMATION: nucleotide sequence encoding VL of 4D5

<400> SEQUENCE: 12
cagattcaga tgacccagag cccgagcagc ctgagcgcaa gcgttggtga tcgtgttacc    60
attacctgtc gtgcaagcca ggatgttaat accgcagttg catggtatca gcagaaaccg   120
ggtaaagcac cgaaactgct gatttatagc gcatcttttc tggaaagcgg tgttccgagc   180
cgttttagcg gtagccgtag cggcaccgat tttaccctga ccattagcag cctgcagccg   240
gaagattttg caacctatta ttgtcagcag cattatacca cacctccgac ctttggccag   300
ggcaccaaag ttgaaattaa a                                             321

<210> SEQ ID NO 13
<211> LENGTH: 243
<212> TYPE: PRT
<213> ORGANISM: artificial
<220> FEATURE:
<223> OTHER INFORMATION: amino acid sequence of 4D5 scFv

<400> SEQUENCE: 13

Gln Val Gln Leu Val Glu Ser Gly Gly Gly Leu Val Gln Pro Gly Gly
  1               5                  10                  15

Ser Leu Arg Leu Ser Cys Ala Ala Ser Gly Phe Asn Ile Lys Asp Thr
             20                  25                  30

Tyr Ile His Trp Val Arg Gln Ala Pro Gly Lys Gly Leu Glu Trp Val
         35                  40                  45

Ala Arg Ile Tyr Pro Thr Asn Gly Tyr Thr Arg Tyr Ala Asp Ser Val
     50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ser Arg Trp Gly Gly Asp Gly Phe Tyr Ala Met Asp Val Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Thr Asp Ile Gln Met Thr Gln Ser Pro
    130                 135                 140

Ser Ser Leu Ser Ala Ser Val Gly Asp Arg Val Thr Ile Thr Cys Arg
145                 150                 155                 160

Ala Ser Gln Asp Val Asn Thr Ala Val Ala Trp Tyr Gln Gln Lys Pro
                165                 170                 175

Gly Lys Ala Pro Lys Leu Leu Ile Tyr Ser Ala Ser Phe Leu Glu Ser
            180                 185                 190

Gly Val Pro Ser Arg Phe Ser Gly Ser Arg Ser Gly Thr Asp Phe Thr
```

```
                195                 200                 205
Leu Thr Ile Ser Ser Leu Gln Pro Glu Asp Phe Ala Thr Tyr Tyr Cys
    210                 215                 220

Gln Gln His Tyr Thr Thr Pro Pro Thr Phe Gly Gln Gly Thr Lys Val
225                 230                 235                 240

Glu Ile Lys

<210> SEQ ID NO 14
<211> LENGTH: 729
<212> TYPE: DNA
<213> ORGANISM: artificial
<220> FEATURE:
<223> OTHER INFORMATION: nucleotide sequence encoding 4D5 scFv

<400> SEQUENCE: 14
caggttcagc tggttgaaag cggtggtggt ctggttcagc ctggtggtag cctgcgtctg      60
agctgtgcag caagcggttt taatattaaa gataccctata ttcattgggt gcgtcaggca     120
ccgggtaaag gtctggaatg ggttgcacgt atttatccga ccaatggtta tacccgttat     180
gcagatagcg tgaaaggtcg ttttaccatt agcgcagata ccagcaaaaa taccgcatat     240
ctgcagatga tagcctgcg tgcagaagat accgcagttt attattgtag ccgttggggt     300
ggtgatggtt tttatgcaat ggatgtttgg ggtcagggca ccctggttac cgttagcagt     360
ggtggtggtg gtagcggtgg tggcggttct ggtggcggtg gtagtaccga tattcagatg     420
acccagagcc cgagcagcct gagcgcaagc gttggtgatc gtgttaccat tacctgtcgt     480
gcaagccagg atgttaatac cgcagttgca tggtatcagc agaaaccggg taaagcaccg     540
aaactgctga tttatagcgc atcttttctg gaaagcggtg ttccgagccg ttttagcggt     600
agccgtagcg gcaccgattt taccctgacc attagcagcc tgcagccgga agattttgca     660
acctattatt gtcagcagca ttataccaca cctccgacct ttggccaggg caccaaagtt     720
gaaattaaa                                                            729

<210> SEQ ID NO 15
<211> LENGTH: 120
<212> TYPE: PRT
<213> ORGANISM: artificial
<220> FEATURE:
<223> OTHER INFORMATION: amino acid sequence of 4D5 VH

<400> SEQUENCE: 15

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Val Trp Gly Gln
            100                 105                 110

Gly Thr Leu Val Thr Val Ser Ser
        115                 120
```

```
<210> SEQ ID NO 16
<211> LENGTH: 360
<212> TYPE: DNA
<213> ORGANISM: artificial
<220> FEATURE:
<223> OTHER INFORMATION: nucleotide sequence encoding 4D5 VH

<400> SEQUENCE: 16
caggttcagc tggttgaaag cggtggtggt ctggttcagc ctggtggtag cctgcgtctg        60
agctgtgcag caagcggttt taatattaaa gatacctata ttcattgggt gcgtcaggca       120
ccgggtaaag gtctggaatg ggttgcacgt atttatccga ccaatggtta tacccgttat       180
gcagatagcg tgaaaggtcg ttttaccatt agcgcagata ccagcaaaaa taccgcatat       240
ctgcagatga atagcctgcg tgcagaagat accgcagttt attattgtag ccgttggggt       300
ggtgatggtt tttatgcaat ggatgtttgg ggtcagggca ccctggttac cgttagcagt       360
```